(12) United States Patent
Griffis

(10) Patent No.: US 10,744,223 B2
(45) Date of Patent: Aug. 18, 2020

(54) SCENTED MATERIAL COMPOSITIONS AND ARTICLES FOR USE WITH FOOD AND BEVERAGE

(71) Applicant: Szent Co., Santa Monica, CA (US)

(72) Inventor: Shawn Griffis, Santa Monica, CA (US)

(73) Assignee: SZENT CO., Santa Monica, CA (US)

( * ) Notice: Subject to any disclaimer, the term of this patent is extended or adjusted under 35 U.S.C. 154(b) by 0 days.

(21) Appl. No.: 16/368,796

(22) Filed: Mar. 28, 2019

(65) Prior Publication Data

US 2019/0224359 A1 Jul. 25, 2019

Related U.S. Application Data

(63) Continuation-in-part of application No. 16/136,664, filed on Sep. 20, 2018, which is a continuation of
(Continued)

(51) Int. Cl.
*A61L 9/12* (2006.01)
*B65D 23/12* (2006.01)
(Continued)

(52) U.S. Cl.
CPC ............... *A61L 9/12* (2013.01); *A61L 9/042* (2013.01); *B29B 9/16* (2013.01); *B29C 48/0011* (2019.02);
(Continued)

(58) Field of Classification Search
CPC .. B65D 23/00; B65D 51/245; B65D 2203/12; B65D 75/5855; B32B 7/12; B32B 27/18; A61L 19/12; A61L 19/048
(Continued)

(56) References Cited

U.S. PATENT DOCUMENTS

D25,131 S 1/1896 Fowler, Jr.
D28,746 S 5/1898 Blount
(Continued)

FOREIGN PATENT DOCUMENTS

DE 102006038257 A1 2/2008
DE 102009020524 A1 11/2010
(Continued)

OTHER PUBLICATIONS

Etsy. Mini Orange Plastic Soda Bottle Rings/Safety Seals. Mar. 23, 2018 [earliest online date], [site visited Apr. 23, 2018]. Available from Internet, <URL:https://etsy.me/2HSzu7f. (Year: 2018).
(Continued)

*Primary Examiner* — Ernesto A Grano
(74) *Attorney, Agent, or Firm* — Perkins Coie LLP

(57) ABSTRACT

Disclosed are scented material compositions, articles and methods of their manufacture. In some aspects, a scented attachment for a beverage container includes a scented article including a body loaded with a volatile chemical compound to emanate from the body of the scented article to generate a scent, in which the scented article includes at least one interior protruding structure that projects from an interior wall of the body of the scented article and is configured to attach to a bottle and be enclosed by a cap and the bottle when the cap is securely fastened to the bottle, such that the scent from the scented attachment is trapped when the cap is securely attached to the bottle and releases into an outer environment when the cap is detached from the bottle, in which the scented article comprises a scented material formed of a fragrance oil and a plastic base material.

12 Claims, 20 Drawing Sheets

Related U.S. Application Data application No. 15/782,720, filed on Oct. 12, 2017, now Pat. No. 10,086,104, which is a continuation of application No. 15/588,571, filed on May 5, 2017, now Pat. No. 9,801,969, which is a continuation-in-part of application No. 13/429,300, filed on Mar. 23, 2012, now abandoned.

(60) Provisional application No. 62/649,215, filed on Mar. 28, 2018, provisional application No. 61/467,888, filed on Mar. 25, 2011.

(51) Int. Cl.

| | |
|---|---|
| *B65D 51/24* | (2006.01) |
| *B65D 1/02* | (2006.01) |
| *B65D 41/04* | (2006.01) |
| *B65D 23/14* | (2006.01) |
| *B29B 9/16* | (2006.01) |
| *A61L 9/04* | (2006.01) |
| *B29C 48/00* | (2019.01) |
| *B29K 105/00* | (2006.01) |
| *B29B 9/06* | (2006.01) |

(52) U.S. Cl.
CPC ........... *B65D 1/0246* (2013.01); *B65D 23/12* (2013.01); *B65D 23/14* (2013.01); *B65D 41/04* (2013.01); *B65D 41/0492* (2013.01); *B65D 51/24* (2013.01); *B65D 51/245* (2013.01); *H05K 999/99* (2013.01); *A61L 2209/15* (2013.01); *B29B 9/065* (2013.01); *B29K 2105/0029* (2013.01); *B65D 2203/12* (2013.01); *B65D 2517/0053* (2013.01); *B65D 2517/5091* (2013.01)

(58) Field of Classification Search
USPC ........................................................ 220/694
See application file for complete search history.

(56) References Cited

U.S. PATENT DOCUMENTS

| | | |
|---|---|---|
| D30,338 S | 3/1899 | Mann |
| D31,451 S | 8/1899 | Norris |
| D32,681 S | 5/1900 | Morgenthaler |
| D44,392 S | 7/1912 | Whitney |
| D99,688 S | 5/1936 | Tomlinson |
| D101,242 S | 9/1936 | Poglein |
| D159,985 S | 9/1950 | Heisey |
| D172,090 S | 5/1954 | Pree |
| 2,830,721 A | 4/1958 | Pinsky et al. |
| D191,418 S | 9/1961 | Nassour |
| 3,043,464 A * | 7/1962 | Name Not Available ................. A61J 9/00 215/11.1 |
| D206,889 S | 2/1967 | Benes |
| D209,311 S | 11/1967 | Schilling et al. |
| 3,409,181 A * | 11/1968 | McDonnell ............ B65D 1/323 222/211 |
| D212,843 S | 12/1968 | Hart et al. |
| 3,432,177 A * | 3/1969 | Colwell ................. F02F 11/002 277/595 |
| 3,590,989 A | 7/1971 | Wittwer |
| D221,625 S | 8/1971 | Kinney et al. |
| D230,187 S | 1/1974 | Schultz |
| D242,200 S | 11/1976 | Ashton et al. |
| D243,406 S | 2/1977 | Mooney et al. |
| D251,650 S | 4/1979 | Heller |
| D252,373 S | 7/1979 | Eisenrod |
| D256,003 S | 7/1980 | Barr |
| D256,046 S * | 7/1980 | Perrin ......................... D23/269 |
| D258,202 S | 2/1981 | Astor et al. |
| D272,213 S | 1/1984 | Daenen |
| 4,540,721 A | 9/1985 | Staller |
| D288,902 S | 3/1987 | Lewis |
| 4,687,203 A | 8/1987 | Spector |
| 4,717,017 A | 1/1988 | Sprinkel et al. |
| D303,915 S | 10/1989 | Knutson |
| D312,768 S | 12/1990 | Eastman |
| 4,981,230 A | 1/1991 | Marshall et al. |
| D317,274 S | 6/1991 | Redina |
| D319,035 S | 8/1991 | Kruse |
| 5,165,603 A * | 11/1992 | Hahn ................. A45D 40/0068 239/55 |
| 5,197,620 A | 3/1993 | Gregory |
| 5,249,676 A | 10/1993 | Ashcraft et al. |
| D348,836 S | 7/1994 | McCallum et al. |
| 5,388,731 A | 2/1995 | Mengeu et al. |
| 5,477,640 A | 12/1995 | Holtkamp, Jr. |
| D367,818 S | 3/1996 | Zana |
| D372,765 S * | 8/1996 | Sisk ............................. D23/269 |
| D374,837 S | 10/1996 | Austin |
| 5,635,229 A * | 6/1997 | Ray ........................ B65D 23/12 206/205 |
| 5,707,696 A | 1/1998 | Boxler |
| D394,824 S | 6/1998 | Itzkowitz |
| 5,795,644 A * | 8/1998 | Delarosa .............. B65D 75/323 428/178 |
| 5,810,184 A | 9/1998 | Adams et al. |
| 5,858,141 A | 1/1999 | Repp et al. |
| 5,865,535 A | 2/1999 | Edwards |
| 5,913,437 A | 6/1999 | Ma |
| 5,954,247 A * | 9/1999 | Savine ....................... A45F 5/00 215/399 |
| 5,957,312 A | 9/1999 | Adams et al. |
| 6,006,472 A * | 12/1999 | Holtkamp, Jr. ......... A61L 9/127 47/79 |
| D422,905 S | 4/2000 | Walker |
| 6,045,833 A | 4/2000 | Landau |
| 6,062,441 A | 5/2000 | Mengeu et al. |
| 6,102,224 A * | 8/2000 | Sun ..................... B65D 41/3428 215/252 |
| 6,112,749 A | 9/2000 | Hall et al. |
| 6,112,923 A | 9/2000 | Ma |
| D438,050 S | 2/2001 | Huntzinger |
| 6,290,914 B1 | 9/2001 | LeJune et al. |
| D453,000 S | 1/2002 | Shinjo |
| D457,245 S | 5/2002 | Royal et al. |
| D457,783 S | 5/2002 | Bodum |
| D460,357 S | 7/2002 | Kras et al. |
| D465,731 S | 11/2002 | Brant et al. |
| 6,484,873 B1 * | 11/2002 | Pizarro .................... B65D 3/06 206/217 |
| 6,484,896 B2 | 11/2002 | Ma |
| 6,497,337 B1 | 12/2002 | Kehe |
| D468,492 S | 1/2003 | Wilhelm |
| 6,511,726 B1 | 1/2003 | Kinigakis |
| D470,057 S | 2/2003 | Bowen |
| 6,581,793 B1 | 6/2003 | Racine et al. |
| D476,893 S | 7/2003 | Pinnavaia |
| D477,225 S | 7/2003 | Pinnavaia |
| D482,562 S | 11/2003 | Demers |
| D482,794 S | 11/2003 | Whitley |
| D483,982 S | 12/2003 | Irvine |
| 6,659,297 B2 | 12/2003 | Gregory et al. |
| D485,126 S | 1/2004 | Watson |
| 6,677,397 B1 | 1/2004 | Baranowski et al. |
| D491,066 S | 6/2004 | Le Goff |
| 6,766,916 B2 | 7/2004 | Ma |
| D498,826 S | 11/2004 | Takahiro et al. |
| D501,625 S | 2/2005 | Biggerstaff |
| 6,964,346 B1 | 11/2005 | Taber et al. |
| D512,914 S | 12/2005 | Moretti |
| 6,981,602 B2 | 1/2006 | Ma et al. |
| D515,353 S | 2/2006 | Martin |
| 7,005,152 B2 * | 2/2006 | Landau ................. A47G 19/2227 426/106 |
| D518,717 S | 4/2006 | German |
| D518,718 S | 4/2006 | vonSpreckelsen et al. |
| D522,368 S | 6/2006 | Darr et al. |
| D533,747 S | 12/2006 | Jin |

(56) References Cited

U.S. PATENT DOCUMENTS

| | | | |
|---|---|---|---|
| D533,802 S | 12/2006 | Thompson et al. | |
| D534,428 S | 1/2007 | Reed et al. | |
| D534,802 S | 1/2007 | German | |
| D535,210 S | 1/2007 | Park | |
| D545,235 S | 6/2007 | Carter-Smith et al. | |
| D548,092 S | 8/2007 | Klemm | |
| D553,238 S * | 10/2007 | Haggkvist | D23/386 |
| D553,254 S | 10/2007 | Colin et al. | |
| 7,284,711 B2 | 10/2007 | Reed et al. | |
| 7,306,108 B2 | 12/2007 | Cleevely | |
| D564,711 S | 3/2008 | Modi et al. | |
| D565,253 S | 3/2008 | Modi et al. | |
| D576,047 S | 9/2008 | Reihle | |
| D578,889 S | 10/2008 | Sadiq et al. | |
| 7,470,035 B1 * | 12/2008 | Benitez | B65D 51/248 |
| | | | 362/101 |
| D584,149 S | 1/2009 | Lohrman et al. | |
| D587,118 S * | 2/2009 | Sadiq | D9/516 |
| 7,484,675 B2 | 2/2009 | Brown | |
| D591,603 S | 5/2009 | Robin-Prevallee | |
| D592,950 S | 5/2009 | Kopulos | |
| D593,858 S | 6/2009 | Kubicek et al. | |
| D595,581 S | 7/2009 | Brunson | |
| D598,238 S | 8/2009 | Durdon et al. | |
| D600,115 S * | 9/2009 | Trayser | D9/434 |
| D601,309 S | 9/2009 | Babal | |
| D602,651 S | 10/2009 | Modi et al. | |
| D606,864 S | 12/2009 | Robinson | |
| D611,814 S | 3/2010 | Marotti et al. | |
| D614,247 S | 4/2010 | Clausen | |
| D615,816 S | 5/2010 | Joy et al. | |
| D617,426 S | 6/2010 | Zeyfang | |
| D618,500 S | 6/2010 | Hardaway | |
| 7,748,557 B2 | 7/2010 | Robinson | |
| D623,056 S | 9/2010 | Sessa | |
| D623,460 S | 9/2010 | Krasner | |
| 7,798,320 B2 * | 9/2010 | Pham | B65D 65/42 |
| | | | 206/264 |
| D633,386 S | 3/2011 | Taber et al. | |
| D633,387 S | 3/2011 | Gatto | |
| D634,199 S | 3/2011 | Taber et al. | |
| D634,200 S | 3/2011 | Taber et al. | |
| D635,352 S | 4/2011 | Himley et al. | |
| D635,399 S | 4/2011 | Del Vecchio | |
| D637,448 S | 5/2011 | Cheng | |
| D643,912 S * | 8/2011 | Bowman | D23/269 |
| D646,568 S | 10/2011 | Heidel et al. | |
| D646,600 S | 10/2011 | Minkkinen et al. | |
| D650,677 S | 12/2011 | Wurster et al. | |
| D654,752 S | 2/2012 | Krasner | |
| D655,167 S | 3/2012 | Weber-Trinkfass et al. | |
| D657,675 S | 4/2012 | Averill | |
| D662,767 S | 7/2012 | Hotell et al. | |
| D666,461 S | 9/2012 | Siegel | |
| D671,406 S | 11/2012 | Sawicki et al. | |
| 8,364,028 B1 * | 1/2013 | Vaske | A61L 9/03 |
| | | | 219/385 |
| D678,989 S | 3/2013 | Zerrer | |
| 8,440,265 B2 * | 5/2013 | Duan | B32B 9/02 |
| | | | 427/379 |
| D684,065 S | 6/2013 | Wiseman | |
| D684,082 S | 6/2013 | Alvarez et al. | |
| D684,274 S | 6/2013 | Hosoya et al. | |
| D686,075 S | 7/2013 | Guerin et al. | |
| D686,101 S | 7/2013 | Dailey | |
| 8,474,637 B2 | 7/2013 | Zhang et al. | |
| D689,332 S | 9/2013 | Krasner | |
| D689,789 S | 9/2013 | Hardy | |
| D691,885 S | 10/2013 | Potts | |
| D693,645 S | 11/2013 | Keyes | |
| D694,107 S | 11/2013 | Didio | |
| D696,751 S * | 12/2013 | Beagen, Jr. | D23/269 |
| D696,952 S | 1/2014 | Sawicki et al. | |
| D697,805 S | 1/2014 | You | |
| 8,672,158 B2 | 3/2014 | Taber | |
| 8,708,189 B2 | 4/2014 | Reitzig | |
| D706,908 S | 6/2014 | Knapp | |
| D706,909 S | 6/2014 | van de Kipple et al. | |
| D715,092 S | 10/2014 | Thun et al. | |
| D723,919 S | 3/2015 | Taber et al. | |
| D724,386 S | 3/2015 | Royer et al. | |
| D725,953 S | 4/2015 | Gamelli et al. | |
| D730,734 S | 6/2015 | Rapparini | |
| D733,604 S | 7/2015 | Tan et al. | |
| D734,670 S | 7/2015 | Griffis | |
| 9,108,763 B2 * | 8/2015 | Landau | B65D 23/00 |
| D743,513 S | 11/2015 | Yamagishi et al. | |
| D744,846 S | 12/2015 | Koop et al. | |
| D752,378 S | 3/2016 | Wang | |
| D752,975 S | 4/2016 | Gatto | |
| D753,490 S * | 4/2016 | O'Donahue | D9/455 |
| 9,302,830 B2 | 4/2016 | Ramsey et al. | |
| D758,195 S | 6/2016 | Braz et al. | |
| D762,115 S | 7/2016 | Corvaglia et al. | |
| D766,716 S | 9/2016 | Logel et al. | |
| D776,529 S * | 1/2017 | Torrison | D9/435 |
| D783,607 S | 4/2017 | Lee et al. | |
| D785,144 S | 4/2017 | Kitagawa | |
| D791,591 S | 7/2017 | Berge | |
| D792,219 S | 7/2017 | Bueno Nunez | |
| D795,021 S | 8/2017 | Lindloff | |
| D796,901 S | 9/2017 | Pisarevsky | |
| D799,900 S | 10/2017 | Santos et al. | |
| D799,963 S | 10/2017 | Akiyama | |
| 9,801,969 B2 | 10/2017 | Griffis | |
| D804,305 S | 12/2017 | White | |
| D804,900 S | 12/2017 | Choe | |
| D804,906 S | 12/2017 | Diener et al. | |
| D807,173 S | 1/2018 | Cooper et al. | |
| D815,951 S | 4/2018 | Solovy | |
| D817,096 S | 5/2018 | Kauss et al. | |
| 9,957,076 B2 * | 5/2018 | Tung | B65D 1/0246 |
| D820,679 S | 6/2018 | Ali | |
| D821,150 S | 6/2018 | Liao | |
| D824,257 S | 7/2018 | Wood et al. | |
| D824,763 S | 8/2018 | Suess et al. | |
| D826,047 S | 8/2018 | Griffis | |
| D827,435 S | 9/2018 | Griffis | |
| D828,088 S | 9/2018 | Furneaux et al. | |
| D829,101 S | 9/2018 | Spivey et al. | |
| D830,773 S | 10/2018 | Jacobsen | |
| D832,130 S | 10/2018 | Bostic | |
| 10,086,104 B2 | 10/2018 | Griffis | |
| D832,734 S | 11/2018 | Warren | |
| D836,389 S | 12/2018 | Abante et al. | |
| D838,171 S | 1/2019 | Wood et al. | |
| 10,189,611 B2 | 1/2019 | Cox | |
| D839,673 S | 2/2019 | Meyers | |
| D842,030 S | 3/2019 | Meyers | |
| D848,844 S | 5/2019 | Byron et al. | |
| D851,996 S | 6/2019 | Umholtz | |
| 10,328,172 B2 | 6/2019 | Griffis | |
| D844,433 S | 7/2019 | Hall et al. | |
| D852,634 S | 7/2019 | Balletta et al. | |
| D855,464 S | 8/2019 | Hall et al. | |
| 2001/0027957 A1 | 10/2001 | Kano et al. | |
| 2002/0139093 A1 | 10/2002 | Landau | |
| 2002/0158037 A1 | 10/2002 | Kano et al. | |
| 2002/0190023 A1 * | 12/2002 | Landau | A47G 19/2227 |
| | | | 215/365 |
| 2003/0132244 A1 | 7/2003 | Birkmayer et al. | |
| 2004/0018278 A1 | 1/2004 | Popplewell | |
| 2004/0020890 A1 | 2/2004 | Tan et al. | |
| 2004/0029750 A1 | 2/2004 | Schudel et al. | |
| 2004/0262174 A1 | 12/2004 | Buesching et al. | |
| 2005/0196571 A1 * | 9/2005 | Penny, III | A61L 9/12 |
| | | | 428/40.1 |
| 2005/0274819 A1 | 12/2005 | Reed et al. | |
| 2006/0246265 A1 * | 11/2006 | Rogers | B41M 3/006 |
| | | | 428/195.1 |
| 2006/0255002 A1 | 11/2006 | Takamatsu et al. | |
| 2006/0278542 A1 * | 12/2006 | Pham | B65D 85/1045 |
| | | | 206/268 |

(56) References Cited

U.S. PATENT DOCUMENTS

| | | | |
|---|---|---|---|
| 2006/0278543 A1* | 12/2006 | Pham | B65D 65/42 206/271 |
| 2006/0291756 A1* | 12/2006 | Thomas | B32B 3/06 383/105 |
| 2007/0023301 A1* | 2/2007 | Pham | B65D 75/5844 206/264 |
| 2007/0051690 A1 | 3/2007 | Hidding | |
| 2007/0114142 A1 | 5/2007 | Sine et al. | |
| 2008/0067142 A1 | 3/2008 | Druitt | |
| 2008/0149586 A1 | 6/2008 | Loughrin et al. | |
| 2008/0173611 A1 | 7/2008 | Neputy et al. | |
| 2008/0245757 A1 | 10/2008 | Durand | |
| 2009/0045158 A1 | 2/2009 | Suriol | |
| 2009/0078786 A1 | 3/2009 | Slade | |
| 2009/0098026 A1* | 4/2009 | Wood | A61L 9/122 422/123 |
| 2009/0155505 A1* | 6/2009 | Wagenheim | A61L 9/127 428/34.2 |
| 2009/0258118 A1* | 10/2009 | Gillian | B65D 75/12 426/112 |
| 2010/0084362 A1 | 4/2010 | Letchinger et al. | |
| 2010/0323134 A1* | 12/2010 | Bostian | B32B 7/12 428/35.2 |
| 2011/0253584 A1 | 10/2011 | Duan | |
| 2011/0290755 A1 | 12/2011 | Taber et al. | |
| 2012/0006909 A1 | 1/2012 | Zhang et al. | |
| 2012/0175016 A1 | 7/2012 | Lopez et al. | |
| 2013/0015193 A1 | 1/2013 | Lien et al. | |
| 2013/0043245 A1 | 2/2013 | Griffis | |
| 2013/0056551 A1* | 3/2013 | Zhang | A23L 2/56 239/60 |
| 2013/0062239 A1* | 3/2013 | Key | B65D 23/14 206/459.1 |
| 2013/0105066 A1* | 5/2013 | Landau | B65D 23/00 156/85 |
| 2013/0119056 A1 | 5/2013 | Jacobson et al. | |
| 2013/0205718 A1 | 8/2013 | Kapolas | |
| 2013/0221007 A1 | 8/2013 | Jung et al. | |
| 2013/0276339 A1* | 10/2013 | Hernandez | G09F 3/02 40/311 |
| 2013/0313218 A1 | 11/2013 | Cox et al. | |
| 2014/0158660 A1 | 6/2014 | Wood et al. | |
| 2014/0263335 A1 | 9/2014 | Taber et al. | |
| 2015/0027974 A1 | 1/2015 | Niec | |
| 2015/0076030 A1* | 3/2015 | Smith | B65D 85/72 206/524.3 |
| 2015/0102033 A1 | 4/2015 | Banovie | |
| 2015/0305349 A1 | 10/2015 | Johnson et al. | |
| 2015/0329247 A1 | 11/2015 | Lou | |
| 2016/0106149 A1 | 4/2016 | Potter et al. | |
| 2016/0122066 A1 | 5/2016 | DiBaisio | |
| 2017/0081095 A1 | 3/2017 | McPherson et al. | |
| 2017/0239382 A1 | 8/2017 | Griffis | |
| 2017/0240325 A1 | 8/2017 | Seelhofer | |
| 2017/0275075 A1 | 9/2017 | Bamonte et al. | |
| 2017/0326263 A1 | 11/2017 | Griffis | |
| 2018/0043047 A1 | 2/2018 | Griffis | |
| 2018/0079552 A1 | 3/2018 | Ayeni | |
| 2018/0127159 A1 | 5/2018 | Cunningham | |
| 2018/0141730 A1 | 5/2018 | Rognard | |
| 2018/0201414 A1 | 7/2018 | Rouquette | |
| 2019/0009953 A1 | 1/2019 | Edie et al. | |
| 2019/0062007 A1 | 2/2019 | Kim | |
| 2019/0084728 A1 | 3/2019 | Bonfoey et al. | |
| 2019/0091363 A1 | 3/2019 | Griffis | |
| 2019/0118989 A1 | 4/2019 | Kim | |
| 2019/0367230 A1 | 12/2019 | Griffis | |

FOREIGN PATENT DOCUMENTS

| | | |
|---|---|---|
| DE | 202017001221 U1 | 7/2017 |
| GB | 5000214 | 10/2015 |
| WO | 2010068731 | 6/2010 |
| WO | 2018085580 | 5/2018 |
| WO | 2018203993 | 11/2018 |
| WO | 2019232431 | 12/2019 |

OTHER PUBLICATIONS

First Action Interview Pilot Program Pre-Interview Communication for U.S. Appl. No. 15/782,720, dated Apr. 2, 2018 (6 pages).

Flavour Bottle: The world's first flavored bottle, available at https://www.kickstarter.com/projects/flavourtechnologies/flavour-bottle-the-worlds-first-flavored-bottle/description.

Forever Gifts. Beveled Edge Black Tungsten Wedding Band. Apr. 26, 2017 [earliest online date], [site visited 04/26/18]. Available from Internet, <URL:https://www.forevergifts.com/beveled-edge-black-tungsten-wedding-band-free-engraving/>. (Year: 2017).

High-Tech Cocktail Glass Lets You Experience Plain Water as the Perfect Cocktail, Oddity Central, available at http://www.oddity central.com/technology/high-tech-cocktail-glass-lets-you-experience-plain-water-as-the-perfect-cocktail.html, Nov. 20, 2017.

International Search Report and Written Opinion for International Application No. PCT/US18/24630, dated Apr. 23, 2018 (7 pages).

Non-Final Office Action for U.S. Appl. No. 15/663,534, dated Apr. 2, 2018 (26 pages).

Non-Final Office Action for U.S. Appl. No. 29/598,882, dated May 1, 2018 (29 pages).

Non-Final Office Action for U.S. Appl. No. 29/598,879, dated May 1, 2018 (26 pages).

The New York Times. Mystery in Sochi Doping Case Lies With Tamper-Proof Bottle by Rebecca R. Ruiz. May 13, 2016 [earliest online date], [site visited Apr. 23, 2018]. Available from Internet, <URL:https://www.nytimes.com/2016/05/14/sports/russia-doping-bottles-olympics-2014.html>. (Year: 2016).

Examination Report received for European Union Design Application No. 005826559; dated Nov. 28, 2018 (2 pages).

First Examiner's Report received for Canadian Application No. 177508; dated Jul. 23, 2018 (3 pages).

Non-Final Office Action received for U.S. Appl. No. 15/663,534, dated Aug. 16, 2018 (26 pages).

First Examiner's Report received for Australian Application No. 2018202261; dated Aug. 30, 2018 (5 pages).

Office Action for German Application No. 10 2018 003 090.4, dated Jan. 15 2019 (8 pages).

Examiner's Report received for Canadian Application No. 2999583; dated Jan. 30, 2019 (3 pages).

Final Office Action received for U.S. Appl. No. 15/663,534; dated Feb. 13, 2019 (19 pages).

Non-Final Office Action received for U.S. Appl. No. 29/599,447, dated Mar. 28, 2019 (10 pages).

Szent Water: Announced Nov. 7, 2018 [online]. Site visited [Mar. 22, 2019]. Available from internet URL: https://www.amazon.com/SZENT-Water-Passionfruit-Ounce-Pack/dp/B07G8 LH B F2/ref=cm_cr_arp d_product_top?ie=UTF8&th = 1.

Notice of Allowance Received for U.S. Appl. No. 15/663,534, dated May 3, 2019.

Notification to Grant Patent Right for Design and Go through Formalities of Registration Received for Chinese Application No. 201830652933.8 dated Jul. 16, 2019.

International Search Report and Written Opinion for International Application No. PCT/US19/24708, dated Jun. 24, 2019 (9 pages).

Notice of Acceptance for Patent Application Received for Australia Application No. 2018202261, dated May 30, 2019.

Amazon. Szent Water Passionfruit Ounce Pack. Review by Brett Conway on Nov. 9, 2018. hhtps://www.amazon.com/SZENT-Water-Passionfruit-Ounce-Pack/dp/B07G8LHBF2?th=1(Year: 2018).

Amazon. Oxford Ivy—Men's 14K White Gold 6MM Comfort Fit Beveled Edge Wedding Band Sep. 30, 2016. https://www.amazon.com/White-Comfort-Beveled-Wedding-Available/dp/B01LYD52N4 (Year: 2016).

Final Office Action received for U.S. Appl. No. 29/599,447, dated Oct. 10, 2019 (26 pages).

Examination Report received for GB 1904947.7; dated Sep. 3, 2019 (2 pages).

(56) References Cited

OTHER PUBLICATIONS

Examination Report received for Canadian Design Application No. 184681; dated Oct. 8, 2019 (44 pages).
Final Office Action received for U.S. Appl. No. 29/599,450; dated Dec. 11, 2019 (17 pages).
Non-Final Office Action received for U.S. Appl. No. 29/650,568; dated Dec. 19, 2019 (7 pages).
Non-Final Office Action received for U.S. Appl. No. 29/650,571; dated Dec. 19, 2019 (10 pages).

* cited by examiner

US 10,744,223 B2

SCENTED MATERIAL COMPOSITIONS AND ARTICLES FOR USE WITH FOOD AND BEVERAGE

CROSS-REFERENCE TO RELATED APPLICATIONS

This patent document claims priorities to and benefits of U.S. Provisional Patent Application No. 62/649,215 entitled "SCENTED MATERIAL COMPOSITIONS AND ARTICLES FOR USE WITH FOOD AND BEVERAGE" filed on Mar. 28, 2018, and also claims priorities to and benefits of and is a continuation-in-part of U.S. patent application Ser. No. 16/136,664 entitled "SCENTED ATTACHMENT FOR CONTAINERS" and filed on Sep. 20, 2018, which is a continuation of U.S. patent application Ser. No. 15/782,720 entitled "SCENTED ATTACHMENT FOR CONTAINERS" and filed on Oct. 12, 2017, now U.S. Pat. No. 10,086,104, which is a continuation of U.S. patent application Ser. No. 15/588,571 entitled "SCENTED ATTACHMENT FOR CONTAINERS" and filed on May 5, 2017, now U.S. Pat. No. 9,801,969, which is a continuation-in-part of U.S. patent application Ser. No. 13/429,300 entitled "SCENTED ATTACHMENT FOR CONTAINERS" and filed on Mar. 23, 2012, which claims the benefits and priority of U.S. Provisional Patent Application No. 61/467,888, entitled "SCENTED ATTACHMENT FOR CONTAINERS", which was filed on Mar. 25, 2011. The entire contents of the aforementioned patent applications are incorporated by reference as part of the disclosure of this application.

TECHNICAL FIELD

This patent document relates to scented material compositions and articles for use with food and beverage, including methods and equipment for their manufacture, and, in particular, scented articles for a scented bottle cap system having a scented attachment for enhancing a user's sense of smell and/or taste.

BACKGROUND

The nasal cavity has specialized sensory cells that mediate olfaction. The main olfactory system of humans and animals detects volatile chemicals, and the accessory olfactory system detects fluid-phase chemicals. Olfaction like taste is a form of chemoreception. The chemicals that activate the olfactory system, generally at very low concentrations, are called odorants. Accordingly, there is a commonality between the perception of smell and the perception of taste. In fact, in certain instances, the sense of smell may supplement and/or otherwise enhance the sense of taste. For instance, it is well known that maladies affecting the sense of smell adversely affect the sense of taste. As taste plays an important role in ones motivation for consuming a food or drink article, there is an interest in the art for agents that enhance the perception of taste of food and drink articles. The present disclosure addresses these and other such needs.

SUMMARY

Aspects of the disclosure include an attachment for providing a scent to a container. In certain instances, the scented attachment is configured for being associated with a container, such as a drink or a food storage container. The scented attachment may be associated with the container in any suitable manner. In some instances, the scented attachment is of a size or shape so as to fit around a circumference of the container. Thus, the scented attachment may be a sleeve, a wrap, a ring, or the like. In another instance, the scented attachment may be configured for being associated to the container with a suitable attachment mechanism. For instance, the scented attachment may include a substrate having a first and a second surface. The first surface comprises an attachment mechanism for associating the scented attachment to the container; and a second surface comprises a scent. In such a manner, a scented agent may be associated with a food or drink container so as to enhance the perception of the taste of the food or drink contained therein, thereby, enhancing the experience and/or ones motivation in eating or drinking. Also provided is a method for its use and a system for providing a scent to a container that includes a scented attachment, as described herein, and a container that is configured for being associated with the container.

In some aspects, a scent delivery system for a beverage container includes a bottle to contain a fluid beverage, the bottle structured to include a body region and a neck region, the bottle including a collar that extends outward and circumferentially around the neck region, and a ledge structure that extends outward and circumferentially around the neck region and is positioned above the collar; a scent ring including a body loaded with a volatile chemical agent to emanate from the body of the scent ring to generate a scent, the scent ring structured to include at least one interior protruding structure that projects from an interior wall of the body of the scent ring, in which the scent ring is configured to fasten around the neck region of the bottle based on contact between the at least one interior protruding structure of the scent ring and the ledge structure of the bottle, in which the at least one interior protruding structure is positioned below the ledge structure; and a cap reversibly attachable to the bottle, the cap including an interior rim structure that projects from and circumferentially around an interior cap wall of the cap, in which the cap is structured to enclose the scent ring in a compartment formed between the collar of the bottle and the interior rim structure of the cap when the cap is securely fastened to the bottle, in which the system is configured to trap the scent from the scent ring in the compartment when the cap is securely attached to the bottle and to release the scent into an outer environment of the bottle when the cap is detached from the bottle.

In some aspects, a scented attachment for a beverage container includes a scented article having a body that comprises a scented material including a plastic material loaded with a volatile chemical compound to emanate from the body of the scented article to generate a scent, in which the scented article includes at least one interior protruding structure that projects from an interior wall of the body of the scented article and is configured to attach to a bottle, in which the scented article is produced by a process comprising: selecting a loading parameter of a fragrance oil with respect to a plastic base material to manufacture the scented material, in which the loading parameter includes a % concentration of the scented material in a range of 1% to 30%; melting the plastic base material in a chamber including mechanically processing the base material to cause the plastic base material to change from a solid phase to a liquid phase or liquid-like phase at a particular viscosity; mixing an amount of the fragrance oil in accordance with the selected loading parameter with the melted base material at a predetermined temperature and pressure in the chamber to form an intermediary scented material; extruding the intermediary scented material through holes of an extrusion plate to form an extruded intermediary scented material; modifying the extruded intermediary scented material to form scented particles; cooling the scented particles in a fluid bath that prevents exposure of the scented particles to air; drying the cooled scented particles without applying heat to produce the scented material; and producing the scented article by molding the scented particles to a shape of the scented article.

BRIEF DESCRIPTION OF THE DRAWINGS

According to common practice, the various features of the drawings may not be drawn to-scale. Rather, the dimensions of the various features may be arbitrarily expanded or reduced for clarity. Included in the drawings are the following figures:

FIGS. 1A and 1B illustrate instances of a scented ring in accordance with the disclosure, in which FIG. 1A represents one instance of the scented ring, and FIG. 1B represents another instance of the scented ring.

FIGS. 2A and 2B illustrate instances of a scented strip in accordance with the disclosure, in which FIG. 2A illustrates a scented strip having a main body and a removable portion with a scented portion within the main body, and FIG. 2B illustrates an instance of a scented strip having a removable portion that is configured for detachably interacting with a lid of the container.

Figure 1A:
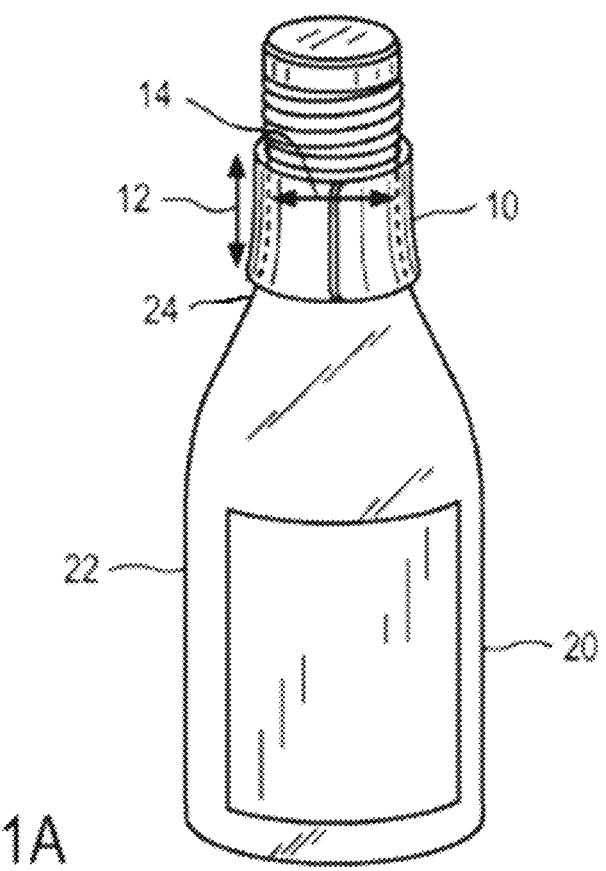

Before the present disclosure is further described, it is to be understood that this disclosure is not limited to particular instances described, as such may of course vary. It is also to be understood that the terminology used herein is for the purpose of describing particular instances only, and is not intended to be limiting. Unless defined otherwise, all technical and scientific terms used herein have the same meaning as commonly understood by one skilled in the art to which this invention belongs.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Throughout this application, various publications, patents and published patent applications may be cited. The disclosures of these publications, patents and published patent applications referenced in this application are hereby incorporated by reference in their entirety into the present disclosure. Citation herein of a publication, patent, or published patent application is not an admission of said publication, patent, or published patent application as prior art.

It must be noted that as used herein and in the appended claims, the singular forms "a", "and", and "the" include plural referents unless the context clearly dictates otherwise. Thus, for example, reference to an "opening" may include a plurality of such openings, and reference to "the gripping element" includes reference to one or more gripping elements and equivalents thereof known to those skilled in the art, and so forth. It is further noted that the claims may be drafted to exclude any optional element. As such, this statement is intended to serve as antecedent basis for use of such exclusive terminology as "solely", "only" and the like, in connection with the recitation of claim elements, or the use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

DETAILED DESCRIPTION

Aspects of the disclosure include an attachment for providing a scent to a container. In certain instances, the attachment is a ring or a sticker that is configured for removable association with a container, such as a food or a drink container. In some instances, the ring is configured for wrapping around a portion of the container. In another instance, the sticker is configured for being removably stuck onto a portion of the container. The attachment is configured such that during use of the container having the scented attachment, a subjects' olfactory system is activated by the scent of the attachment, which thereby enhances the sensation, e.g., the perception of taste, of eating or drinking the food or drink item that is contained within the container.

In some instances, the ring includes a circular body with a lumen, wherein the body is configured for being removably associated with a container. For instance, the scented ring includes a stretchable body that is adapted for being fit over a portion of the container. In certain embodiments, the body of the ring is comprised of an elastic material that deforms in a manner such that the diameter of the ring may increase when a stretching force is applied to the ring and/or return to its normal state once the stretching force has been removed. In a manner such as this, the ring may be fit over a portion of the container, such as a neck of a bottle, so as to enhance the perception of consuming the item contained within the container.

In another instance, the attachment may be configured as a sticking element and may include a substrate having a first and a second surface. The first surface may include an attachment mechanism for associating the scented attachment to the container; and a second surface comprises a scent. The attachment surface may include an adhesive or other attachment mechanism, such that it may adhere to a surface of the container. The scented surface may include a matrix configured for releasably holding a scent that may be released there form during the use of the container.

The subject scented attachments of the disclosure will be described first, followed by a description of the methods of their use and the systems in which such scented attachments may be employed. A discussion of representative uses of the subject materials is also presented.

Scented Attachments, Systems and Methods of Use

Figure 1B:
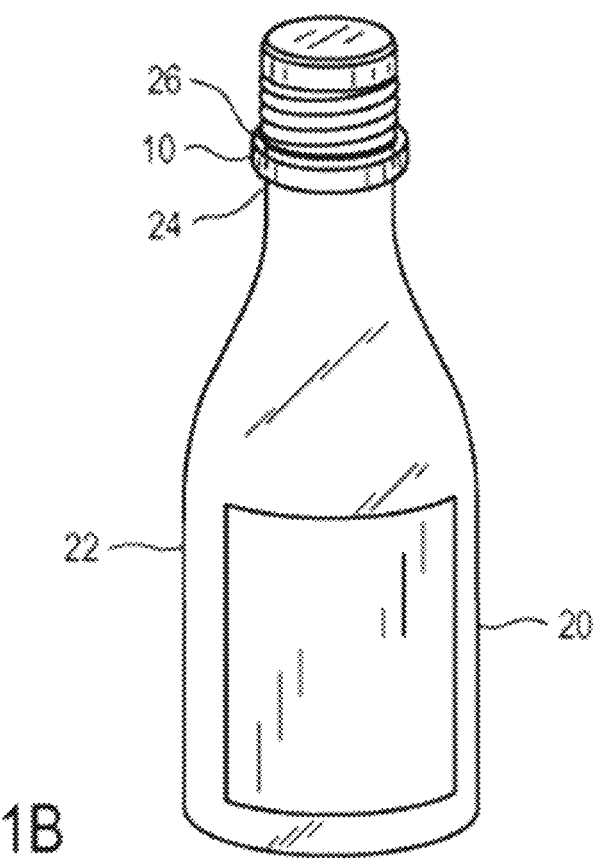

As can be seen with respect to FIGS. 1A and 1B, the disclosure provides an attachment for providing a scent to an object, such as a container. In some instances, the attachment 10 is a ring that is configured for providing a scent to a container, e.g., a food or drink container 20. By "scent" is meant any agent that is capable of being incorporated within the attachment, being released there from, and stimulating an olfactory sensation of a subject.

For instance, in certain instances, a scent may be a chemical agent that stimulates a chemoreceptor of the olfactory system of the subject or otherwise stimulates sense of smell and/or taste of a subject. For example, in certain instances, a scent may be a volatile compound or odorant, such as a fragrant or other essential oil. Where the scent is a fragrant oil, it may be a food derived oil such as a citrus oil, a mint oil, anise oil, cardamom oil, cinnamon oil, clove oil, coriander oil, *eucalyptus* oil, fennel oil, lemongrass oil, and/or a nutmeg oil, and the like. The scent may be a citrus oil such as a lemon oil, a lime oil, a neroli oil, and/or an orange oil, and the like. In certain instances, scent comprises a mint oil such as a peppermint oil and/or spearmint oil, and the like.

The scented essential oil may be incorporated within the attachment in any suitable manner. For instance, the attachment may include a matrix within which the essential oil may be incorporated. The matrix may include a liquid or a gel, which may include the scent. The liquid or gel may be associated with the material employed to fabricate the attachment. For example, the attachment may be constructed in any suitable manner and may be fabricated from any suitable material. In certain instances, a suitable material may be one or more of an elastic material, a foamed or vulcanized rubber, neoprene, polyurethane, nylon, lycra, plastic, silicone, and/or a silicone containing material. Hence, the material from which the attachment is produced may be fabricated into a ring or sheet and compression or liquid injection molded into a protective device in accordance with some embodiments of the disclosure.

For instance, the body of the attachment may be fabricated using compression molding, during which process an element containing an essential oil is added thereto either during or after the molding process. Additionally, a colorant or other chemical additive may be added to the sheet blanks, which become the compression molded end product, for instance, to color and/or to aid in the release of the product from the mold. In certain instances, the attachment is made from a single piece of shaped or otherwise molded material and may include a cavity into which a scented material, e.g., a gel or substrate containing an essential oil associated therewith is injected or otherwise inserted into the lumen of the scented attachment. The main body of the attachment may comprise elastic properties, such that the attachment can deform to receive a portion of a container, e.g., a neck thereof, and then reform to its original configuration automatically, that is without the need for external manipulation. In certain instances, the attachment may include a main body that is pre-formed into a substrate onto one surface of which a gel or other matrix containing a scented agent, e.g., an essential oil, is added; and to an opposing surface, a suitable attachment mechanism, e.g., an adhesive, is added. One or more removable covers may be added to cover one or more of the scented surface and/or the attachment surface.

The attachment can be made into any desired shape such as a tube, a square or rectangular box, a triangular, pyramidal or circular shape, or the like. And thus the attachment may be configured for fitting around suitable container, such as a round, circular, triangular, square, rectangular, cube shaped container, or the like, and may be of regular or irregular dimensions, so as to fit a variety of bottles, jars, and the like. In certain instances, a scented attachment such as attachment 10 shown in FIGS. 1A and 1B and the material from which it is fabricated is hygienic, light weight and flexible such that the material is capable of expanding so as to allow the attachment to expand around the contours of the container 20 to be received thereon and snuggly fits around the container 20, and yet be configured for returning to its original configuration once the container 20 has been removed from the attachment.

Accordingly, the attachment 10 may be of any suitable size and shape, but is typically of a size and shape so as to be non-obstructively associated with the container 20. The container 20 may be any container such as a container for storing a beverage or other food article. The container 20 may be of any size or any shape, but is typically of a size and a shape suitable for containing a drink or food product, such as a drink or food product that is meant to be readily consumed by a subject. For instance, the container 20 may be a plastic or glass container, a metal or metal alloy container, or the like. If the container 20 is made of glass, the glass may be of any suitable type of glass, such as silicon dioxide, sodalime glass, pyrex, lead crystal, and the like. If the container 20 is made of metal, the metal may be of any suitable type of metal, such as aluminum, steel (e.g., stainless steel), tin, and the like. The container 20 for use in accordance with various embodiments of the scented attachment disclosed herein may also include alloys of any suitable metals. The container 20 may also be a plastic container, such as a TUPPERWARE® or RUBBERMAID® or GLAD® container.

The container 20 may contain any material, such as a solid, liquid, or gas. In certain instances, the container 20 is a fluid container that contains a liquid. The liquid within the container may be any form of liquid. In certain embodiments, the liquid is a liquid that is meant to be imbibed. For instance, in certain embodiments, the liquid is a liquid such as, water, soda, a liquid nutrient, a juice, an electrolyte, a sports drink, an alcoholic beverage, and the like. In certain embodiments, the container 20 is a solid object container, for instance, a food container that contains a solid food. For example, the attachment may be configured for being associated with a bottle, a can, a thermos, a camel back container, a canteen, or other such drinking container. In certain instances, the container may be a food container, such as a container for the storage of a food.

The attachment 10 may be associated with the container 20 in any suitable manner. In some instances, the attachment 10 is of a size or shape so as to fit around a circumference of the container 20. Thus, the attachment 10 may be a ring, sleeve, wrap, or the like that has been fabricated in such a manner so as to include a scent therein. For instance, in certain instances, the attachment 10 may be a ring that may be flat or tubular and may include an opening through which a container may be inserted. Accordingly, in certain instances, the ring attachment may be of a size and a shape so as to fit around a portion, e.g., the neck, of a drinking container. The ring, therefore, may have a diameter such that it can slip onto and/or around the neck of a bottle, but not slide down the length of the bottle.

As described above, the attachment 10 may be made of any suitable material, but in certain instances, it is made of a material that is capable of stretching, and thus the diameter of the ring may be configured for moving from a first, smaller diameter to a second, larger diameter when stretched, and/or for returning from the second stretched diameter toward the first, non-stretched diameter in the absence of a suitable stretching force. In a manner such as this the attachment 10 such as the ring embodiments may be configured for fitting snuggly around a portion of the container 20, e.g., the neck, the middle, and/or bottom of the container.

As illustrated in FIG. 1A, the scented attachment 10 can be structured as a ring and may be fabricated as single piece from a unitary material. The material may have a length 14 the matches its width 12, a length 14 less than its width 12, or a length 14 that is greater than its width 12. For instance, in certain embodiments, the length 14 may be in a range from about 2 or 3 mm or less to about 20 cm or more, such as about 5 or 10 mm to about 12 or 15 cm, including about 2 or 5 cm to about 8 to about 10 cm. In certain instances of the attachment 10 structured as a ring, the ring includes a circumference and the length 14 is measured from one point of a circumference moving in a single direction away from and back to that same point on the circumference. In certain embodiments, for example, dependent on the material from which the ring is made, the length 14 may increase as the material stretches. The width 12 of the material may correspond to that of the length 14 but typically may range from about 2 or 3 mm or less to about 15 cm or more, such as from about 5 or 10 mm to about 12 or 14 cm, including about 2 or 5 cm to about 8 to about 10 cm. The thickness of the material may range from about 1 mm or less to about 10 mm or more, such as from about 2 or 3 mm to about 8 or 9 mm, including from about 4 or 5 mm to about 6 or 7 mm.

In certain instances of the attachment 10 structured as a ring, as shown in FIG. 1A, the attachment ring may be dimensioned to cover a substantial portion of the neck 24 of a container 20, e.g., a bottle, while leaving the main body 22 uncovered. For instance, where an attachment ring is provided so as to generate a scent detectable by a subject using the container, it may be useful to have an attachment ring that does not cover the entire or even a substantial portion of the body 22 of the container 20, e.g., as this will be less expensive to produce and better for the environment. Accordingly, in some instances, the attachment ring covers all of the neck of the bottle, a top half of the neck of the bottle, or a bottom half of the neck of the bottle. As can be seen with respect to FIG. 1B, in some instances, the scented attachment ring 10 is dimensioned to fit around a top portion 26 of the neck 24 of the container 20. In this example implementation, the scented attachment ring 10 is configured for covering only the top portion 26 of the neck 24 of the container 20 (e.g., bottle) so as to provide a scent to a person, for instance, while drinking from the container 20.

Figure 2A:
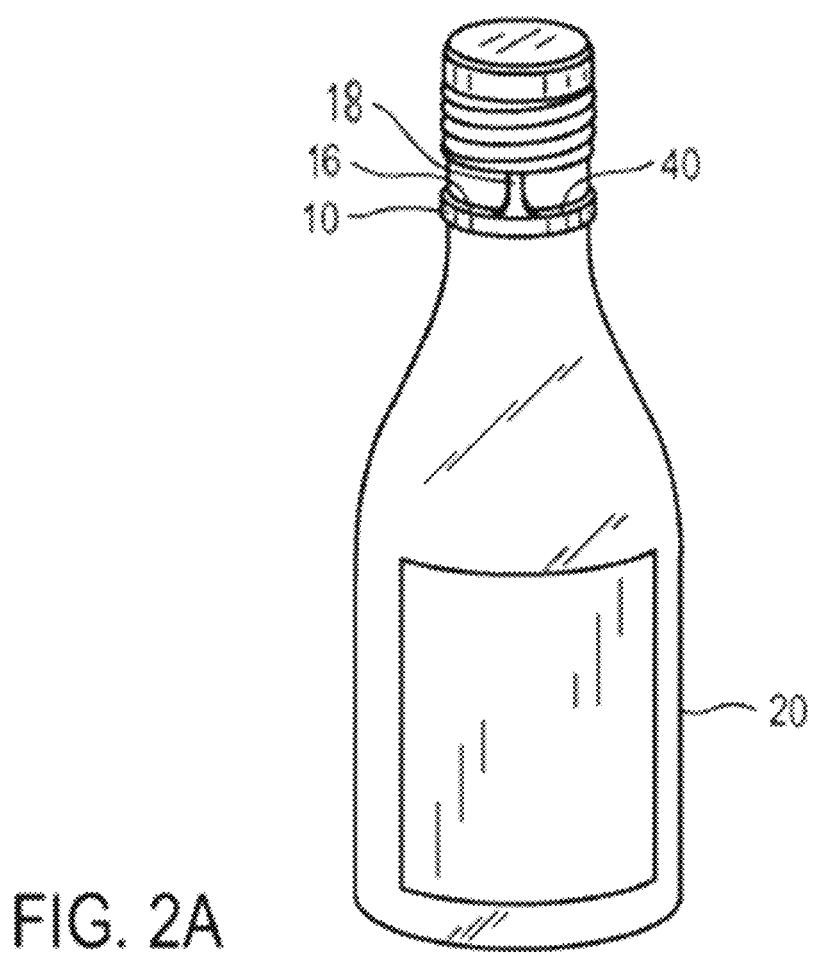

FIG. 2A represents another instance of a scented attachment in accordance with embodiments of the disclosure. The attachment 10 includes a main body 16 and a removable portion 18. The main body 16 of the attachment 10 may be configured for encasing a scented strip 40 therein. The scented strip 40 includes a scented agent, e.g., an essential oil, that is associated there with. The removable portion 18 may be removed from the main body 16 of the attachment 10 and thereby release the stored scent encased therein. The removable portion 18 may be associated with a lid of the container or otherwise removable. For example, when the lid is removed, the removable portion 18 is separated from the main body 16 of the attachment 10, and the scent from scented strip 40 is thereby released. In this configuration, the removable portion 18 may be a tab that may be pulled off by a user prior to drinking, or may be associated with the lid in such a manner that as the lid is removed the tab is removed.

Figure 2B:
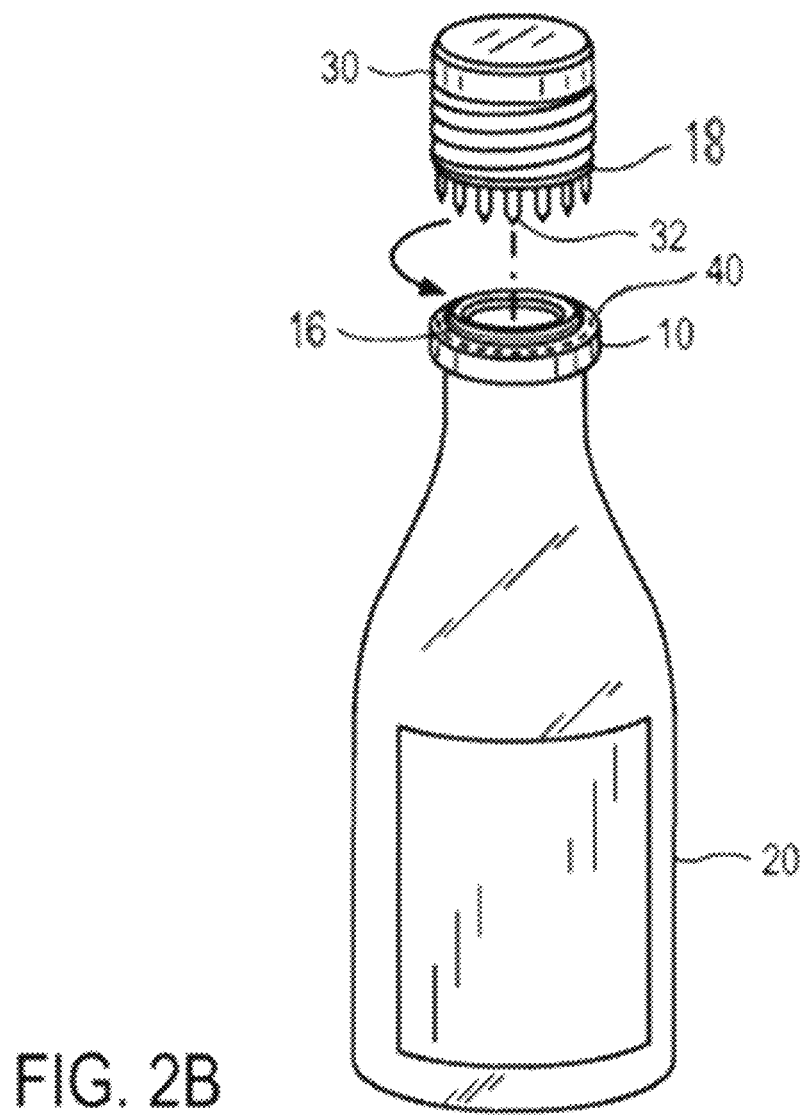

For instance, as seen with reference to FIG. 2B, the removable portion 18 may be associated with a lid 30 in such a manner that as the lid is removed the removable portion 18 is disassociated from the main body 16 of the attachment 10. For example, the lid 30 may be configured such that by twisting it relative to the container 20 it may be removed from the container 20, and likewise, the scented attachment 10 may be configured such that as the lid 30 twists, the removable portion 18 also twist relative to the main body 16 along with the lid 30. Thus, as the lid 30 is removed, so is the removable portion 18 and the scented strip 40 is exposed, thereby releasing the scent. In some instances, the lid 30 may include teeth 32 which are associated with the main body 16 and the removable portion 18, such that as the lid 30 is removed the teeth 32 separate from the main body 16 causing the removable portion 18 to be removed from the main body 16.

Figure 3A:
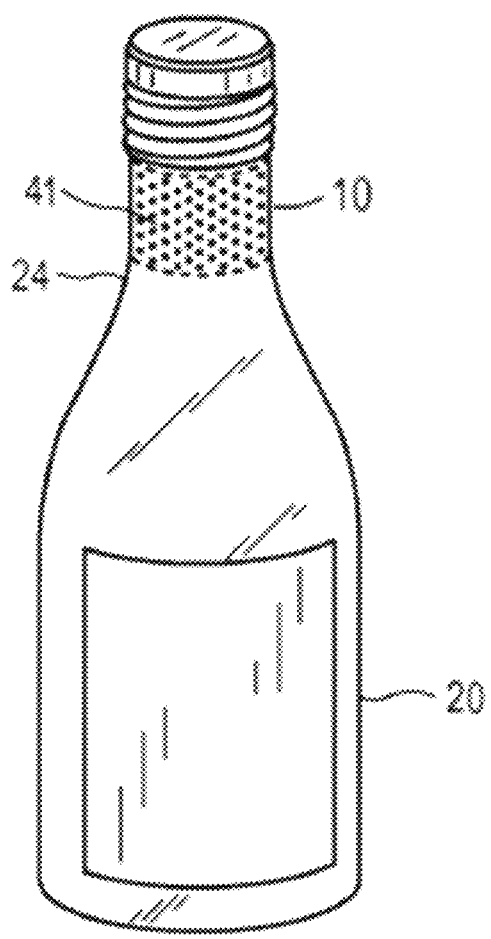
FIG. 3A illustrates another instance of a scented attachment where the scent is integrated into at least a portion of the container.

In certain instances, as with reference to FIG. 3A, the scented attachment 10 may actually be incorporated into the material of the container 20 so as to form a scented area 41. The scented area 41 may be formulated by incorporating an essential oil into the container 20 at an area near the neck 24 of the container 20. A removable cover (not shown) may be placed over the scented area 41 so as to lock in the scent until use. For instance, a user may remove the cover from the scented area 41 prior to opening the container 20 and consuming the drink or food therein.

Figure 3B:
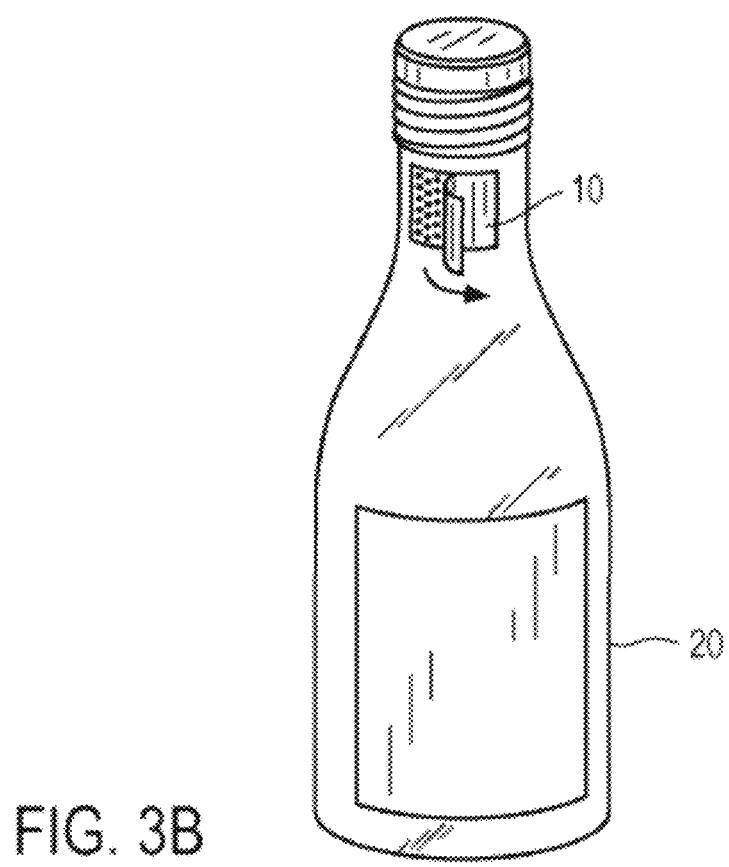
FIG. 3B illustrates another instance of a scented attachment.

FIG. 3B illustrates an instance of a scented attachment 10 wherein the attachment is configured for being associated to the container 20 with a suitable attachment mechanism. For instance, the attachment 10 may include a substrate having a first and a second surface. The first surface comprises an attachment mechanism for associating the scented attachment 10 to the container 20; and a second surface comprises a scent, e.g. an essential oil. The attachment mechanism may be a suitable adhesive, a snap and button configuration, a hook and loop fastener attachment (e.g., Velcro™), and the like. The adhesive may be used to associate the scented attachment 10 to the container 20. Alternatively, a Velcro™ strip may be used to attach the attachment 10 to the container 20. In such a manner the scented attachment 10 may be removable from the container 20. Further, the scented attachment 10 may be a separate element from the container 20, made to be separately obtained and attached thereto, or may be pre-attached to the container 20.

Figure 4:
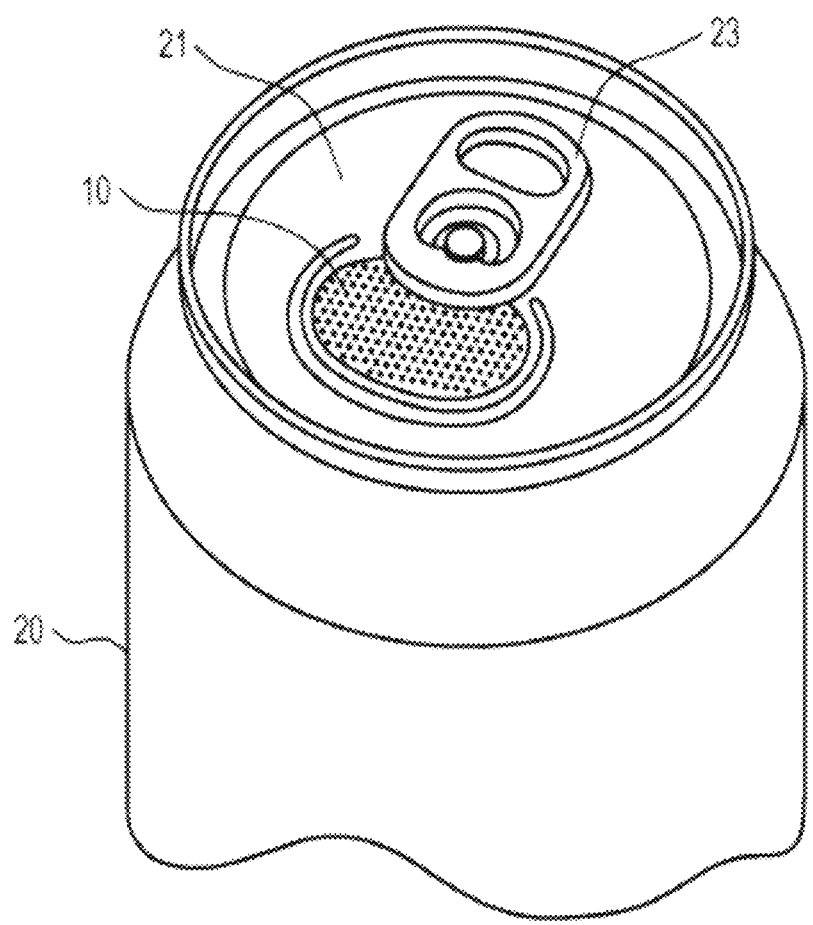
FIG. 4 illustrates another instance of a scented attachment of FIG. 3B.

FIG. 4 illustrates an instance of a scented attachment for a container 20 that is configured as a can. In some instances, the scented attachment 10 is positioned on a top portion 21 of the can 20 next to the opening mechanism 23. The scented attachment 10 may be previously associated to the can 20 or may be a separate element that is obtained and attached to the can, such as immediately prior to use of the can. The scented attachment 10 may be configured such and associated with the opening mechanism 23 of the can 20 such that by opening the can the scent is released by the attachment 10.

Figure 5:
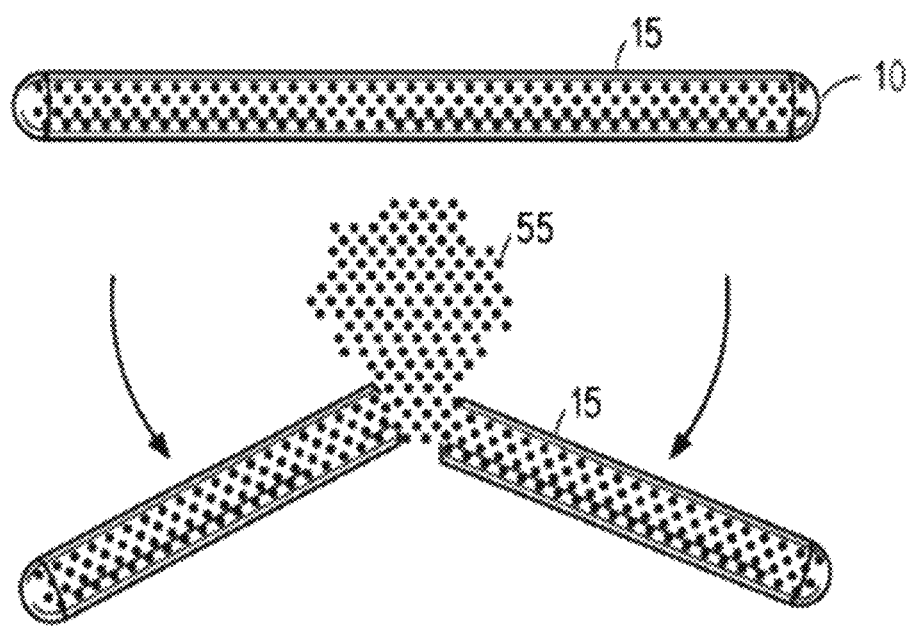
FIG. 5 illustrates a scented capsule.

FIG. 5 illustrates a scented attachment for a scented capsule, in which the attachment 10 includes a main body 15 and a scented material 55 therein. The main body 15 may be such that when cracked one or more pores forms and the scent 55 is released there from.

In some aspects in accordance with the present technology, the scented articles, apparatuses and systems are directed to a protective sleeve system. In certain embodiments, for example, the protective sleeve system is configured for both holding and protecting a held container. Accordingly, in certain embodiments, the protective sleeve system includes a protective sleeve (such as described above), which includes a tubular body, configured for holding a container, and at least a first opening, adapted for receiving the container, and in addition to the protective sleeve, the protective sleeve system may include a suitable container, such as those described above, for instance, a bottle, can, or other food storage element that is adapted to be fit and/or held within the protective sleeve.

For instance, in certain instances, the scented attachment may be included in a system that includes a suitable container, such as a glass or plastic bottle. For example, the container may be a water or sports drink bottle, or the like. The attachment may be previously associated with the bottle or may be a separate element that is meant to be attached to the container by the user of the container prior to use. The attachment may be a substrate having a scented surface having a cover thereon and may include an adhesive surface additionally having a cover thereon. The cover over the adhesive may be removed and the substrate associated with the container by the user. The cover covering the scented surface may then be removed by the user prior to consuming the drink or food item therein. In an alternative embodiment, the attachment may be a ring that is configured for being slid over an end of the container and associated thereby with the container, for instance, a neck of the container, e.g., by a user.

Examples of the scented attachment for containers include the following.

In some embodiments of the scented attachment (example A1), a scented attachment for association with a container comprises a substrate having first and second surfaces, the first surface comprises an attachment mechanism for associating the scented attachment to the container; and the second surface comprises a scent.

Example A2 includes the scented attachment of example A1, further comprising a third surface, wherein the third surface detachably covers the second surface thereby preventing the scent from being released when the third surface covers the second surface.

Example A3 includes the scented attachment of example A1, wherein the second surface comprises a matrix which matrix comprises the scent.

Example A4 includes the scented attachment of example A3, wherein the matrix comprises a gel, which gel comprises the scent.

Example A5 includes the scented attachment of example A4, wherein scent comprises a fragrant oil.

Example A6 includes the scented attachment of example A5, wherein the fragrant oil comprises a citrus oil, a mint oil, anise oil, cardamom oil, cinnamon oil, clove oil, coriander oil, *eucalyptus* oil, fennel oil, lemongrass oil, and nutmeg oil.

Example A7 includes the scented attachment of example A6, wherein the citrus oil comprises an oil selected from the group consisting of a lemon oil, a lime oil, a neroli oil, and orange oil.

Example A8 includes the scented attachment of example A6, wherein the mint oil comprises an oil selected from the group consisting of peppermint oil and spearmint oil.

Example A9 includes the scented attachment of example A1, wherein the substrate comprises a ring having an opening configured for receiving a portion of a bottle therein.

Example A10 includes the scented attachment of example A9, wherein the ring is removably associated with a lid which lid is configured for being sealably associated with a bottle.

Example A11 includes the scented attachment of example A10, wherein when the lid is removed from the bottle the lid detaches from the ring thereby releasing the scent.

Example A12 includes the scented attachment of example A11, wherein the ring comprises silicon.

Example A13 includes the scented attachment of example A11, wherein the ring comprises elastic.

Example A14 includes the scented attachment of example A13, wherein the ring comprises one or more identifying colors.

Example A15 includes the scented attachment of example A1, wherein said attachment element comprises one or more of an adhesive or a loop and hook attachment.

Example A16 includes the scented attachment of example A11, wherein the scent is encapsulated within a burstable seal.

Example A17 includes the scented attachment of example A16, wherein the scent is released when the seal is burst.

Example A18 includes the scented attachment of example A1, wherein the scented attachment is associated with a can.

Example A19 includes the scented attachment of example A18, wherein the scented attachment releases a scent when the can is opened.

In some embodiments of the scented attachment (example A20), a container comprises a body for holding matter, the body being enclosed on all sides except an opening; a scented attachment provided on the body near the opening; and a cap that removably covers the opening.

Scented Bottle Cap Systems and Methods of Fabrication and Use

In some aspects of the scented attachment in accordance with embodiments of the present technology, a scented bottle cap system includes a scented ring attachable to a bottle, e.g., disposed around the neck of the bottle, and a cap removably attachable to the bottle and configured to enclose the scented ring in a hollow region between the cap and the bottle when the cap is securely attached to the bottle, such that the scented bottle cap system entraps a scent from the scented ring in the hollow region when the cap is securely attached to the bottle and controllably releases the scent into the proximate environment of the bottle when the cap is removably detached from the bottle. In implementations of the scented bottle cap system, for example, the scent can include one or more chemical agents in a volatile compound or aggregate that provides a pleasing odorant to the user of the scented bottle cap system that stimulates a corresponding chemoreceptor of the user's olfactory system to enhance the user's sense of smell and/or taste of a drinkable fluid in the bottle. For example, the odorous compound or aggregate can include an oil, a liquid or gel (e.g., carried in a matrix), or a resin or powder. In various embodiments, the scented ring can contain the scent by various methods, including incorporating the scent into the material of the ring, e.g., during a fabrication process to produce the ring. In some embodiments, for example, the scented ring can be fabricated using a plastic material, e.g., polyethylene, polyurethane or other example materials described herein, that is loaded with the odorous compound or aggregate that produces the scent to a desired concentration, e.g., which can be selected based on multiple variables including the type of scent (e.g., degree of pungency of a particular scent).

Figure 6:
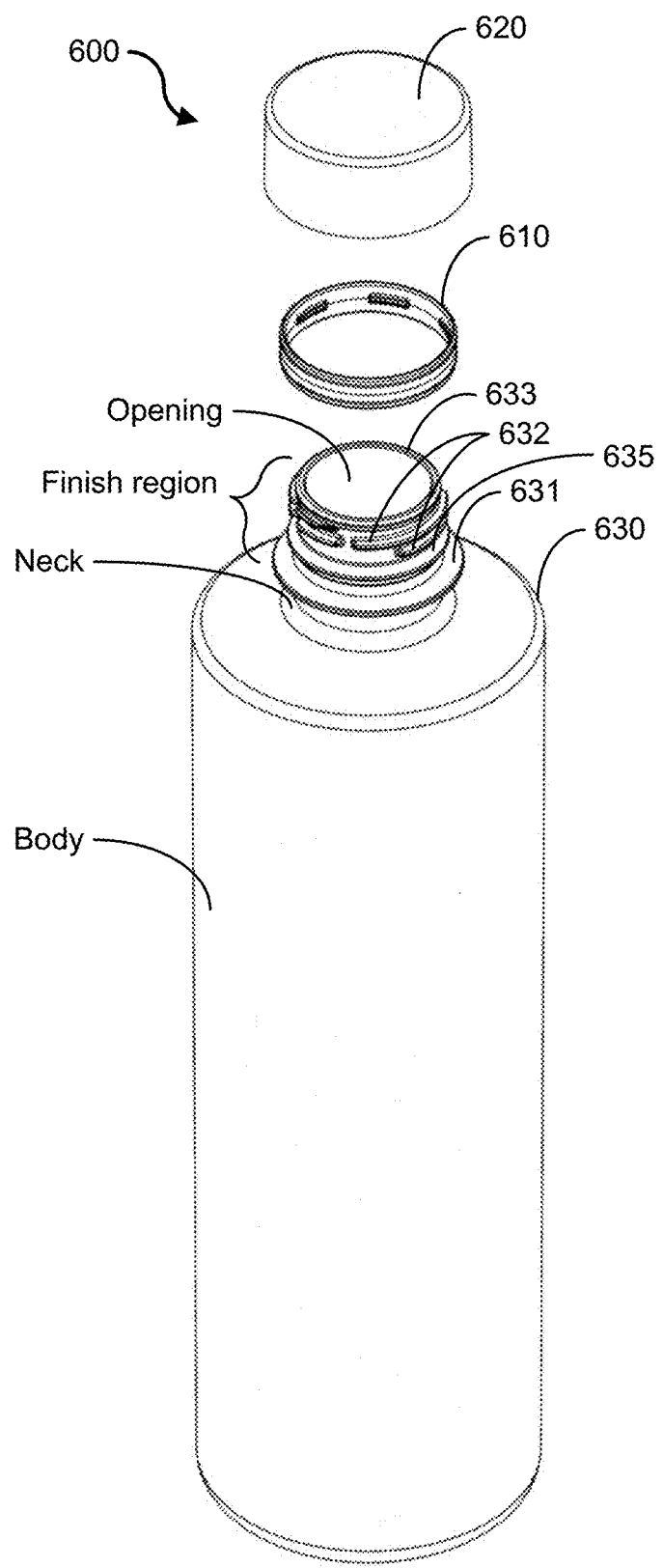
FIG. 6 shows an exploded view of an example embodiment of a scented bottle cap system.

FIG. 6 shows a diagram featuring an exploded view of an example embodiment 600 of the scented bottle cap system. The system 600 includes a scented ring 610 configured to attach around the finish region of the neck of a bottle 630, and a cap 620 to securely attach to the bottle 630 and enclose the scented ring 610 in a hollow region or cavity formed in the interior of the cap 620 and with a circumferential structure protruding from the neck of the bottle 630.

Figure 8A:
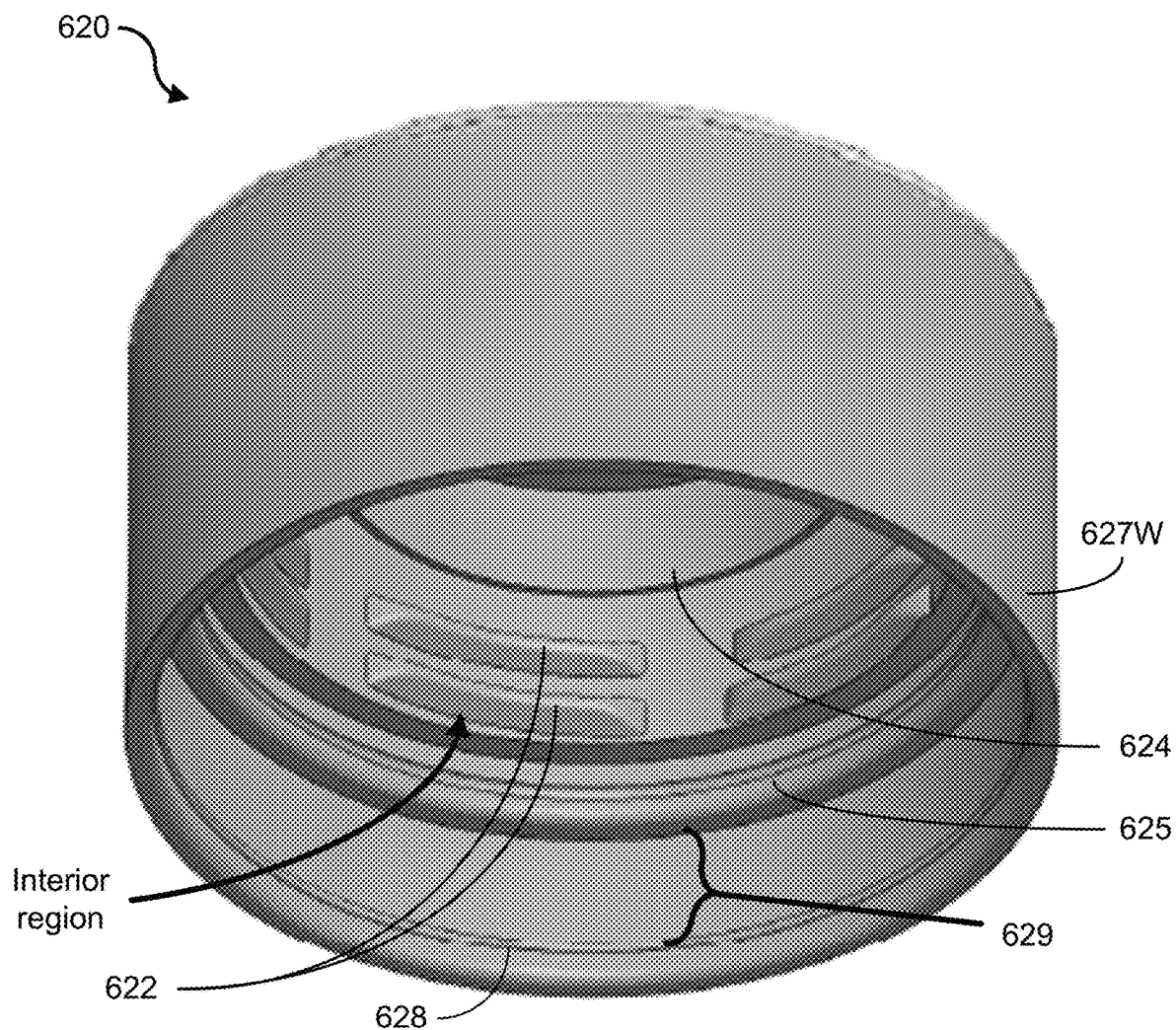
FIGS. 8A and 8B show example embodiments of the cap of the scented bottle cap system.

In the example shown in FIG. 6, the bottle 630 includes a collar 631, also referred to as a neck ring or a transfer thread, that protrudes outward and circumferentially around the neck of the bottle 630. In the example embodiment of the bottle 630, the collar 631 provides the circumferential structure to contact the bottom end of the cap 620 to form the hollow region or cavity in the interior of the cap 620. The bottle 630 includes a set of threads 632 that wrap around finish region of the neck of the bottle 630, above the collar 631, to provide a mechanism to securely attach to and removably detach the cap 620 from the bottle 630 by twisting the cap on and off, e.g., eliminating the need for an opener. As shown in FIG. 8A, the cap 620 includes a corresponding set of threads 622 protruding from the interior region of the cap 620 that interact with the set of threads 632 of the bottle 630 for attachment and detachment. The bottle 630 includes a terminus at the end of the neck that provides an opening to the interior of the bottle that contains a fluid (e.g., beverage such as water, soda, milk, juice, alcoholic beverage, etc.), which is filled and dispensed from the bottle through the opening. The terminus provides a sealing surface 633 at the top of the terminus that is structured to contact a corresponding sealing surface 623 of the cap 620, shown in FIG. 9, e.g., which prevents the fluid from leaking out of the bottle 630 when the cap 620 is securely attached thereto. For example, the sealing surface 633 is structured to be smooth and free from any imperfections that would prevent a consistent seal when in contact with the corresponding sealing surface 623, and likewise for the corresponding sealing surface 633. In some embodiments of the bottle 630, like the example in FIG. 6, the bottle 630 includes a ledge structure 635 that extends from a position on the neck of the bottle 630 to make contact with a protruding structure from the ring 610 that aligns and/or holds the ring 610 in a particular position with respect to the bottle 630 when the ring 610 attached to the bottle 630.

Figure 7:
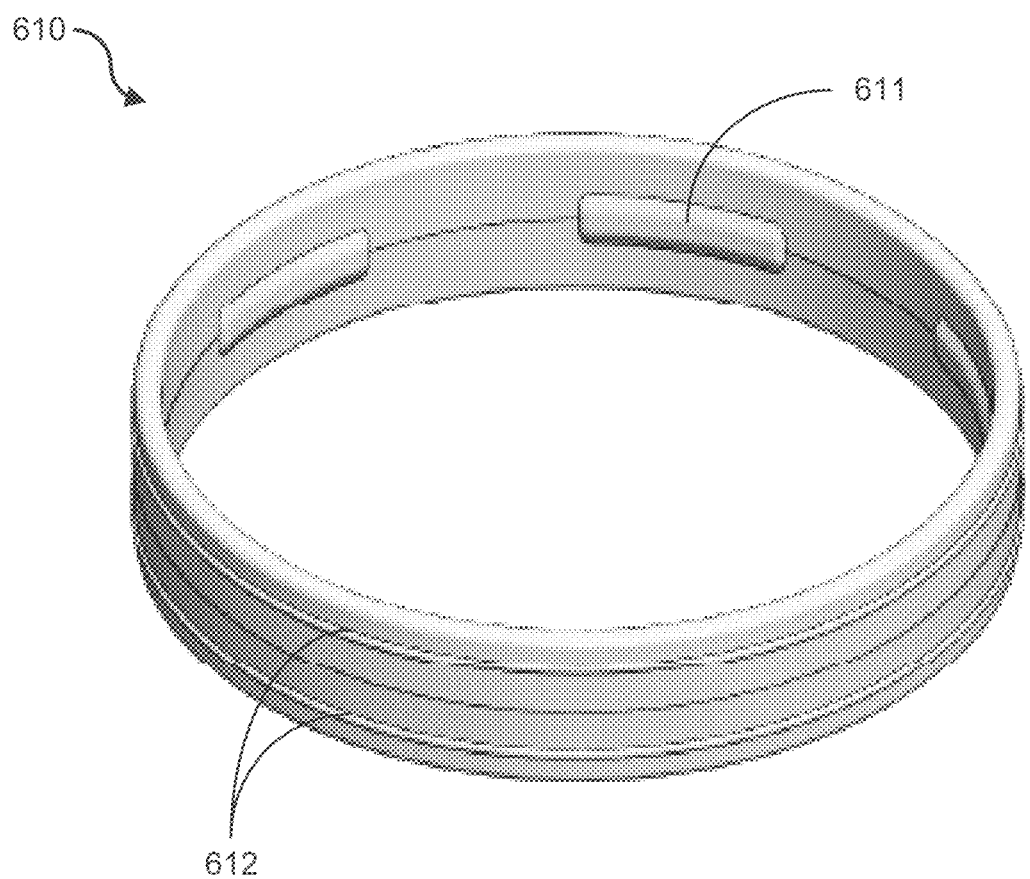
FIG. 7 shows an example embodiment of the scented ring of the scented bottle cap system.

FIG. 7 shows a diagram of an example embodiment of the scented ring 610. The scented ring 610 is structured to include a shape and size so as to fit around the circumference of a container, such as around the neck of the bottle 630. For example, the scented ring 610 can be made into any desired shape including a rounded ring, e.g., like the circular ring shown in the example of FIG. 7, a square or rectangular ring, a triangular ring, or the like, including regular or irregular dimensions, so as to fit a variety of containers such as bottles like bottle 630 jars, and the like.

In the example shown in FIG. 7, the scented ring 610 includes one or more protruding structures 611 disposed on the interior surface of the scented ring 610, referred to as "interior anchors". For example, in some embodiments, the scented ring 610 can include a plurality of interior anchors 611 disposed along a single axis or multiple axes of the interior surface; whereas in other embodiments, the interior anchors 611 can be one protruding structure that spans a portion or the entire circumference of the interior surface. In some implementations of the scented bottle cap system 600, the interior anchors 611 contact the ledge structure 635 of the bottle 630 to align and/or hold the scented ring 610 in a certain vertical position on the neck of the bottle 630. In such implementations, for example, the alignment of the scented ring 610 by the interior anchors 611 and the ledge structure 635 of the bottle 630 allows the scented ring 610 to remain secured, e.g., 'anchored', to the bottle 630 when the cap 620 is taken off the bottle 630. Moreover, for example, the interior anchors 611 can expand the surface area of the scented ring 610, which can be used to control the concentration of the scent that can be exposed from the scented ring 610 and thereby control some parameters that affect the diffusion of the scent into the environment of the bottle 630 when the cap 620 is removed.

Also shown in the example embodiment of the scented ring 610 in FIG. 7, the scented ring 610 includes one or more protruding structures 612 disposed on the exterior surface of the scented ring 610, referred to as "exterior anchors". For example, in some embodiments, the scented ring 610 can include a plurality of exterior anchors 612 disposed along a single axis or multiple axes of the exterior surface. In the example of FIG. 7, the scented ring 610 includes two exterior anchors 612 each configured as a single protruding structure that spans the entire circumference of the exterior surface at two respective locations, e.g., an upper and a lower position on the exterior surface. In some implementations of the scented bottle cap system 600, the exterior anchors 612 are configured to make contact with a rim structure 625 of the cap 620, shown in FIG. 8A. The exterior anchors 612 can affect the alignment and/or hold the scented ring 610 in a certain position with respect to the cap 620 in certain circumstances, e.g., during fabrication of a beverage to be contained in the bottle cap system 600. In implementations, for example, the exterior anchors 612 can expand the surface area of the scented ring 610, which, like the interior anchors 611, can be used to control the concentration of the scent that can be exposed from the scented ring 610 and thereby control some parameters that affect the diffusion of the scent into the environment of the bottle 630 when the cap 620 is removed.

For example, the scent can be incorporated into the body of the scented ring 610, e.g., through the manufacturing process such as injection molding, in which the chemical agents that form the scent are embedded in the material that forms the structure of the scented ring 610. In other embodiments, for example, the scent can be produced on the scented ring 610 by providing an exterior coating to the ring body, e.g., via spray coating, printing or other techniques to coat the scented ring 610. In implementations, the scent emanates from the scented ring 610 by diffusing into the air that surrounds the scented ring 610. Generally, over time the scent would eventually diffuse to a concentration where it would be ineffective to stimulate one's olfactory senses when placed near the user, such as when the user brings the bottle neck toward his/her mouth and nose. Thus, the scented bottle cap system 600 provides a structure that controls the storage and release of the scent from the scented ring 610, thereby (i) conserving the scent for longer durations and repeated uses, and (ii) regulating the timing and concentration of emanation of the scent to the ideal moments that effectuate the user's enjoyment of the beverage in the bottle 630.

FIG. 8A shows a diagram of an example embodiment of the cap 620. The cap 620 is structured to include a shape and size so as fasten to a container, such as around the neck of the bottle 630 at the finish region, and seal the substance within the bottle 630 from leaking or otherwise escaping via the opening of the bottle 630. For example, the external design of the cap 620 can be made into any desired shape including a cylindrical shape like that shown in the example of FIG. 8A, a conical shape, rectangular shape, a triangular shape, or the like, including regular or irregular dimensions. In some implementations, the cap 620 can include two or more parts, e.g., which can provide advantageous features such as reduced weight, lower costs to manufacturing, and/or desired aesthetics.

Figure 8B:
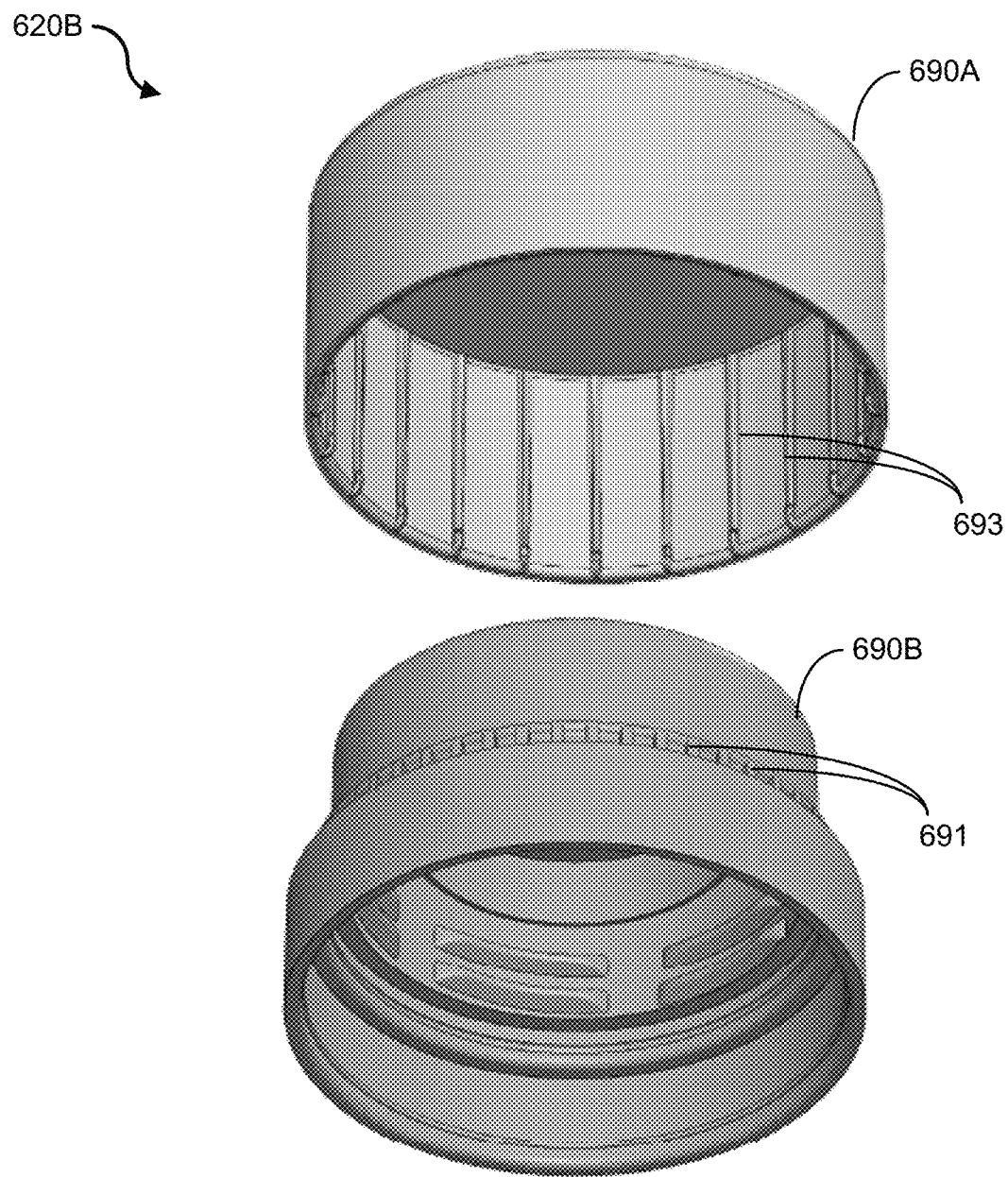

FIG. 8B shows a diagram of an example embodiment of a two-piece cap 620B, which includes an over-cap 690A and a cap base 690B, which attaches to each other via teeth 691 on the exterior of cap base 690B that align and interface with protruding pillars 693 on the interior of over-cap 690A. The cap base 690B includes the same interior components and structure as the example embodiment of the cap 620 shown in FIG. 8A. In some embodiments, the cap 620 can include the cap 620B, in which the over-cap 690A and the cap base 690B are one piece. For example, such embodiments of the cap 620B can include forming a single cap structure from the over-cap 690A and the cap base 690B in a manufacturing process, e.g., molding or adhering the two pieces into a single piece.

Referring back to FIG. 8A the cap 620 includes a top (not shown) and a curved wall 627W, which extends from the top of the cap 620 and terminates at a bottom end that forms the opening into an interior region of the cap 620. The interior region of the cap 620 includes a hollowed portion having interior structures to interface with the bottle 630 and the scented ring 610. The interior region of the cap 620 includes the rim structure 625 located at a position from the bottom end of the curved wall 627W, such that the rim structure 625 is configured to interface with the exterior anchors 612 of the scented ring 610. For example, the rim structure 625 is shaped to lightly support the exterior anchors 612 under certain circumstances, such as prior to assembly of the cap 620 and ring 610 with the bottle 630, in which the cap 620 can support suspension of the scented ring 610 when the cap 620 is oriented with its opening downward. In such example embodiments, for example, without the rim structure 625 and/or the exterior anchors 612, the scented ring 610 can fall out of cap 620 when its opening is oriented downward.

The bottom end of the curved wall 627W is structured such that, when the cap 620 is securely attached to the bottle 630, a portion of the bottom end contacts the collar 631 and provides a lower seal between the cap 620 and the collar 631 of the bottle 630. The cap 620 is structured to have a concentric space 629 in the interior region, which can be at least between the rim structure 625 and the location of the lower seal. In the example shown in FIG. 8A, the cap 620 includes a lip 628 that that spans the circumference of the interior region of the cap 620 to make contact with the collar 631 of the bottle to form the lower seal. When the cap 620 and scented ring 610 are assembled on the bottle 630, the concentric space 629 provides a hollow volume 940, illustrated in FIG. 9, that allows scent from the scented ring 610 to diffuse within in and be contained until the cap 620 is removed.

Figure 9:
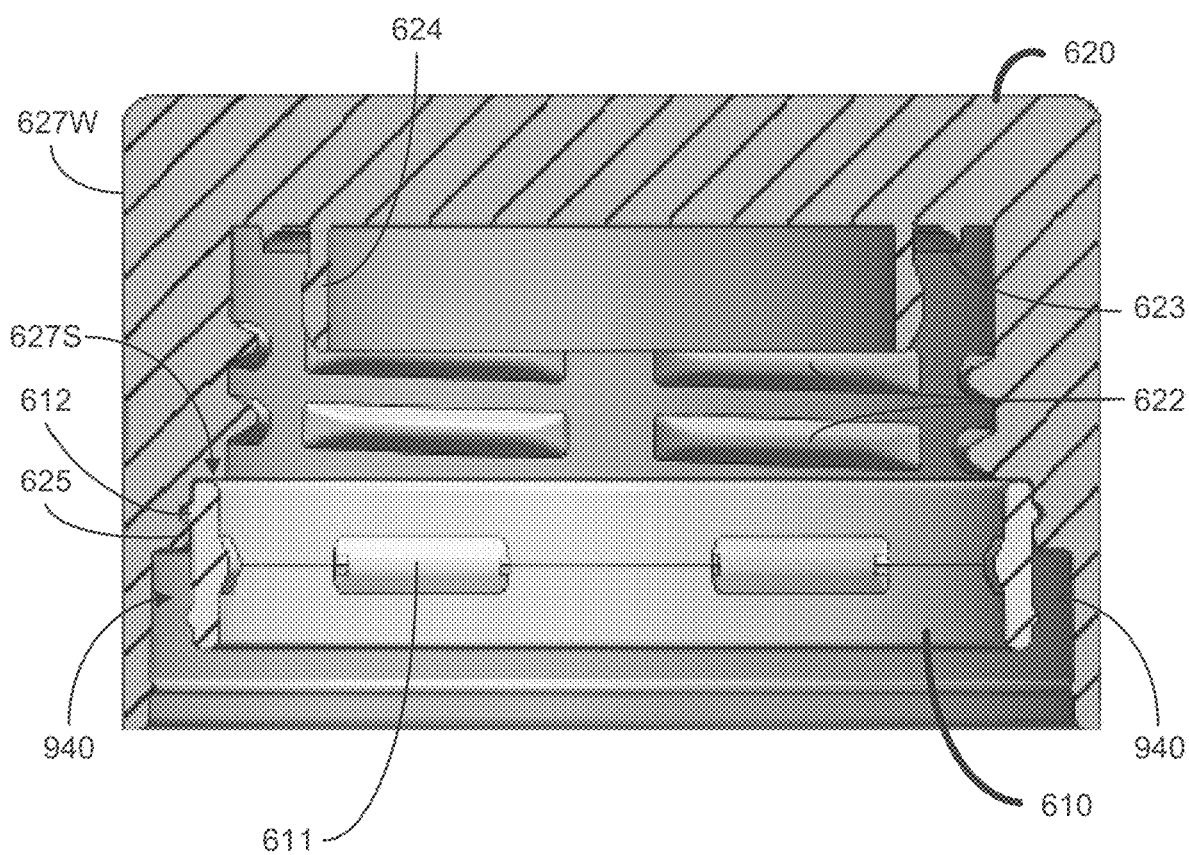
FIG. 9 shows a cross-sectional view of the scented ring coupled with the cap.

In some embodiments, such as the examples shown in FIGS. 8A and 9, the cap 620 includes a cylindrical protuberance 624 that projects from the top of the cap 620 and is configured to align with the side wall of the opening of the bottle 630. For example, the cylindrical protuberance 624 provides a sagittal sealing surface along the interior side wall of the opening of the bottle, as illustrated in FIG. 10A.

FIG. 9 shows a diagram depicting a cross-sectional view of the scented ring 610 coupled with the cap 620. The scented ring 610 is detachably coupled to the cap 620, such that when the cap 620 is oriented with the top upwards and its opening downwards, the scented ring 610 still resides in the interior region of the cap 620. The rim structure 625 provides sufficient support the exterior anchors 612 that allows the scented ring 610 to be suspended inside the cap 620 in this orientation. The interior side of the wall 627W includes a receiving surface 627S that allows the top side of the scented ring 610 to make contact. For example, the structure of the cap 620 and ring 610 allow for the ring 610 to be pre-loaded into the cap 620 prior to assembly with the bottle 630, e.g., such as during the bottling process of producing and packaging a beverage. In some implementations of a pre-loading process, the cap 620 can be inverted such that the opening is upwards and the top is downwards. The scented ring 610 can be secured within the interior of the cap 620, e.g., by automated machine or manually, such that the ring 610 is pushed into the interior until it makes contact with the receiving surface 627S, where the exterior anchors 612 will have over-passed the rim structure 625 and align within a conforming recess of the interior side of the wall 627W. The receiving surface 627S can assist in the alignment of the exterior anchors 612 passed the rim structure 625 and in the conforming recess of the cap 620, while allowing for various levels of force to place the ring 610 in this position.

Figure 10A:
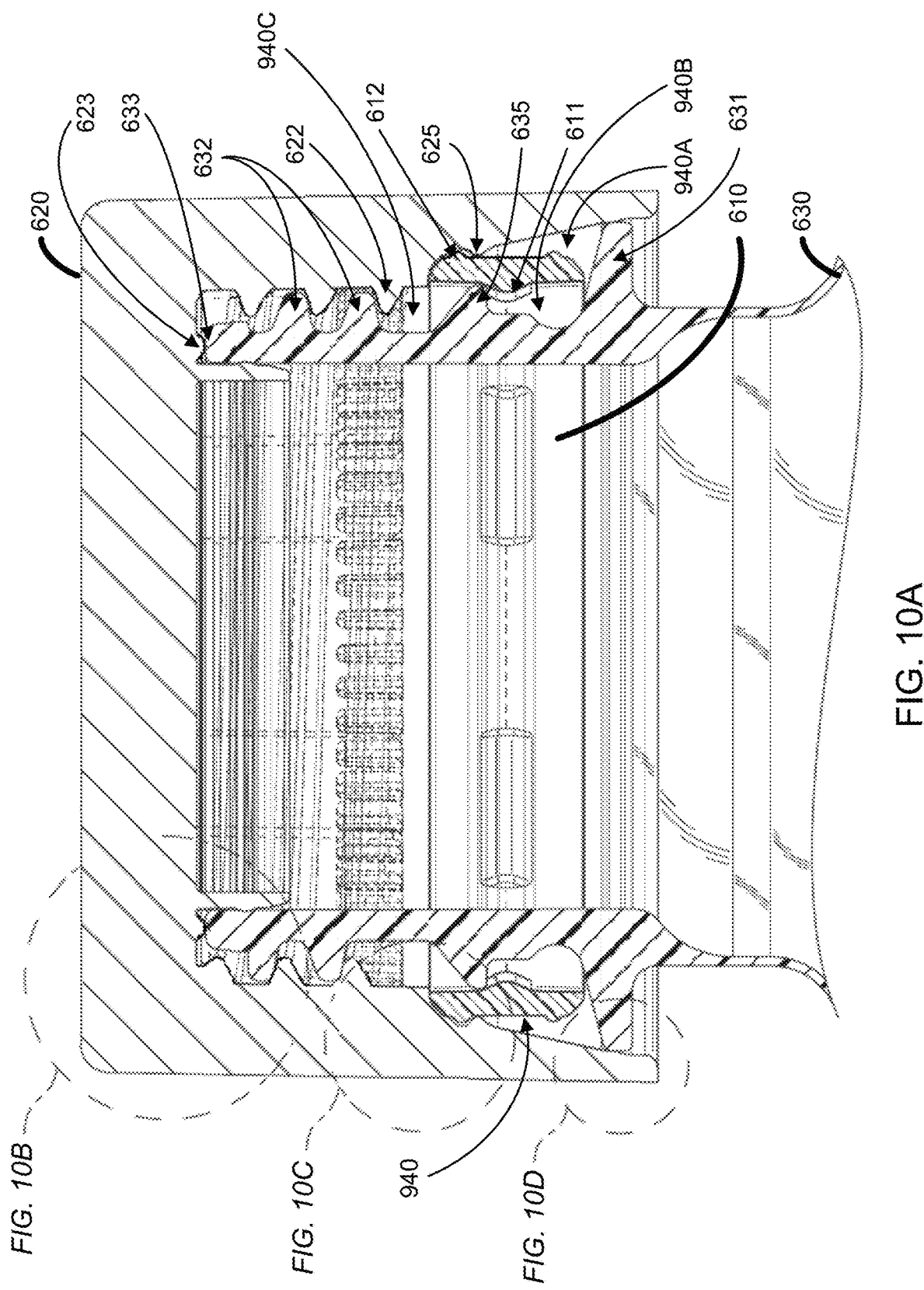
FIG. 10A shows a cross-sectional view of the scented bottle cap system when the scented ring, the cap and the bottle are assembled.

FIG. 10A shows a diagram depicting a cross-sectional view of the scented bottle cap system 600 when the scented ring 610, the cap 620 and the bottle 630 are assembled. In this configuration, the scented ring 610 is securely attached around the neck of the bottle 630 based on the positioning of the interior anchors 611 underneath ledge structure 635. For example, when the scent ring 610 is pre-loaded in the cap 620, the cap 620 can be initially attached to the bottle 630 (e.g., during the bottling process of the beverage production) such that the ring 610 detaches from the cap 620 and securely attaches to the bottle 630. In some implementations, the cap 620 is twisted on the bottle 630 via the set of threads 623 of the bottle 630 and the corresponding set of threads 622 of the cap 620. As the cap 620 is being twisted on the bottle 630, the scented ring 610 is driven downwards along the finish region such that the interior anchors 611 is pushed past the ledge structure 635. In the example shown in FIG. 10A, the ledge structure 635 can include a sloped portion on the upper side of the ledge structure 635, and a flattened portion on the lower side of the ledge structure 635 that is perpendicular with the neck of the bottle 635, which inhibits the ring 610 at the interior anchors 611 from detaching from the neck of the bottle 635. When the cap 620 is twisted off, the scented ring 610 is able to detach from its coupling with the cap 620, yet remain on the bottle 630.

Figure 10B:
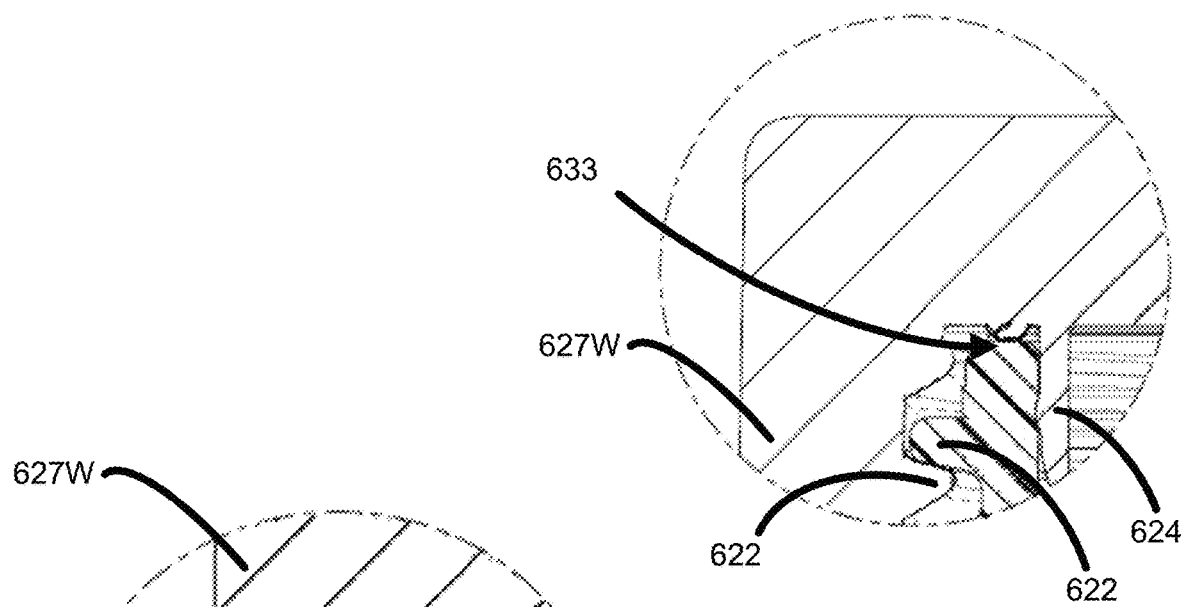
FIGS. 10B, 10C and 10D show magnified views of aspects of the scented bottle cap system shown in FIG. 10A.

FIG. 10B shows a magnified view of the interface between the sealing surface 623 of the cap 620 and the sealing surface 633 of the bottle 630 from FIG. 10A. When the cap 620 is securely attached to the bottle 630, e.g., fully twisted on, the sealing surface 633 of the bottle 630 contacts the corresponding sealing surface 623 of the cap 620. Similarly, the optional cylindrical protuberance 624 contacts the side wall of the opening of the bottle 630.

Figure 10C:
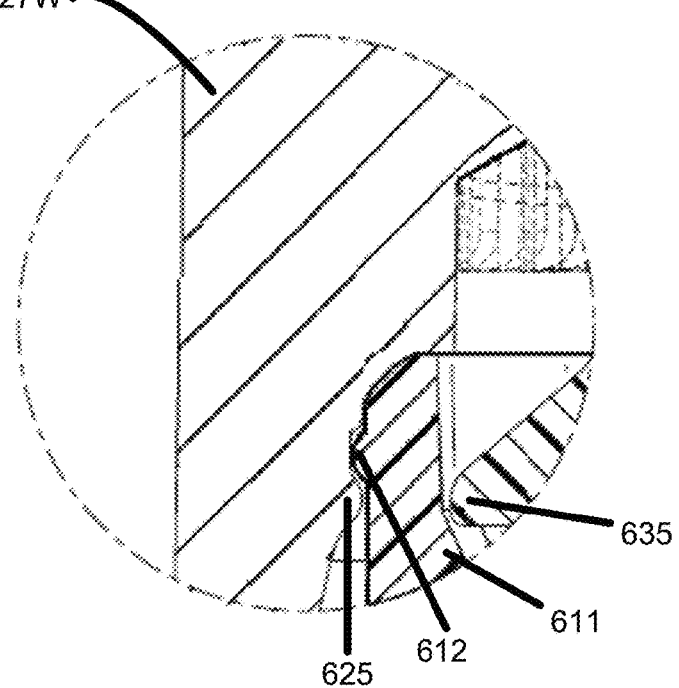

FIG. 10C shows a magnified view of the interface between the exterior anchors 612 of the scented ring 610 and the rim structure 625 of the cap 620, and the interface between the interior anchors 611 of the scented ring 610 and the ledge structure 635 of the bottle 630, as shown in FIG. 10A. For example, the ledge structure 635 can be configured to an angle that allows the scented ring 610 to securely attach, e.g., during assembly of the scented ring 610 with the cap 620 prior to assembly with the bottle 630, in which the interior anchors 611 of the scented ring 610 effectively slide down on the top side of the ledge structure 635 until they are beneath the ledge structure 635. In some embodiments, for example, the top angle of the ledge structure 635 is in a range of 120° to 150°, such as at substantially 135°. In some embodiments, for example, the top angle of the ledge structure 635 is in a range of 105° or more and 165° or less.

Figure 10D:
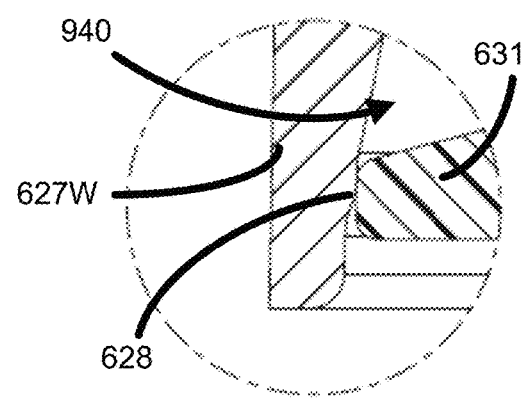

FIG. 10D shows a magnified view of the interface between the lip 628 of the cap 620 and the collar 631 of the bottle 630 from FIG. 10A. When the cap 620 is securely attached to the bottle 630, the lip 628 of the cap 620 is in contact with the collar 631 of the bottle 630, forming the lower seal that creates the hollow volume 940. The hollow volume 940 provides a chamber to collect the scent that diffuses into the volume 940 from the scented ring 610 when the cap 620 is closed. In the closed position, the scent is trapped and contained in the scented bottle cap system 600. When the cap 620 is removed from the bottle 630, e.g., twisted off, the user can experience an initial burst of scent, particularly when he/she removes the cap 620 and brings it towards his/her mouth to drink the beverage inside the bottle 630. The scent continues to emanate from the scent ring 610 attached to the bottle 630 and enthuse the senses of the user during subsequent imbibing of the beverage.

A compartment providing a hollow volume 940 formed in a space between the cap 620 and the bottle 630 can be configured based on the size and shapes of the structural components of the cap 620 and bottle 630. The compartment including the hollow volume 940 is configured to collect and trap the scent that emanates from the scented ring 610 when the cap 620 is closed (e.g., tightened) on the bottle 630. For example, the system 600 is configured to trap the scent when the cap 620 is closed on the bottle 630, e.g., including in-between drinks of the beverage, to create a scent burst effect when the user opens the cap and takes the next drink. As illustrated in the example embodiment shown in FIG. 10A, the compartment including the hollow volume 940 can include one or more regions, or subcompartments, in the space between the cap 620 and the bottle 630, for example, including (i) a lower region 940A between the exterior wall of the scented ring 610, the collar 631 and the interior face of the wall 627W of the cap 620 between the rim structure 625 of the cap 620 and collar 631 of the bottle 630; (ii) a middle region 940B between the interior wall of the scented ring 610 and the neck of the bottle 630 where the ring 610 is positioned between the ledge structure 635 and the collar 631; and (iii) an upper region 940C between the interior wall of the scented ring 610, the upper portion of the ledge structure 635 and the intersection of threads 622 and 632 of the cap 620 and bottle 630, respectively. The hollow volume 940, including each of the example subcompartment regions 940A, 940B and 940C, can be structured to have a particular volume or range of volumes for capturing a desired concentration of volatile scent from the scented ring 610. For instance, in certain embodiments such as that shown in FIG. 10A, the lower region of the hollow volume 940 may be in a range from about 3,000 mm$^3$ or less to about 1,000 mm$^3$ or more. In some embodiments, for example, the hollow volume formed by the system 600 may be in a range from about 15,000 mm$^3$ or less to about 100 mm$^3$ or more, which can be configured based on the size and shape of the structures along the interior face of the wall 627W interfacing the features of the neck of the bottle 630.

Figure 11A:
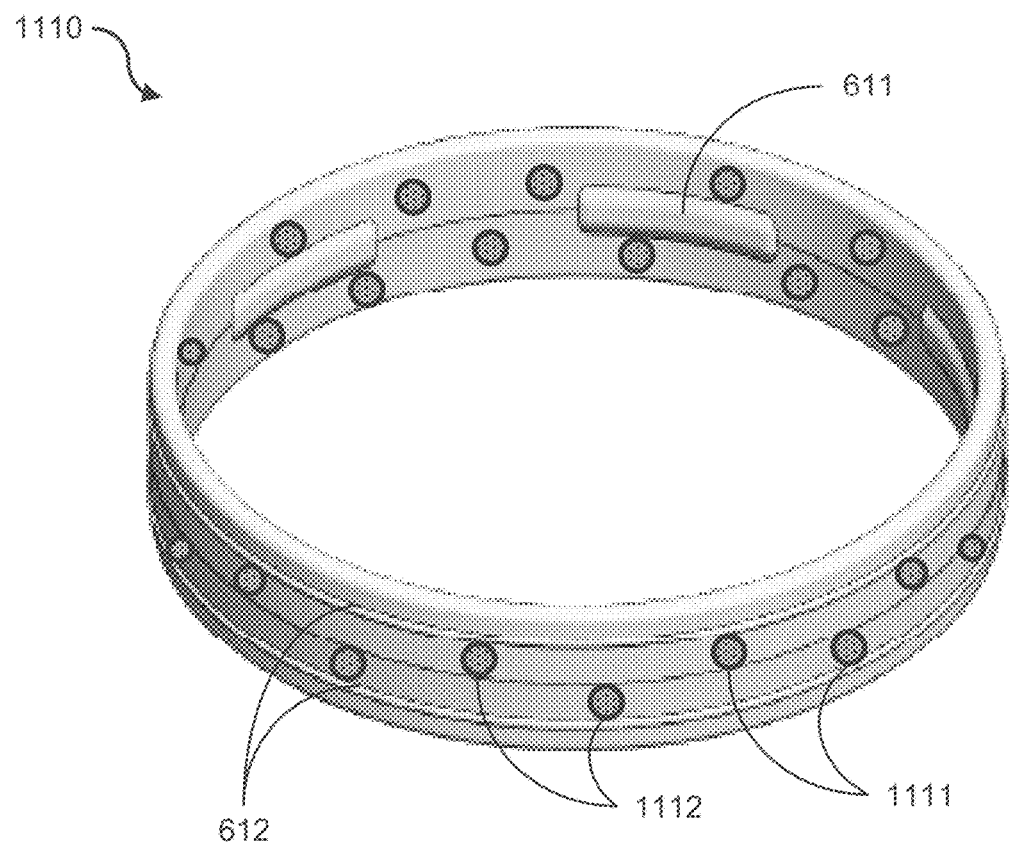
FIGS. 11A and 11B show example embodiments of the scented ring of the scented bottle cap system.

FIG. 11A shows a diagram of an example embodiment of the scented ring 1110. The scented ring 1110 includes the structure of the scented ring 610, and also includes dimples 1111 (e.g., pores) that recede inward with respect to the surface of the ring 1110 and/or bumps 1112 (e.g., protrusions) that protrude outward with respect to the surface of the ring 1110. The dimples 1111 and/or bumps 1112 can be organized along the surface of the ring 1110 in a variety of arrangements, e.g., including an array of periodic or aperiodic positioning, or randomly. For example, the dimples and/or bumps 1112 provide additional surface area to the scented ring 1110 that can increase the concentration of the scent exposed to the outer environment (e.g., air), and thereby enhance the delivery of the scent to the user. In some embodiments, for example, the dimples 1111 and/or bumps 1112 can be used to create letters, shapes, or symbols as a form of advertising or product differentiation.

In some implementations, the dimples 1111 and/or bumps 1112 are formed of a size and/or shape and arranged on the scented ring 1110 to affect the direction of the scent emanating from the scented ring 1110 to the proximate environment. For example, the motion of the bottle 630 by the user to drink the beverage can increase the rate of air flow at the scented ring 1110 and affect to the volatility of the scent at the dimples 1111 and the bumps 1112. Also, for example, the dimples 1111 can be structured as holes that pass through the ring 1110 or terminate at a hollowed chamber in the body of the ring 1110 to affect the effusive properties of the scent when the cap 620 is removed from the bottle 630. In some implementations, the dimples 1111 can be arranged on the region of the scented ring 1110 that is in contact with the cap 620 when securely attached to the bottle 630, e.g., such as arranged along the exterior anchors 612 that contact the rim structure 625. In such implementations, the scent can be trapped in the hollowed chambers and their release controlled accounting for the effusive properties of the scent through the dimples 1111 and into the outer environment, e.g., near the user's nose and mouth. In some implementations, the bumps 1112 can also be structured to affect the effusive properties of the scent to enhance the sensation of the user's olfactory system.

Figure 11B:
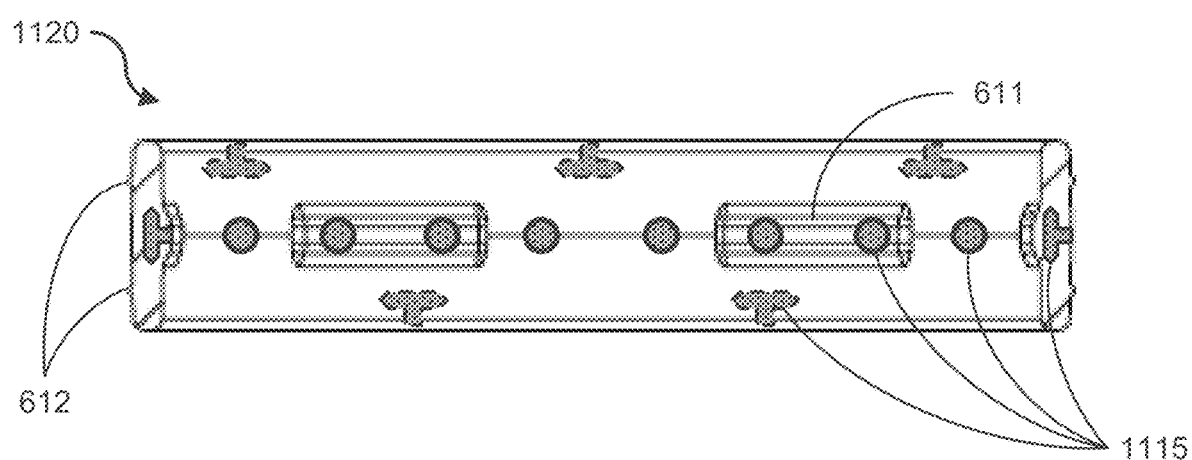

FIG. 11B shows a diagram of an example embodiment of the scented ring 1120 that includes hollowed chambers 1115 to trap the scent and having an outer passageway for their release that accounts for the effusive properties of the scent from the chambers 1115 to the outer environment, e.g., near the user's nose and mouth. For example, the chambers 1115 can be structured to affect the effusive properties of the scent to enhance the sensation of the user's olfactory system, and thereby drinking experience. In some embodiments, the scented ring 1120 can include an arrangement of the chambers 1115 such that the outer passageways form an opening on the interior wall of the scented ring 1120, the exterior wall of the scented ring 1120, or both the interior and exterior walls of the scented ring 1120. For example, the chambers 1115 can be configured such that the outer passageways form an opening on a top surface and/or a bottom surface of the scented ring 1120. In implementations, for example, the air may rapidly flow into the chambers 1115 when the user brings the bottle 630 with the attached scented ring 1120 toward his/her face for drinking the beverage fluid, and thereby experience an enhanced effect of the scent emanating from the scented ring 1115 due to the structure of the chambers 1115 and outer passageways to affect effusion of the scent. The scented ring 1120 can include similar structures of the scented ring 610 and/or 1110, e.g., including the interior anchors 611, the exterior anchors 612, and/or the dimples 1111 and/or bumps 1112.

Figure 12A:
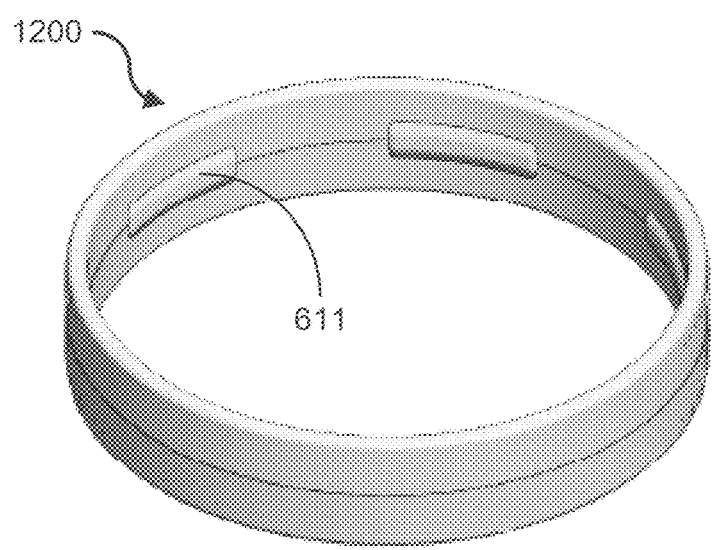
FIGS. 12A, 12B and 12C show example embodiments of the scented ring of the scented bottle cap system.

FIG. 12A shows a diagram of an example embodiment of the scented ring 1200. The scented ring 1200 includes the structure of the scented ring 610 or the scented ring 1110, except without the exterior anchors 612.

Figure 12B:
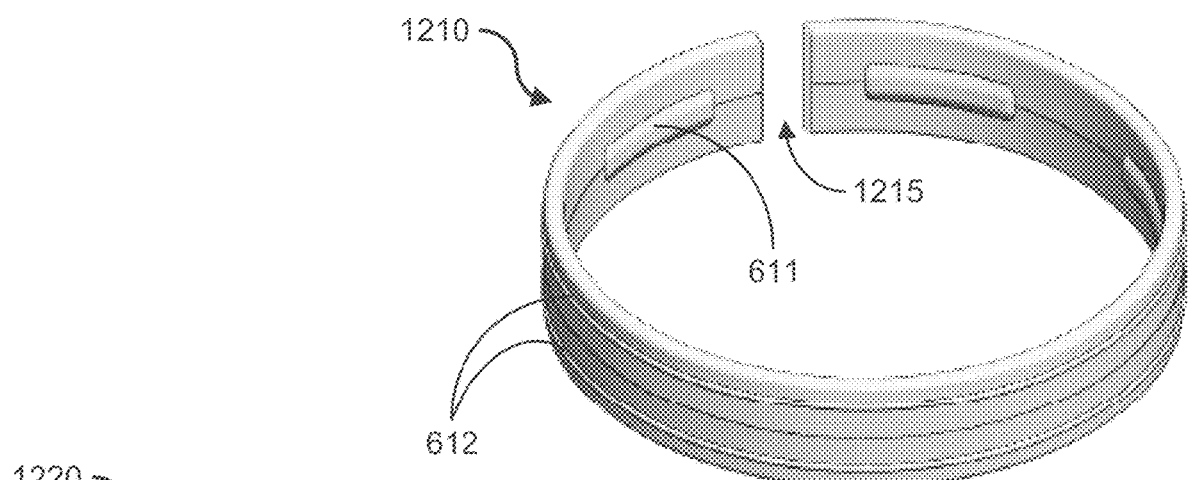

FIG. 12B shows a diagram of an example embodiment of the scented ring 1210. The scented ring 1210 includes the structure of the scented ring 610 or the scented ring 1110, and also includes a cut-away region 1215. This embodiment can be referred to as a scented C-ring. For example, the scented C-ring 1210 still provides the structure to be detachably coupled to the cap 620, e.g., for pre-loading, and securely attached to the bottle 630 after initial attachment of the ring-pre-loaded cap on the bottle, and yet also allows the scented C-ring 1215 to be selectively detached by the user based on the cut-away region 1215. Various embodiments of the scented ring can include a pliable material. In the example embodiments of the scented C-ring 1210, the material can allow the C-ring structure to bend slightly to have enough clearance for the scented C-ring 1210 to clear the diameter of the ledge structure 635 of the bottle 630 based on the cut-away region 1215. For example, the scented C-ring 1210 includes a pliable material to allow the scented C-ring 1210 to bend to at least a degree to have enough clearance for the cut-away region 1215 to expand and clear the diameter of the ledge structure 635 of the bottle 630 such that the scented C-ring 1210 can detach from the bottle 630. In implementations, for example, the scented C-ring 1210 can allow a user to swap scented rings as he/she chooses, and similarly allow the manufacturer to sell the scented rings separately from the bottle.

Figure 12C:
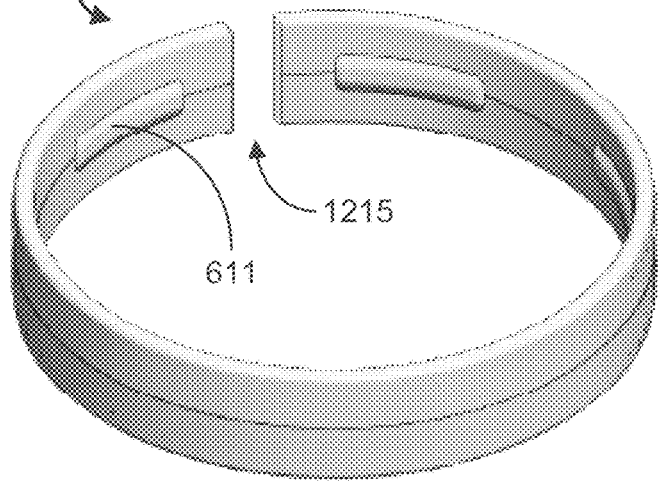

FIG. 12C shows a diagram of an example embodiment of the scented C-ring 1220 that includes the interior anchors 611 and the cut-away region 1215. In implementations, for example, the scented C-ring 1220 can allow a user to swap scented rings as he/she chooses, and similarly allow the manufacturer to sell the scented rings separately from the bottle.

In some aspects of the scented attachment for containers in accordance with embodiments of the present technology, methods are disclosed for manufacturing a scented bottle cap system to fill the bottle with a fluid, e.g., beverage, to be contained within the bottle and attaching the cap and scented ring to the bottle in a single step.

Figure 13:
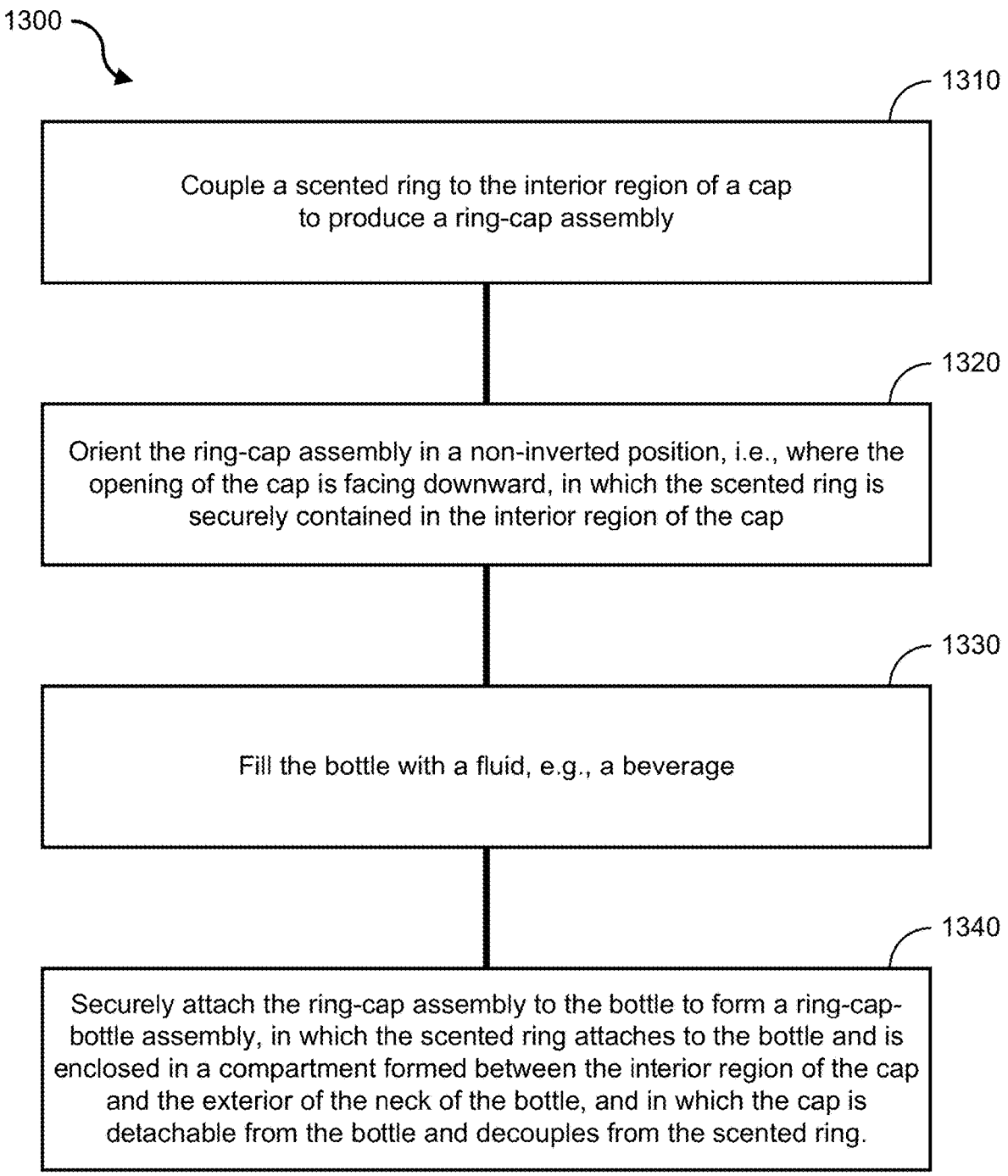
FIG. 13 shows a flow diagram an example embodiment of a method to manufacture a scented bottle cap system in accordance with embodiments of the disclosure.

FIG. 13 shows a flow diagram an example embodiment of a method 1300 to manufacture a scented bottle cap system, such as the various embodiments of the system 600. The method 1300 includes a process 1310 to couple a scented ring, e.g., scented ring 610, 1110, 1200 or 1210, to an interior region of the cap, e.g., cap 620, to produce a ring-cap assembly. In some implementations of the process 1310, for example, the scented ring is detachably coupled to the cap such that the ring-cap assembly securely contains the scented ring in the interior region of the cap, e.g., maintaining the scented ring in the interior region even when the cap is oriented with the opening of the cap facing down. For example, the scented ring is configured to detachably couple to the cap prior to initial attachment of the ring-cap assembly with the bottle, such that the scented ring initially couples to the cap based on contact between the an exterior protruding structure of the scented ring and an interior protrusion (e.g., rim) structure of the cap, so that when the cap is initially fastened to the bottle, the scented ring transfers from being coupled to the cap to being coupled to the bottle, e.g., based on contact between the interior protruding structure of the scented ring and a protuberance structure such as a ledge feature extending from the neck of the bottle.

The method 1300 includes a process 1320 to orient the ring-cap assembly in a non-inverted position, i.e., where the opening of the cap is facing downward, in which the scented ring is securely contained in the interior region of the cap. The method 1300 includes a process 1330 to fill the bottle with a fluid, e.g., a beverage such as water, milk, juice, sports drink, alcoholic beverage, etc. The method 1300 includes a process 1340 to securely attach the ring-cap assembly to the bottle to form a ring-cap-bottle assembly, in which the scented ring attaches to the bottle and is enclosed in a compartment formed between the interior of the cap and the exterior of the neck of the bottle, and in which the cap is detachable from the bottle and decouples from the scented ring. In implementations of the process 1340, the ring-cap assembly is attached to the bottle in a single step. For example, the method 1300 allows the 'bottling process' of a beverage to be performed using conventional machine- or automated-equipment in existing bottle factories to perform the processes 1320, 1330 and 1340 without significant modifications to the existing bottling process set-up and infrastructure, and thereby enable mass production of scent-enhanced beverages using a scented bottle cap system in accordance with the disclosed technology in cost-conserving manner. The ring-cap-bottle assembly forms a system that (i) contains the beverage filled in the bottle, (ii) contains and conserves the scent in the compartment, preventing its escape until a user chooses to open the cap from the bottle, and (iii) affects the emanation of the scent to stimulate the user's olfactory system and enhance the user's enjoyment of the beverage.

In some embodiments, for example, the method 1300 includes a process to attach a tamper seal (e.g., sticker) to the produced ring-cap-bottle assembly that contains the fluid, e.g., providing an indicator to a user that the fluid contained in the ring-cap-bottle assembly is unadulterated and untampered. In some implementations, for example, the tamper seal is applied at a portion or completely around the interface of the cap with the bottle. In some embodiments, for example, the method 1300 includes a process to apply one or more labels to the bottle.

EXAMPLES

Examples of the scented attachment for containers include the following.

In some example embodiments, a scent delivery system for a beverage container (example B1) includes a bottle to contain a fluid beverage, the bottle structured to include a body region and a neck region, the bottle including a collar that extends outward and circumferentially around the neck region, and a ledge structure that extends outward and circumferentially around the neck region and is positioned above the collar; a scent ring including a body loaded with a volatile chemical agent to emanate from the body of the scent ring to generate a scent, the scent ring structured to include at least one interior protruding structure that projects from an interior wall of the body of the scent ring, in which the scent ring is configured to fasten around the neck region of the bottle based on contact between the at least one interior protruding structure of the scent ring and the ledge structure of the bottle, in which the at least one interior protruding structure is positioned below the ledge structure; and a cap reversibly attachable to the bottle, the cap including an interior rim structure that projects from and circumferentially around an interior cap wall of the cap, in which the cap is structured to enclose the scent ring in a compartment formed between the collar of the bottle and the interior rim structure of the cap when the cap is securely fastened to the bottle, in which the system is configured to trap the scent from the scent ring in the compartment when the cap is securely attached to the bottle and to release the scent into an outer environment of the bottle when the cap is detached from the bottle.

Example B2 includes the system of example B1, in which the scent ring includes at least one exterior protruding structure that projects from an exterior wall of the body of the scent ring.

Example B3 includes the system of example B2, in which the scent ring is configured to detachably couple to the cap prior to initial attachment of the cap and the scent ring to the bottle, in which the scent ring initially couples to the cap based on contact between the at least one exterior protruding structure of the scent ring and the interior rim structure of the cap, and when the cap is initially fastened to the bottle the scent ring transfers from being coupled to the cap to being coupled to the bottle based on contact between the at least one interior protruding structure of the scent ring and the ledge structure of the bottle.

Example B4 includes the system of example B1, in which the scent ring is operable to generate the scent without physical contact by the cap or by the bottle.

Example B5 includes the system of example B1, in which the system is operable to repeatedly trap the scent generated by the scent ring in the compartment and release the scent into the outer environment over a plurality of instances where a user attaches and detaches the cap to the bottle.

Example B6 includes the system of example B1, in which the at least one interior protruding structure includes a single interior protruding structure that spans circumferentially along at least a portion of the interior wall of the scent ring.

Example B7 includes the system of example B1, in which the at least one interior protruding structure includes a plurality of interior protruding structures that intermittently or periodically span circumferentially along the interior wall of the scent ring.

Example B8 includes the system of example B7, in which the plurality of interior protruding include two or more of the interior protruding structures that are equally spaced apart from each other.

Example B9 includes the system of example B1, in which the collar is structured to have a top side that slants downward from the surface of the neck region, and the collar is structured to have the bottom side that is substantially perpendicular to the neck region.

Example B10 includes the system of example B1, in which the cap is structured to include threads on the interior cap wall that interface with corresponding threads on the neck of the bottle to allow the cap to twist on and off the bottle.

Example B11 includes the system of example B1, in which the scent ring includes one or more pores that recede inward with respect to the surface of the body of the scent ring.

Example B12 includes the system of example B11, in which the one or more dimples include a plurality of dimples arranged along the surface of the body of the scent ring in an array of periodic or aperiodic positions, or randomly positioned.

Example B13 includes the system of example B1, in which the scent ring includes one or more protrusions that protrude outward with respect to the surface of the body of the scent ring.

Example B14 includes the system of example B13, in which the one or more protrusions include a plurality of protrusions arranged along the surface of the body of the scent ring in an array of periodic or aperiodic positions, or randomly positioned.

Example B15 includes the system of example B1, in which the scent ring includes a cut-away region across the body to allow the scent ring to be detachably coupled to the bottle, such that the scent ring is selectively detachable from the bottle.

Example B16 includes the system of example B15, in which the scent ring includes a pliable material to allow the scent ring to bend to at least a degree to have enough clearance for the cut-away region to expand and clear the diameter of the ledge structure of the bottle such that the scent ring detaches from the bottle.

Example B17 includes the system of example B1, in which the scent ring includes one or more hollowed chambers to trap the scent and having an outer passageway for release of the scent via effusion to the outer environment of the bottle when the cap is detached from the bottle.

Example B18 includes the system of example B1, in which the compartment includes a plurality of subcompartments such that different portions of the scent ring are exposed to a hollow volume of different subcompartments.

Example B19 includes the system of example B18, in which the plurality of subcompartments include (i) a lower subcompartment located between an exterior wall of the scent ring, the collar of the bottle, and a portion of the interior cap wall of the cap between the interior rim structure and the collar; (ii) a middle subcompartment located between the interior wall of the scent ring and the neck region of the bottle where the scent ring is positioned between the ledge structure and the collar; and (iii) an upper subcompartment located between the interior wall of the scent ring, a portion of the neck region of the bottle from a top side of the ledge structure to an intersection of threads on the interior cap wall that interface with corresponding threads on the neck region of the bottle, and a portion of the interior cap wall of the cap between the intersection of threads and the scent ring.

Example B20 includes the system of example B1, in which the compartment includes a hollow volume configured to trap the scent that emanates from the scent ring when the cap is securely attached to the bottle to concentrate the scent in the compartment, such that a concentrated scent is released into the outer environment of the bottle after the cap is detached from the bottle.

Example B21 includes the system of example B20, in which the hollow volume is in a range of 1 $mm^3$ to 3 $mm^3$.

Example B22 includes the system of example B1, in which the system is configured to release the scent to the outer environment to augment a perceived taste of the fluid beverage when drank by a user from the bottle.

Example B23 includes the system of example B21, in which the scent includes an odorous chemical agent operable to stimulate a chemoreceptor of the user's olfactory system to enhance the user's sense of smell or taste of fluid beverage.

In some example embodiments, a scent delivery system for a beverage container (example B24) includes a bottle to contain a fluid beverage, the bottle structured to include a body region and a neck region, the bottle including a collar that extends outward and circumferentially around the neck region, and a ledge structure that extends outward and circumferentially around the neck region and is positioned above the collar; and a bottle cap apparatus reversibly attachable to a bottle at the neck region to reversibly seal an opening of the bottle. The bottle cap apparatus includes scent ring including a body loaded with a volatile chemical agent to emanate from the body of the scent ring to generate a scent, the scent ring structured to include at least one interior protruding structure that projects from an interior wall of the body of the scent ring, in which the scent ring is configured to fasten around the neck region of the bottle based on contact between the at least one interior protruding structure of the scent ring and the ledge structure of the bottle, in which the at least one interior protruding structure is positioned below the ledge structure, and the scent ring structured to include at least one exterior protrusion structure that projects from an exterior wall of the body of the scent ring; and a cap including an interior rim structure that projects from and circumferentially around an interior cap wall of the cap, in which the cap is structured to enclose the scent ring in a compartment formed between the collar of the bottle and the interior rim structure of the cap when the cap is securely fastened to the bottle. The system is configured to trap the scent from the scent ring in the compartment when the cap is securely attached to the bottle and to release the scent into an outer environment of the bottle when the cap is detached from the bottle. In the system, the scent ring is configured to detachably couple to the cap prior to initial attachment of the bottle cap apparatus with the bottle, in which the scent ring initially couples to the cap based on contact between the at least one exterior protruding structure of the scent ring and the interior rim structure of the cap, and when the cap is initially fastened to the bottle the scent ring transfers from being coupled to the cap to being coupled to the bottle based on contact between the at least one interior protruding structure of the scent ring and the ledge structure of the bottle.

Example B25 includes the system of example B24, in which the compartment includes a hollow volume configured to trap the scent that emanates from the scent ring when the cap is securely attached to the bottle to concentrate the scent in the compartment, such that a concentrated scent is released into the outer environment of the bottle after the cap is detached from the bottle.

Example B26 includes the system of example B24, in which the scent ring is operable to generate the scent without physical contact by the cap or by the bottle.

Example B27 includes the system of example B24, in which the system is operable to repeatedly trap the scent generated by the scent ring in the compartment and release the scent into the outer environment over a plurality of instances where a user attaches and detaches the cap to the bottle.

Example B28 includes the system of example B24, in which the at least one interior protruding structure includes a single interior protruding structure that spans circumferentially along at least a portion of the interior wall of the scent ring.

Example B29 includes the system of example B24, in which the at least one interior protruding structure includes a plurality of interior protruding structures that intermittently or periodically span circumferentially along the interior wall of the scent ring.

Example B30 includes the system of example B29, in which the plurality of interior protruding include two or more of the interior protruding structures that are equally spaced apart from each other.

Example B31 includes the system of example B24, in which the collar is structured to have a top side that slants downward from the surface of the neck region, and the collar is structured to have the bottom side that is substantially perpendicular to the neck region.

Example B32 includes the system of example B24, in which the cap is structured to include threads on the interior cap wall that interface with corresponding threads on the neck of the bottle to allow the cap to twist on and off the bottle.

Example B33 includes the system of example B24, in which the scent ring includes one or more pores that recede inward with respect to the surface of the body of the scent ring.

Example B34 includes the system of example B33, in which the one or more dimples include a plurality of dimples arranged along the surface of the body of the scent ring in an array of periodic or aperiodic positions, or randomly positioned.

Example B35 includes the system of example B24, in which the scent ring includes one or more protrusions that protrude outward with respect to the surface of the body of the scent ring.

Example B36 includes the system of example B35, in which the one or more protrusions include a plurality of protrusions arranged along the surface of the body of the scent ring in an array of periodic or aperiodic positions, or randomly positioned.

Example B37 includes the system of example B24, in which the scent ring includes a cut-away region across the body to allow the scent ring to be detachably coupled to the bottle, such that the scent ring is selectively detachable from the bottle.

Example B38 includes the system of example B37, in which the scent ring includes a pliable material to allow the scent ring to bend to at least a degree to have enough clearance for the cut-away region to expand and clear the diameter of the ledge structure of the bottle such that the scent ring detaches from the bottle.

Example B39 includes the system of example B24, in which the scent ring includes one or more hollowed chambers to trap the scent and having an outer passageway for release of the scent via effusion to the outer environment of the bottle when the cap is detached from the bottle.

Example B40 includes the system of example B24, in which the compartment includes a plurality of subcompartments such that different portions of the scent ring are exposed to a hollow volume of different subcompartments.

Example B41 includes the system of example B40, in which the plurality of subcompartments include (i) a lower subcompartment located between an exterior wall of the scent ring, the collar of the bottle, and a portion of the interior cap wall of the cap between the interior rim structure and the collar; (ii) a middle subcompartment located between the interior wall of the scent ring and the neck region of the bottle where the scent ring is positioned between the ledge structure and the collar; and (iii) an upper subcompartment located between the interior wall of the scent ring, a portion of the neck region of the bottle from a top side of the ledge structure to an intersection of threads on the interior cap wall that interface with corresponding threads on the neck region of the bottle, and a portion of the interior cap wall of the cap between the intersection of threads and the scent ring.

Example B42 includes the system of example B24, in which the compartment includes a hollow volume configured to trap the scent that emanates from the scent ring when the cap is securely attached to the bottle to concentrate the scent in the compartment, such that a concentrated scent is released into the outer environment of the bottle after the cap is detached from the bottle.

Example B43 includes the system of example B42, in which the hollow volume is in a range of 1 $mm^3$ to 3 $mm^3$.

Example B44 includes the system of example B24, in which the system is configured to release the scent to the outer environment to augment a perceived taste of the fluid beverage when drank by a user from the bottle.

Example B45 includes the system of example B44, in which the scent includes an odorous chemical agent operable to stimulate a chemoreceptor of the user's olfactory system to enhance the user's sense of smell or taste of fluid beverage.

In some example embodiments, a method for manufacturing a scented bottle cap system (example B46) includes coupling a scent ring to an interior region of a cap to produce a ring-cap assembly; orienting the ring-cap assembly in a position where an opening of the cap to the interior region is facing downward, in which the scent ring is securely contained in the interior region of the cap; filling the bottle with a fluid; and securely attaching the ring-cap assembly to the bottle, in which the scent ring attaches to the bottle and is enclosed in a compartment formed between the interior region of the cap and an exterior region of a neck portion of the bottle, in which the ring-cap assembly is attached to the bottle in a single step, in which the cap is detachable from the bottle and decouples from the ring upon initial detachment from the bottle.

Example B47 includes the method of example B46, in which the attaching the scent ring to the cap includes inserting the scent ring to the interior region of the cap such that an exterior protruding structure of the scent ring is inserted past an interior protrusion structure of the cap.

Example B48 includes the method of example B46, in which when the ring-cap assembly is initially attached to the bottle, the scent ring transfers from being coupled to the cap to being attached to the bottle, in which attachment between the scent ring and the bottle is based on contact between an interior protruding structure of the scent ring and a protuberance structure extending from the exterior region of the neck portion of the bottle.

In some example embodiments, a scented bottle cap apparatus (example C1) includes a scent ring to attach around a neck of a bottle having a collar, in which the scent ring includes a body loaded with a volatile chemical agent to emanate from the body of the scent ring to generate a scent; and a cap to removably attach to the bottle and structured to enclose the scent ring in a compartment formed between the collar of the bottle and an interior portion of the cap when the cap is securely attached to the bottle, in which the system is configured to trap a scent from the scent ring in the compartment when the cap is securely attached to the bottle and release the scent into an outer environment of the bottle when the cap is detached from the bottle.

Methods for Manufacturing Scented Material Compositions and Articles

Fragrance or aroma compounds have been used since antiquity to freshen air and cover odors. One early example includes incense, an aromatic material that forms a fragrant smoke when burned, which is believed to have been used by the ancient Egyptians, Babylonians, and other ancient peoples thousands of years ago. Perfumes were developed over time, having various concentrations of aromatic compounds in a solvent, such as an alcohol. For example, an eau de cologne typically has 3-8% aromatic compound(s) in solvent, whereas an eau de toilette has 5-15% aromatic compound(s) in solvent. By the middle of the twentieth century, fragrance compounds were manufactured into aerosol sprays for air freshener and deodorant products; and decades later, scented materials were developed in products like scented candles.

In humans, mammals and other living things, the olfactory system detects airborne substances, e.g., volatile chemicals, and provides the living organism with a sense of smell. Olfaction, like taste, is a form of chemoreception. Accordingly, there is a commonality between the perception of smell and the perception of taste. In certain instances, the sense of smell may supplement and/or otherwise enhance the sense of taste, and, for example, maladies affecting the sense of smell adversely affect the sense of taste.

Taste plays an important role in one's motivation for consuming food or drink. As such, food science has spent decades formulating new processed foods and drinks having agents that enhance the perception of taste of food and drink articles. However, more and more studies are showing adverse health effects for some processed foods, which can be due to additives that were used to enhance perception of taste.

Scent-based technologies, such as scented materials and articles, can be used to augment the characteristics of the material or article to affect a person's sense of smell, and thereby sense of taste. For example, a scented material or article may include a chemical agent, such as a fragrance or aroma compound, that stimulates a chemoreceptor of the olfactory system of the subject or otherwise stimulates sense of smell and/or taste of a subject.

One example of scent-based technologies includes scented articles that attach or are included as part of a drinking bottle system, like those described in this patent document, in which the scented article provides a pleasing odorant to a user that stimulates a corresponding chemoreceptor of the user's olfactory system to enhance the user's sense of smell and/or taste of a drinkable fluid in the bottle. For example, the scented article can be a lime-scented ring that attaches to the bottle around the bottle opening so that, as the user drinks the beverage within the bottle, such as water, the user experiences a lime-taste to the water from the lime scent that emanates from the scented article while drinking.

For such scented articles attachable to a drinking bottle, the final scented product should have a small size relative to the bottle and/or cap, and therefore limited surface area, while having a strong structure to prevent unintentional detachments from the bottle (e.g., which could cause choking) or unintended uses (e.g., user eating the scented article)—and yet must still provide a strong-enough scent for the user to smell while consuming the beverage. For the scented article to achieve such functionality with a small size, the fragrance composition should be loaded and preserved at a sufficient concentration in the base material to produce a robust, stable scented product suitable for applications like scented beverage container systems.

Yet, producing scented articles that have small sizes and surface areas for emanating the scent is not achievable with conventional approaches for manufacturing scented articles. This may be because low concentration scented articles can be made suitable for various applications where the size and surface area of the article is not as limiting as for the example scented attachments disclosed in this patent document, including but not limited to the scented ring 610 and/or other examples of the scented rings described herein. Existing manufacturing methods to produce scented articles use relatively low concentrations of the fragrance compound in the bulk material of the article, e.g., such as concentrations of 1% or less. For example, conventional methods may produce the scented article using a fragrance material such as a fragrance oil having a relatively low concentration of the scented compound (e.g., 5% concentration or less) that is loaded in the bulk material at loads of 10% or less with respect to the base material(s), which results in a 0.5%, or less, concentration of fragrance composition in the scented article. As such, conventional approaches for manufacturing scented articles do not address the challenge of loading high concentrations of a fragrance material in low volumes of base materials, let alone for scented articles that require robust, rigid plastics as the base material to provide the structure and shape of the article.

The challenges in manufacturing solid scented materials includes designing a stable material that has a high adsorption capacity for volatile compounds. In the design of scented material, the rigid plastic must (1) trap a sufficient amount of the scented compound in the plastic (e.g., the polymeric matrix) in order to deliver the scent and (2) control the capture of the fragrant compound as a function of time such that there is a controlled and continuous release of the scented material over a given period of time. For example, if the polymeric material (e.g., the plastic) is packed too tightly, that is not porous enough, the fragrance will not be effectively released from the material and therefore, the fragrance will not be delivered. Conversely, if the polymeric material is packed too loosely, that is too porous, then the fragrant compound will rapidly diffuse out of the plastic, resulting in an unstable scented material. Moreover, scented compounds typically exhibit properties that make them difficult to manage during synthesis and post-synthesis, such as sensitivities to oxidation, hydrolysis and heat that cause the scented compounds and/or their constituents to be affected by the presence of oxygen, water, and heat, respectively, in their production environments. Since different scented compounds provide different fragrances or aromas, their chemical constituents vary between the compounds, which adds further complexity to the compound synthesis process to produce an effective, stable scented compound to meet the load requirements for integration into a solid material, like plastic. In view of the above, the design of a scented material requires a fine balance among synthesizing the scented compound to have the desired fragrance with appropriate load ratios and manufacturing a solid scented material with an optimal porosity that enables the adsorption of the volatile compounds, but also, the subsequent slow diffusion of the volatile compounds from the material.

Disclosed are scented material compositions, scented articles and methods and systems of their manufacture. In particular, the disclosed scented materials and articles include scented articles for a bottle cap system having a scented attachment for enhancing a user's sense of smell and/or taste of a beverage in the bottle.

The disclosed methods and systems for manufacturing such scented attachments include an integrated series of processes to produce a scented article that can deliver a chemically-designed scent or aroma that accurately simulates a familiar and pleasing smell to a user, such as a fruit flavor, a spice flavor, a candy flavor, and the like. The disclosed manufacturing methods and systems account for a plethora of processing parameters and constraints that, if not controlled, can cause undesired variations in the intermediary products that ultimately degrade the final scented material integral to the scented article, and thereby render an inaccurate or inferior scent from the scented attachment (and ruin the scent experience the user would otherwise enjoy while drinking the beverage).

In some example embodiments, a method for manufacturing a scented article, e.g., such as a scented attachment as described above, includes selecting a loading parameter (e.g., % wt, % mass, % mol, and/or volume) of a fragrance material with respect to a base material (e.g., plastic material, such as a polyolefin) to manufacture a scented material; melting the base material in a chamber including mechanically processing the base material to cause the base material to change from a solid phase to a liquid phase or liquid-like phase at a particular viscosity (e.g., in which the particular viscosity of the melted base material has a lower viscosity or viscosity range relative to the solid base material); mixing an amount of the fragrance material in accordance with the selected loading parameter with the melted base material at a predetermined temperature and pressure in the chamber to form an intermediary scented material; extruding the intermediary scented material through holes of an extrusion plate to form an extruded intermediary scented material; modifying the extruded intermediary scented material to form pellets; cooling the pellets in a fluid bath that prevents exposure of the pellets to air and/or atmospheric conditions (e.g., including temperature, humidity and/or oxygen); drying the cooled pellets without applying heat to produce the scented material; and producing a scented article including one or more of injection molding, compression molding, or other material processing technique using the scented material to form a desired shape of the scented article.

In some example embodiments, a system for manufacturing a scented article includes (i) a fragrance material processing system to formulate and/or maintain conditions of a fragrance material that includes an odorless carrier compound and a scent-flavor compound at a particular concentration up to 30% of the fragrance material; (ii) a material processing apparatus including a channel having a plurality of processing zones that includes a first zone to pre-process a base material (e.g., plastic material, such as a polyolefin) and a second zone to introduce and process the fragrance material at a selected load parameter (e.g., % wt, % mass, % mol, and/or volume) with the pre-processed base material; (iii) a continuous screw configured in the channel to produce an intermediary scented material from the processed base material and the fragrance material, in which the screw is operable in the first zone to transform the base material from a solid phase to a liquid phase through physical movement of the screw that mechanically contacts and churns the base material to create heat that melts the base material, and in the second zone to mix the fragrance material with the melted base material at a predetermined temperature in the second zone to form intermediary scented material; (iv) a shaping apparatus including an extrusion plate configured at the end of the channel and including a plurality of holes to extrude the intermediary scented material, and a cutting mechanism to reduce size and modify shape of the extruded intermediary scented material to form scented pellets from the cut and extruded intermediary scented material; (v) a cooling apparatus including a container having a fluid contained therein at a cooling temperature to receive and cool the scented pellets in the fluid that prevents air exposure to the pellets and thereby traps volatile fragrant constituents of the intermediary scented material in the intermediary scented material; (vi) a drying apparatus including a spin dryer to dry the cooled pellets without applying heat; and (vii) a molding apparatus to produce scented articles having a shape and size based on a mold using the scented pellets and/or (viii) a packaging apparatus to collect the cooled scented pellets or the produced scented articles and create a packaging to surround the scented pellets or articles in a manner that restricts air and contaminants from contact with the scented pellets or articles and controls the amount of air and pressure in the packaging.

In implementations of example embodiments of the disclosed methods and systems in accordance with the present technology, challenges to produce scented articles like the scented ring include selecting the right composition parameters of the fragrance material used in the manufacturing process (e.g., such as a fragrance compound in the form of an oil, emulsion or other liquid or liquid like phase). For example, the disclosed methods and systems include engineered fragrance compounds to be compatible with certain polymer base materials, such as polyolefin, in which the fragrance compounds are integrated into the base materials at particularly high loads of the fragrance compound, such as in % concentration or % wt ranges of 10% or greater, e.g., 10-30% fragrance oil. For example, the process of manufacturing the scented material (e.g., in the form of scented pellets) requires determining conditions that provide a material with the right chemical properties to (1) adsorb the fragrance compound and (2) control the release of fragrance compound as a function of time.

In some example embodiments of the fragrance material used to produce scented materials and articles in accordance with the present technology, the fragrance material can include an odorless flavor carrier compound and a scent flavor compound. In some embodiments, the odorless flavor carrier compound includes medium chain triglyceride (MCT) and Triacetin (1,2,3-triacetoxypropane). In such embodiments, for example, the flavor or fragrance material, such as fragrance oil, includes MCT, Triacetin, and the scent-flavor compound, in which the MCT includes a % wt in a range of 50-80% wt, the Triacetin includes a % wt in a range of 15-25% wt, and the scent-flavor compound includes a % wt in a range of 1-30% wt. In some examples, the fragrance oil includes MCT at a 50-70% wt range (e.g., 60% wt), triacetin at a 15-25% wt range (e.g., 20% wt), and the scent-flavor compound at 15-25% wt range (e.g., 20% wt). Table 1 shows an example formulation of a fragrance material (e.g., fragrance oil) in accordance with the present technology, showing a range of weight percentages for constituents of the fragrance material.

TABLE 1

| Constituent | % Weight |
| --- | --- |
| MCT | 50%-80% |
| Triacetin | 15%-25% |
| Scent-flavor compound | 1%-30% |

Some example scent-flavor compounds used in the example methods and systems in accordance with the present technology include, but are not limited to, 15-30% caproates, for example, natural allyl caproate or ethyl caproate for the scent-flavor Pineapple; passionfruit sulfur, for example, methyl 4-propyl 1,3-oxathiane for the scent-flavor Passionfruit; tangerine oil for the scent-flavor Tangerine; ocimenes and menthanethiol or mercaptan for the scent-flavor Mango; lime oil for the scent-flavor Lime; and peppermint oil and menthol for the scent-flavor Mint.

Some of the scent flavor compounds, such as methyl 4-propyl 1,3-oxathine, for example, have a relatively a high vapor pressure (e.g., evaporate rapidly under atmospheric conditions) and can be hard to prevent their diffusion from scented materials. This further illustrates that the disclosed methods and systems (e.g., such as the method 1400 and the system 1500 discussed below) provide effective and efficient techniques for producing scented materials and scented articles, such as the scented ring 610 and/or other examples of the scented rings, when using such constituents to produce the fragrance material.

Figure 14:
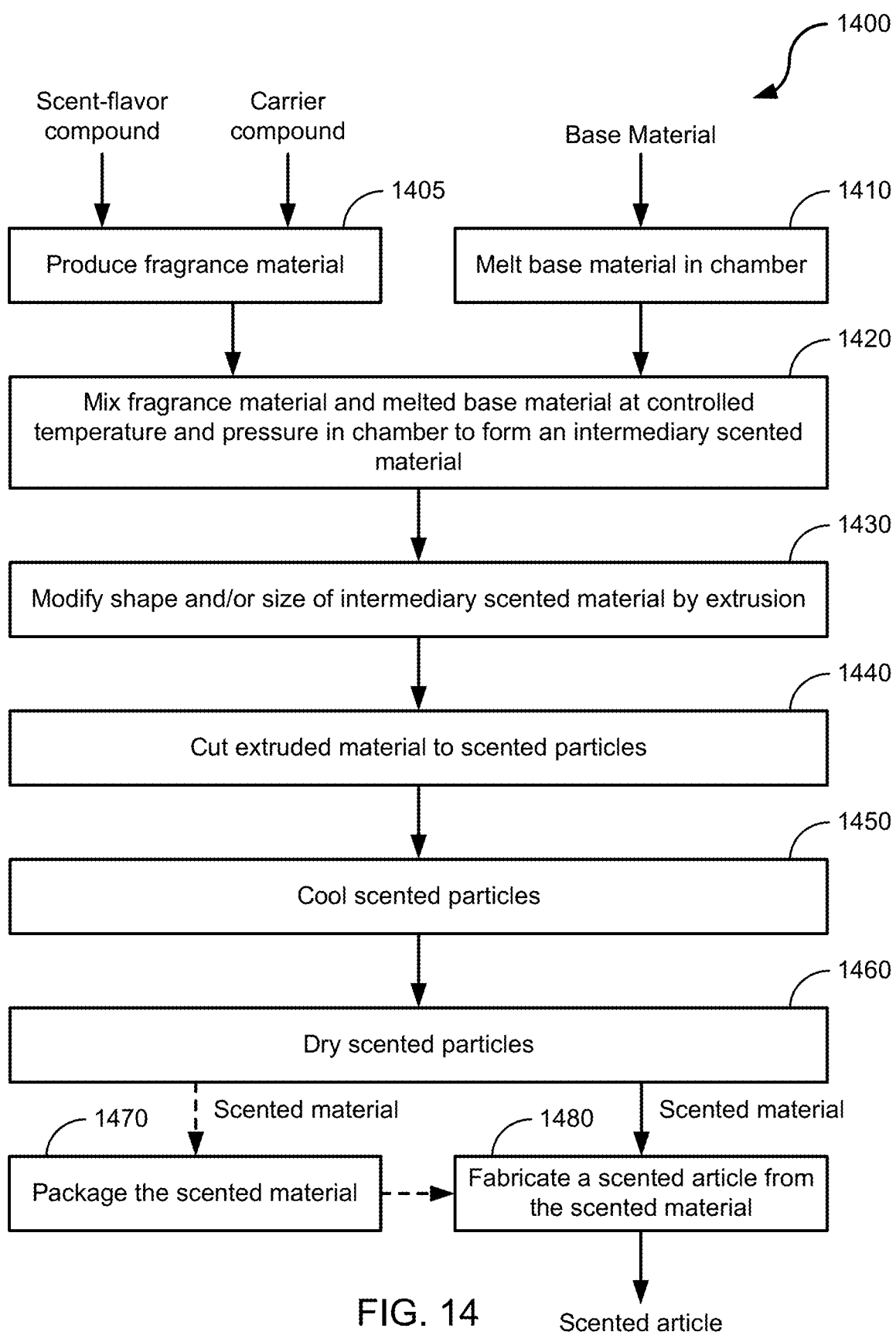
FIG. 14 shows a flow diagram of an example method to manufacture a scented material in accordance with the present technology that can be used to produce a scented article, such as the disclosed scented attachments.

FIG. 14 shows a flow diagram of an example method 1400 to manufacture a scented material in accordance with the present technology that can be used to produce a scented article, such as the disclosed scented attachments. The method 1400 includes a process 1405 to produce a fragrance material from a scent-flavor compound and an odorless carrier compound. In some implementations, for example, the odorless flavor carrier compound includes medium chain triglyceride (MCT) and Triacetin (1,2,3-triacetoxypropane). The scent-flavor chemical constituent or compound can include a variety of substances associated with certain scents. The individual constituents are synthesized into the fragrance material, which in some embodiments is a fragrance oil or other fragrant substance in the form of an emulsion, liquid, or liquid-like phase (e.g., viscous material).

The method 1400 includes a process 1410 to receive a base material, e.g., plastic material such as polyolefin, in a processing chamber and melt the base material to a liquid or liquid-like phase, e.g., having a particular viscosity or viscosity range. In some examples, the viscosity range includes 10 mPa·s to 75 mPa·s, e.g., at temperatures between 95-300 degrees Fahrenheit (° F.). In some implementations, the process 1410 includes mechanically mashing the base material to melt it into a liquid or liquid-like phase of the material. For example, in such implementations, conditions in the processing chamber are controlled through the mechanical processing which holds the mashed and melted material at a controllable temperature and pressure, and thereby reach and maintain a desired viscosity of the base material in the chamber. In some implementations, the temperature in the chamber is maintained in a range between 260-280 degrees Fahrenheit (° F.). In some implementations, the process 1410 includes initially applying heat to the processing chamber, such that the chamber and/or portions of the mechanical processing machine in the chamber are at an elevated temperature, in which the mechanical processing causes an increase in temperature of the base material as it is mashed to cause the melting to the liquid or liquid-like phase. For example, in such implementations, absent the mechanical processing, the base material would remain solid in the chamber. Importantly, the optimization of the mechanical mashing and melting of the base material as described in and the process 1410 can enable the conversion of the base material into a liquid or liquid-like phase, which is required to effectively mix the materials (e.g., base material and fragrance oil). In some embodiments, the method 1400 includes a process to controllably feed the base material into the processing chamber based on the measured values (e.g., weight amount) of the base material in a feeder that supplies the material in the chamber.

The method 1400 includes a process 1420 to receive the fragrance material, e.g., a fragrance oil, in the processing chamber and mix the fragrance material and melted base material at controlled temperature and pressure in the chamber to form an intermediary scented material. In some implementations of the method 1400, the process 1405 or 1420 includes selecting a loading parameter of the fragrance material, such as the % wt, % mass, % mol, and/or volume of the fragrance material, to be processed with the base material to manufacture the intermediary scented material to have a particular % concentration or concentration range of the fragrance material in the base material (e.g., scent loading in a range of 1% to 30%). In some implementations, the process 1420 includes generating different temperatures and pressures in a different region or regions of the chamber to process the mixed materials and form the intermediary scented material. For example, the process 1410 may include a first temperature and/or pressure to melt the base material to the liquid or liquid-like phase, and the process 1420 may include a second temperature and/or pressure to combine the fragrance material and the melted base material to form the intermediary scented material. In some embodiments, the method 1400 includes a process to controllably feed the fragrance material into the processing chamber based on the measured values (e.g., weight and/or volume amount) of the fragrance material in a feeder that supplies the material in the chamber. In some embodiments, the method 1400 includes a process to receive and mix one or more additional compounds or materials with the melted base material and the fragrance material, e.g., such as a colorant.

The fragrance material produced from the process 1405 is a fragrance or aroma substance used in the process 1420 to engineer a specialized material that exhibits a scent for a variety of scented articles. For example, not all fragrance compounds are compatible with certain polymer base materials, particularly with high loads of the fragrance compound (e.g., fragrance oil) in % wt ranges of 10% or greater, e.g., 10-30% fragrance oil. As a result, identifying the right combination of materials requires a rigorous optimization processes involving the variation of numerous materials processing parameters (e.g., temperature, specific amounts of the material, order of addition, etc.) to arrive at a stable, scented material that can encapsulate and retain scent. In particular, the experimental conditions and combinations of polymer base materials and fragrant compounds can have a directed effect on the ability of the material to retain the scent.

The method 1400 includes a process 1430 to receive and modify the shape and/or size of the intermediary scented material through extrusion. For example, in some implementations, the process 1430 includes forcing the intermediary scented material, which is soft and malleable, through holes having a shape and size to form elongated, tubular configurations of an extruded material, e.g., like a spaghetti-like form. In implementations, for example, the process 1430 outputs the extruded material in a container of fluid (e.g., water or other biocompatible or nontoxic aqueous fluids or fluidic substances, like an oil or organic solution). The fluid helps to prevent volatile fragrant compounds from escaping the extruded material.

The method 1400 includes a process 1440 to receive and further modify the shape and/or size of the extruded materials to a small size, e.g., by cutting to form particles. Some examples of the shape-modified scented particles include uncurved-shaped particles or curved-shaped particles like spherical, oval, cylindrical or conical particles, or uncurved shaped particles, e.g., pellets having a dimension in a range of 1/16 inch to 1/4 inch. In implementations, the process 1440 includes depositing the scented particles (e.g., cut pellets) of the extruded material in a container of a fluid (e.g., water or other biocompatible or nontoxic aqueous fluids or fluidic substances, like an oil or organic solution).

The method 1400 includes a process 1450 to receive the scented particles and cool them to a desired temperature (or temperature range) in a manner that prevents volatile fragrant compounds to escape (e.g., diffuse) out of the intermediary scented material during the cooling stage, e.g., by evaporation. In some examples, the desired temperature or temperature range includes at or around room temperature or, in some implementations, in a temperature range of 15-30° C. In some implementations, the process 1450 includes passing the scented particles through a fluid bath (e.g., water bath) to cool the scented particles (e.g., pellets) such that there is no exposure of the scented particles to air and atmospheric conditions while cooling. For example, in such implementations, the fluid (e.g., water) can be pumped in a direction to allow the scented particles to flow through the fluid bath while cooling.

For example, the process 1450, which includes cooling the example pellets in a fluid bath, enables the rapid cooling of the pellets to trap volatile fragrant compounds in the pellets, in which cooling the pellets in a fluid bath provides a pressure greater than the atmosphere such that the pellet is surrounded by a medium dense enough to prevent diffusion (e.g., evaporation) of the scented material. In some implementations, the cooling process may partially occur during the process 1440 and/or the process 1450.

The process 1450 prevents exposure of the scented particles to air and/or atmospheric conditions in order to increase the stability of the resulting particles. For example, implementation of this process precludes altering the composition of the scented pellet by preventing exposure to elements from the air and atmosphere (e.g., temperature fluctuations, changes in humidity, and reactivity of atmospheric gases (e.g., dioxygen)) that could degrade the scented pellet. This process also prevents mixing of contaminants from the atmosphere with the base material in order to ensure that the integrity, that is the scent and stability, of the scented pellet is maintained.

The method 1400 includes a process 1460 to dry the cooled, scented particles and produce the scented material. In some implementations, the process 1460 includes spin drying the intermediary scented material (e.g., particles, in the form of pellets) after it has been cooled to the desired temperature, e.g., in which the spin drying does not include applying heat but can maintain a specific temperature, as applied heat can accelerate volatility of the fragrant compounds formed in the intermediary scented material. The scented material produced by the method 1400 can be used to produce a variety of scented articles, such as the example embodiments of the scented ring described herein.

In some embodiments, the method 1400 can further include a process 1470 to package the dried scented material produced by the process 1460 (e.g., such as the dried scented pellets) in a sealed container. In some implementations of the process 1470, for example, the sealed container includes a vacuum sealed container. For example, the vacuum sealed container can minimize any head room and remove contaminants, like oxygen in air, from the container while the produced scented material (e.g., pellets) remain in packaging for their desired application or use, such as during transit and storage. In certain examples, the vacuum sealed container includes a bin or a bag with aluminum interior lining to prevent evacuation of the scent chemical integrated in the scented material.

In some embodiments, the method 1400 can further include a process 1480 to fabricate a scented article, such as the scented ring 610, 1110, 1120, 1200, 1210, 1220 and/or other examples of the disclosed scented ring, by material-processing the dried scented material (e.g., pellets). For example, in some implementations, a predetermined quantity (e.g., volume and/or mass) of the dried scented material is inputted into a molding machine to compression mold or injection mold the scented article to have a desired design, like a ring, in which, the shape and size of the scented article may be based on the mold. In some implementations, the example molding process of the dried scented material can include venting during molding to allow heat produced during the molding to escape to maintain a favorable temperature and/or pressure of the material being molded into the scented article, e.g., as increased pressure can cause scarring of the final molded product. In some implementations, the example molding process includes cooling the molding material to a temperature that can help prevent volatile chemicals from escaping the scented material. For example, in some implementations, the material-processing of the dried scented material can include adding a colorant, adhesive, or other chemical additive to fabricate the scented article. In various implementations, for example, the process 1480 can be implemented following the process 1460 or 1470.

In some implementations, the method 1400 can further include a process to vacuum seal the scented article in a packaging, e.g., to prevent air, contaminants, or any atmospheric conditions to contact and/or affect the scented article and thereby threaten the quality of the manufactured product. For example, the vacuum sealed packaging can include a bag with aluminum interior lining to prevent evacuation of the scent from the scented article.

Figure 15:
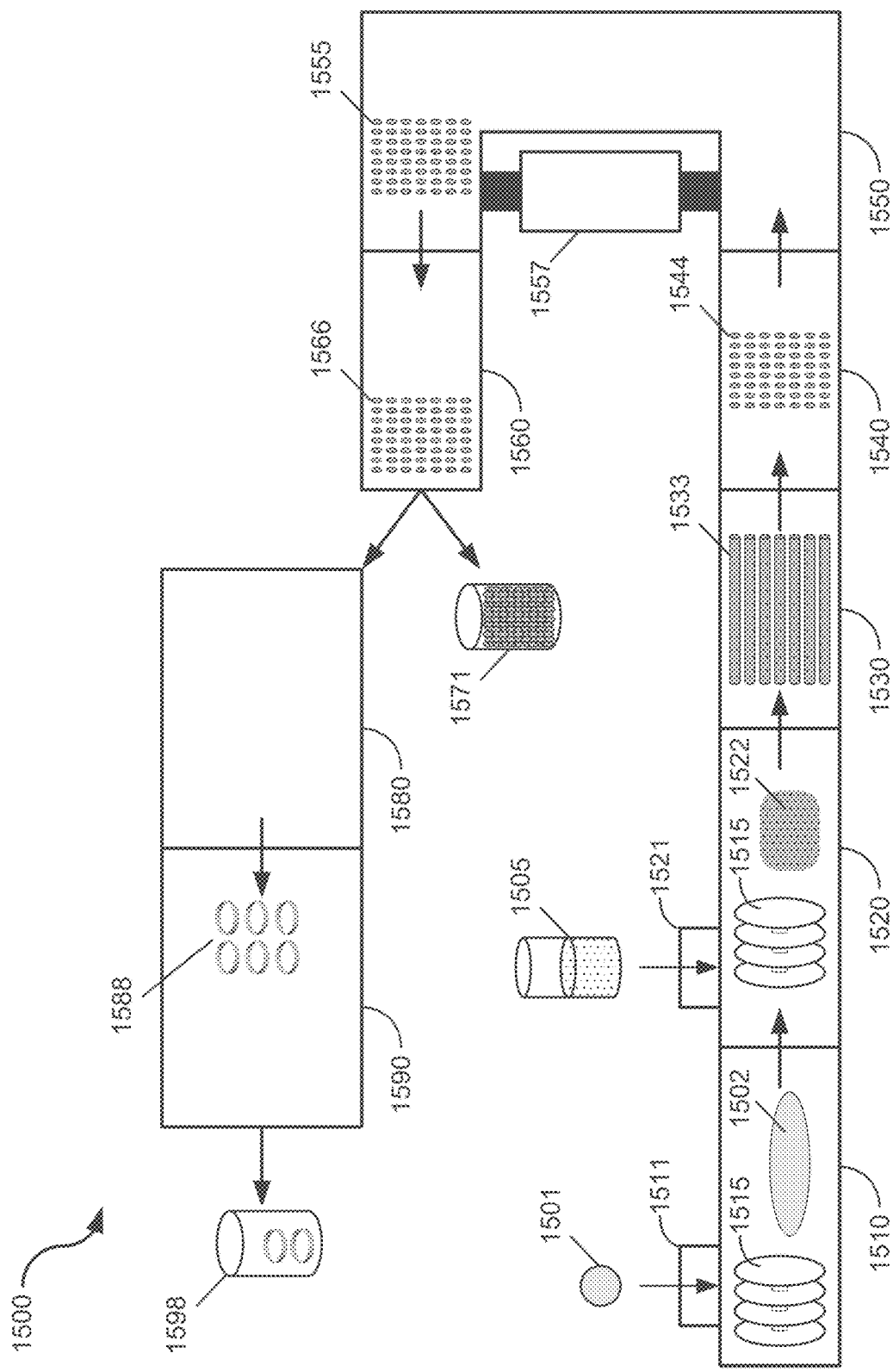
FIG. 15 shows a diagram of an example system to produce a scented material in accordance with the present technology.

FIG. 15 shows a diagram of an example system 1500 to produce a scented material in accordance with the present technology. The system 1500 is operable to perform various embodiments of the method 1400. As shown in FIG. 15, the system 1500 includes a first receiving zone 1510 to receive to receive a base material 1501, e.g., a plastic, such as a polyolefin. In some implementations, in the first receiving zone 1510, the base material 1501 is received in a solid phase and is melted in the zone 1510 from solid phase to form a liquid or liquid-like phase of the base material 1501, shown as liquid or liquid-like base material 1502. In some implementations, the base material 1501 is received in a liquid or liquid-like phase in the zone 1510. In some embodiments, the system 1500 includes a first feeder 1511 to store and/or controllably feed the base material 1501 into first receiving zone 1510.

The base material 1501 can include polyolefin polymer materials. Examples of polyolefin materials used as the base material 1501 include, but are not limited to, low density polyethylene (LDPE), linear low density polyethylene (LLDPE), high density polyethylene (HDPE), polypropylene (PP), and/or LDPE EVA (ethylene vinyl acetate) copolymer, or any blend of these polymers. The new, scented material to be produced using the system 1500 will release a scent when exposed to air, and as such, the base material 1501 to be processed should be selected to have material properties that encapsulate and/or enhance oil retention, stiffness, processability for the scented material. The materials used in the system 1500 can preferably include materials having a flashpoint above 140° F., e.g., to ensure safety in the manufacturing processes.

In some example implementations of methods for manufacturing scented materials, the base material 1501 can include a flex PVC (polyvinyl chloride), cellulose acetates, or polystyrene. Yet, these example materials may require very high temperatures (e.g., over 300° F.) for processing, may be very stiff, and/or may degrade in the presence of the fragrance material, and therefore are not optimal base materials for processing using the system 1500. In some implementations, the base material 1501 can include polymer blends with rubber, such as polyether block amides like Pebax®, which allow oils to be absorbed. Notably, Pebax® is currently an expensive material (e.g., around $6/lb.), and may not be optimal for applications in which cost is a constraint.

The system 1500 includes a kneading assembly 1515 configured in the first receiving zone 1510 and structured to include a chamber and a continuous screw in the chamber that operates to melt the solid phase of the base material 1501 to the liquid or liquid-like phase base material 1502 in the kneading assembly 1515 through physical movement of the screw creating heat to melt the base material 1501 and regulating temperature and pressure of the chamber. The operation of the kneading assembly 1515 provides control of temperature and pressure that are applied to the material inside the kneading assembly 1515. The screw of the kneading assembly 1515 can be structured as a segmented screw. For example, in certain embodiments, the screw can include a twin screw or single screw. In implementations, the screw of the kneading assembly 1515 can move by 'reciprocating' back and forth. The chamber of the kneading assembly 1515 can be configured as a sealed chamber that maintains pressure and temperature regulation inside the kneading assembly 1515.

The example kneading assembly 1515 operates to create a controllable temperature and pressure to mechanically mash and melt the base material 1501 (e.g., plastic) into a liquid, in which pressure is not a setting. Temperature is used to maintain viscosity of the material in the assembly 1515 and hold the material in a liquid or liquid-like state. In some examples, the viscosity range includes 10 mPa·s to 75 mPa·s, e.g., at temperatures between 95-300 degrees Fahrenheit (° F.). In some implementations, the kneading assembly 1515 operates to regulate the material processing temperature in a range of 260-280 degrees Fahrenheit (° F.), e.g., to melt a solid plastic like polyolefins, in the first receiving zone 1510. For example, the physical structure and motion of the screw generates mechanical energy (e.g., torque) that can provide sufficient heat to initially melt the plastic and maintain the melted plastic in the liquid or liquid-like state throughout the production process.

In some embodiments of the kneading assembly 1515, for example, external heaters are not required to melt the plastic. Yet, in some embodiments, for example, the first receiving zone 1510 can additionally or alternatively include a heating unit that applies heat to melt, or assist in melting, the solid base material 1501 to the liquid or liquid-like material 1502 in the chamber. For example, in such implementations, heat can be initially applied to the processing chamber in the zone 1510, such that the chamber and/or the screw of the kneading assembly 1515 are raised to an elevated temperature, but not hot enough to cause melting of the base material 1501, in which the mechanical processing causes an increase in temperature of the base material 1501 as it is processed by the kneading assembly 1515 to produce the base material 1502. For example, in such implementations, absent the mechanical processing by the kneading assembly 1515, the base material would remain solid in the chamber.

The system 1500 includes a second receiving zone 1520 to receive a fragrance oil 1505, e.g., such as an aromatic composition comprising one or more scented chemical constituents mixed with other substances to form a scented oil or other non-solid fragrant. The second receiving zone 1520 is configured proximate to the first receiving zone 1510 of the system 1500 to receive the liquid or liquid-like base material 1502, e.g., liquefied plastic processed by kneading assembly 1515, which is combined with the fragrance oil 1505 received in the zone 1520. As shown in the example of FIG. 15, the kneading assembly 1515 is also configured in the second receiving zone 1520, which processes the fragrance oil 1505 to be mixed with the liquid or liquid-like base material 1502 to form an intermediary scented material 1522. In such embodiments, the first receiving zone 1510 and the second receiving zone 1520 share the same chamber of the kneading assembly 1515, in which the base material 1501 and the fragrance oil 1505 are added at two separate entry points of the chamber, corresponding to the first and second receiving zones 1510 and 1520, respectively. In some embodiments, the system 1500 includes a second feeder 1521 to store and/or controllably feed the fragrance oil 1505 into second receiving zone 1520.

In implementations, for example, the kneading assembly 1515 is operable to generate different temperatures and pressures in different regions of the assembly. For example, in some implementations, the kneading assembly 1515 in the second receiving zone 1520 can operate to raise the temperature of the mixed materials to a second temperature (e.g., ~220° F.) while being churned and pushed through the assembly 1515.

In some embodiments, the kneading assembly 1515, in the first receiving zone 1510, includes one or more a restriction rings so the solid base material 1501 never crosses into the second receiving zone 1520. Therefore, in such embodiments, only the melted material 1502 (e.g., liquid plastic) can migrate to the second receiving zone 1520, e.g., the fragrance/aroma zone. If the solid base material 1501 (e.g., plastic) is not melted by the portion of the chamber where a restriction ring is positioned, the solid base material 1501 gets pushed back until its melted to a form that the restriction ring allows to pass. In some embodiments, the one or more restriction rings include multiple restriction rings with narrowing sizes that narrow down space in the chamber. Similarly, for example, the kneading assembly 1515 is structured to keep oil out of the melting process in the first zone 1510 In implementations, for example, the fragrance oil 1505 is injected into the melted base material 1502 after the solid base material 1501 has melted, which can include processing the solid base material 1501 in the first receiving zone 1510 to have a certain viscosity or viscosity range (10 mPa·s to 75 mPa·s). In some implementations, for example, the melted base material 1502 is processed to have a viscosity that matches the viscosity of the received fragrance oil 1505. For example, the viscosity of the received fragrance oil 1505 can be in a range of 1 mPa·s to 10 Pa·s at room temperature.

In certain embodiments, the feeders 1511 and/or 1521 include a scale to measure mass of the raw materials 1501 and/or 1505 to control the timing, rate, and/or amount of the materials to be released in the respective zones. In accordance with some embodiments of the method 1400, the system 1500 can provide colorant constituents to be mixed with the materials. For example, color can be received at a region of the first receiving zone 1510 to be mixed with the base material 1501 as it is melted by the kneading assembly 1515. In some implementations such as those with a liquid or liquid like raw base material 1501, for example, color can be mixed with the base material 1501 in the first feeder 1511. Similarly, color can be mixed with the fragrance oil 1505 in the second feeder 1521, and/or color can be received at a region of the second receiving zone 1520 to be mixed with the mixed constituent materials 1502 and 1505 as they are churned by the kneading assembly 1515. The sealed chamber of the kneading assembly 1515 can prevent air, contaminants, or any atmospheric conditions to contact and/or affect the fragrance oil 1505 and/or the mixed constituent materials 1502 and 1505 to form the intermediary scented material 1522.

For example, the sealed chamber prevents exposure of the intermediary scented material 1522 to air and/or atmospheric conditions to enhance the stability of the resulting material by precluding reactivity with elements from the air and atmosphere (e.g., temperature fluctuations, changes in humidity, and reactivity of atmospheric gases (e.g., dioxygen)) that could degrade the intermediary scented material 1522).

In some implementations, the system 1500 utilizes the feeders 1511 and/or 1521 to starve-feed the kneading assembly 1515. That is, the feeders 1511 and/or 1521 determine how the screw moves based on the measured values of what is in the feeder, e.g., weight amount. As an example, the feeders 1511 and/or 1521 can measure a relatively high weight of the raw materials that corresponds to a first speed of the screw turning; and the feeders 1511 and/or 1521 can measure a lower weight of the raw materials in the feeder(s) that corresponds to a second speed of the screw turning. As such, the fragrance oil 1505 can be injected into the system 1500 on a computerized loss and weight feeder.

In some implementations, the base material 1501 may already be in the form of base material 1502, i.e., liquid or liquid-like form, e.g., capable of flow. In such implementations, the liquid base material 1502 and the fragrance oil 1505 can be added at the same point of entry at the kneading assembly 1515 in the chamber, in which the first and second receiving zones 1510 and 1520 are the same physical zone, but may vary from a temporal aspect as to when the materials 1501 and 1505 are received.

In other embodiments, one or both of the first and second receiving zones 1510 and 1520 can include a continuous mixer assembly or a batch mixer assembly to mix the base material 1501 and the fragrance oil 1505.

The system 1500 includes a zone 1530 to receive and process the intermediary scented material 1522 produced by the kneading assembly 1515 to modify its shape and size, e.g., by extrusion. In some embodiments, the zone 1530 includes an extrusion plate, e.g., a metal face plate, with a plurality of holes configured perpendicular with the material flow direction at the end face of the kneading assembly 1515. For example, an extruded material 1533 is formed in elongated shapes and sizes defined by the holes of the plate. In some embodiments, the system 1500 includes a container of a fluid (e.g., water or other biocompatible or nontoxic aqueous fluids or fluidic substances, like an oil or organic solution) in the zone 1530, in which the intermediary scented material 1522 is received and modified, e.g., by extrusion. In some implementations, the extruded material 1533 is forced out of the kneading assembly 1515 through the holes of the extrusion plate in the zone 1530 in a spaghetti-like form.

In some embodiments, the system 1500 includes a zone 1540 to receive and process the extruded material 1533 to further modify its shape and size, e.g., such as cut to form scented particles, including beads, pellets or other smaller particles. In some embodiments, the system 1500 includes a container of a fluid (e.g., water or other biocompatible or nontoxic aqueous fluids or fluidic substances, like an oil or organic solution) and a blade cutter in the zone 1540, in which the blade cutter cuts the shape-formed extruded material 1533 to scented particles 1544 (e.g., pellets) submerged in the fluid. In some implementations, for example, a blade of the cutter spins behind the metal plate with holes and cuts the spaghetti-like extruded material 1533 into small scented particles 1544. For example, the size of example pellets can include a ⅛ inch round size. In some implementations, the pellet size is not essential if the method for manufacture includes a re-melting process. Whereas, in some embodiments, the system 1500 provides the extruded material 1533 directly to a cooling zone, discussed below.

The system 1500 includes a cooling zone 1550 including a fluid (e.g., water or other biocompatible or nontoxic aqueous fluids or fluidic substances, like an oil or organic solution) at a predetermined temperature to receive the cut scented particles 1544 and cool them to a desired temperature (or temperature range) to form a scented material 1555, e.g., in the shape of scented particles or other shape of the intermediary scented material 1522 after the zone 1530. In some examples, the desired temperature or temperature range includes at or around room temperature, or in some implementations in a temperature range of 15-30° C. In some embodiments, the cooling zone 1550 includes a fluid bath (e.g., water bath) arranged at the end of the kneading assembly 1515 to span between the zones 1530, 1540 and 1550, including after the extrusion plate and the cutter, which receives the scented particles 1544 and flows them in the fluid bath along a channel to be cooled to the desired temperature or temperature range. For example, in some implementations, the cooling zone 1550 can include a pump 1557 that pumps fluid in the fluid bath to create a flow that can drive the scented particles 1544 from one region of the water bath to another region of the water bath of the cooling zone 1550. In the cooling zone 1550, the fluid (e.g., water) is circulated back and forth and temperature controlled. In some implementations, the fluid (e.g., water) in the cooling zone is set to a predetermined temperature of 80-85° F. In an example embodiment, the water bath is structured as a stainless steel tube to span a distance (e.g., 30 ft.) to facilitate the example pellets traveling the distance of the tube in the fluid.

The cooling zone 1550 provides a cooling module that prevents the volatile constituents of the intermediary scented material (e.g., formed as the particles, such as pellets) from immediately escaping the formed material. The cooling zone operates by slowing down the sublimation process of the scented materials (e.g., where the scented material is converted to a gas (vapor) and is released into the atmosphere) in order to effectively trap the scent in the scented materials. To form a scented material in accordance with the present technology, the intermediary scented material must be cooled to a desired temperature using a fluid to trap the volatile chemicals from escaping (e.g., evaporating), which could otherwise escape in air. In some embodiments, after the scented particles 1544 are cooled to the desired temperature in the cooling zone 1550, e.g., room temperature (e.g., 22-27° C.) or just above room temperature, the cooled scented material 1555 can be dried by spin drying and/or applying a gas (such as nitrogen) or air.

For example, in implementations, cooling the scented particles in a fluid bath enables the rapid cooling of the particle to trap volatile fragrant compounds in the scented material as a consequence in the difference between the heat capacity of water vs air. Also, for example, cooling the scented particles in a fluid bath provides a pressure greater than the atmosphere such that the particle (e.g., pellet) is surrounded by a medium dense enough to prevent diffusion (e.g., evaporation) of the scented material.

For example, preventing exposure of the scented material to air and/or atmospheric conditions during the manufacturing increases the stability of the resulting scented particle by precluding contamination with elements from the air and atmosphere. Such elements in the air and atmosphere can include, but are not limited to, fluctuations in temperature, changes in humidity and reactive of atmospheric gases (e.g., dioxygen) that could degrade the scented material. Also, for example, preventing exposure from air and atmosphere excludes the incorporation of impurities into the scented particles that could affect the particle's scent and stability.

The system 1500 includes a drying zone 1560 to dry the cooled, scented material 1555 (e.g., particles, such as pellets, beads, etc.) to produce an engineered scented material 1566. In some embodiments, the drying zone 1560 includes a spin dryer to spin dry the cooled, scented material 1555. The scented particles are not heated in the drying zone 1560, as applied heat can accelerate volatility of the fragrant compounds formed in the cooled, scented material 1555. In some embodiments, the drying zone 1560 can also include a packaging system to receive the dried, engineered scented material 1566 (e.g., formed as pellets) and seal the engineered scented material 1566 in one or more sealed containers 1571. In some embodiments, the packaging system of the drying zone 1560 is arranged adjacent and separate from the spin dryer or other example drying apparatus. In such embodiments, the dried, engineered scented material 1566 are provided to the packaging system, which includes one or more openings at a terminal end to allow the one or more sealed containers 1571 to reversibly fasten so that the engineered scented material 1566 can be packaged within the sealed container(s) 1571 that minimizes exposure to air, moisture, and contaminants.

In some embodiments, the system 1500 can further include article processing machine or system 1580 to receive the engineered scented material 1566, e.g., directly from the drying zone 1560 or indirectly from the drying zone 1560 via from a packaging like container 1571, and to process the engineered scented material 1566 to produce a scented article 1588. In some embodiments, the article processing machine 1580 includes a compression molding or injection molding machine to fabricate the scented article 1588 based on a mold having a predetermined shape and size to create the article, such as a scented ring, scented sheet, or other design of the scented article. In some examples, the article processing machine 1580 includes a hot runner mold system or a gated molding system. In certain embodiments, for example, the gated molding system includes one or more mold chamber shaped to dimensions of a ring, and a small tube component that connects with the mold chamber to provide a gate to expel waste product (e.g., which can be recycled). For example, the body of the scented article 1588 may be fabricated using compression molding, during which process the engineered scented material 1566 is shaped based on the mold and may include a colorant, adhesive, or other chemical additive be added to the article, in which the compression-molded end product includes color, and/or an additive is used to aid in the release of the product from the mold. In some examples, the scented article 1588 is made from a single piece of shaped or otherwise molded material and may include a cavity into which the engineered scented material 1566 is injected.

In some embodiments, the system 1500 can further include an article packaging machine or system 1590 to package the scented article 1588 in a manner that restricts air and contaminants from contact with the scented articles and controls the amount of air and pressure in the packaging. In some implementations, the article packaging machine 1590 provides a vacuum sealed packaging 1598, e.g., in which a predetermined amount of scented articles 1588 of the same fragrance or aroma are packaged in a single vacuum packaging. For example, the predetermined amount can be selected by quantity of scented articles 1558, by weight of scented articles 1558, by volume of scented articles 1558, or the like. In some implementations, the article packaging machine 1590 separates the inputted scented articles 1588, based on the batch order of input, such that scented articles of a first scent (e.g., mint) are packaged in a separate packaging from scented articles of a second scent (e.g., pineapple).

In some implementations of methods for manufacturing using the system 1500, the time between initiating feeding of the materials 1501 and 1505 and the pellet formation can include producing 500 lbs. of the produced material (pellets) per hour. As such, a single pellet 1544 can be produced in the zones 1510-1540 in approximately 15 seconds. In some implementations, the dwell time in the cooling zone includes only a few seconds (e.g., 2 to 5 seconds). Spin drying the example scented pellets can include times of a few seconds to one minute, in some examples. Therefore, methods for manufacturing scented materials using the system 1500 can produce a container of the scented material 1566 in under a minute.

EXAMPLES

In some example embodiments, a method for manufacturing a scented material (example D1) includes melting a base material (e.g., plastic material) in a chamber including mechanically processing the base material to cause the base material to change from a solid phase to a liquid phase or liquid-like phase at a particular viscosity; mixing a fluid fragrance material with the melted base material at a predetermined temperature and/or pressure in the chamber to form an intermediary scented material; extruding the intermediary scented material through holes of an extrusion plate to form an extruded intermediary scented material; cooling the intermediary scented material in a fluid bath that prevents exposure of the intermediary scented material to air and/or harmful atmospheric conditions including temperature, humidity and/or oxygen; and drying the cooled scented material without applying heat to produce a scented material.

Example D2 includes the method of example D1, in which the mechanically processing the base material is performed at a controllable temperature and pressure determined by mechanical energy associated with churning the base material.

Example D3 includes the method of example D2, in which the controllable temperature and pressure include a first temperature and pressure to melt the base material, and the predetermined temperature and pressure include a second temperature and pressure to combine the fragrance material and the melted base material to form the intermediary scented material.

Example D4 includes the method of example D1, further including mixing an additional material with the melted base material and the fragrance material.

Example D5 includes the method of example D4, in which the additional material includes a colorant.

Example D6 includes the method of example D1, further including controllably feeding the base material into the chamber based on one or more measured values of the base material to supply the base material in the chamber.

Example D7 includes the method of example D1, further including controllably feeding the fluid fragrance material into the chamber based on one or more measured values of the fragrance material to supply the fragrance material in the chamber.

Example D8 includes the method of example D1, further including modifying the extruded intermediary scented material to form scented particles, in which the cooling the intermediary scented material includes cooling the scented particles in the fluid bath, and the drying includes drying the cooled scented particles.

Example D9 includes the method of example D8, in which the extruding includes forcing the intermediary scented material through holes of the extrusion plate having a curved shape and predetermined size to form an elongated, tubular extruded material, and in which the modifying includes cutting the elongated, tubular extruded material to the scented particles.

Example D10 includes the method of example D1, further including initially applying heat to the chamber, such that at least some portions of the chamber are at an elevated temperature, wherein the mechanically processing causes an increase in temperature of the base material as it is mechanically processed to cause the melting of the base material to the liquid phase or liquid-like phase.

Example D11 includes the method of example D1, further including selecting a loading parameter of the fragrance material with respect to the base material, in which the loading parameter includes a % concentration of the scented material in a range of 1% to 30%.

Example D12 includes the method of example D1, further including producing a scented article including molding the scented material to particular shape of the scented article.

Example D13 includes the method of example D12, in which the particular shape includes a ring.

Example D14 includes the method of any of the preceding examples, in which the fragrance material includes a fragrance oil.

Example D15 includes the method of any of the preceding examples, in which the base material includes a plastic material including a polyolefin.

In some example embodiments, a system for manufacturing a scented material (example D16) includes a material processing chamber including a channel having a first zone to process a base material and a second zone to process a fragrance material with the processed base material; a continuous screw configured in the channel to produce an intermediary scented material from the processed base material and the fragrance material, in which the screw is operable in the first zone to transform the base material from a solid phase to a liquid phase through physical movement of the screw that mechanically contacts and churns the base material to create heat that melts the base material, and in the second zone to mix the fragrance material with the melted base material at a predetermined temperature in the second zone to form intermediary scented material; a shaping apparatus including an extrusion plate configured at the end of the channel and including a plurality of holes to extrude the intermediary scented material; a cooling apparatus including a container having a fluid contained therein at a cooling temperature to receive and cool the scented intermediary scented material (e.g., shaped intermediary scented material) in the fluid that prevents air exposure to the intermediary scented material and thereby traps volatile fragrant constituents of the intermediary scented material within; and a drying apparatus to dry the cooled scented material without applying heat, thereby producing the scented material.

Example D17 includes the system of example D16, in which the screw includes a twin screw or a single screw.

Example D18 includes the system of example D16, in which the screw is configured to move by reciprocating motion back and forth to drive processed material forward through the channel.

Example D19 includes the system of example D16, in which the material processing chamber is a sealed chamber that maintains pressure and temperature regulation therein.

Example D20 includes the system of example D16, in which the continuous screw is operable to melt the base material in a first zone by mechanically processing the base material to cause the base material to transform from the solid phase to the liquid phase at a particular viscosity.

Example D21 includes the system of example D16, in which the shaping apparatus includes a cutting mechanism to reduce the size and modify the shape of the extruded intermediary scented material to form scented particles from the cut and extruded intermediary scented material.

Example D22 includes the system of example D16, wherein the drying apparatus includes a spin dryer to spin dry the cooled scented material.

Example D23 includes the system of example D16, further including a molding apparatus to produce a scented article having a shape and size based on a mold using the scented material.

Example D23 includes the system of any of the preceding examples, in which the fragrance material includes a fragrance oil.

Example D24 includes the system of any of the preceding examples, in which the base material includes a plastic material including a polyolefin.

In some example embodiments, a scented attachment for a beverage container (example D25) includes a scented article including a body loaded with a volatile chemical compound to emanate from the body of the scented article to generate a scent, wherein the scented article includes at least one interior protruding structure that projects from an interior wall of the body of the scented article and is configured to fasten to a bottle and be enclosed by a cap and the bottle when the cap is securely fastened to the bottle, such that the scent from the scented attachment is trapped when the cap is securely attached to the bottle and releases into an outer environment when the cap is detached from the bottle, wherein the scented article comprises a scented material formed of a fragrance oil and a plastic base material, and wherein the scented article is produced by a process comprising: selecting a loading parameter of the fragrance oil with respect to the plastic base material to manufacture the scented material, wherein the loading parameter includes a % concentration of the scented material in a range of 1% to 30%; melting the plastic base material in a chamber including mechanically processing the base material to cause the plastic base material to change from a solid phase to a liquid phase or liquid-like phase at a particular viscosity; mixing an amount of the fragrance oil in accordance with the selected loading parameter with the melted base material at a predetermined temperature and pressure in the chamber to form an intermediary scented material; extruding the intermediary scented material through holes of an extrusion plate to form an extruded intermediary scented material; modifying the extruded intermediary scented material to form scented particles; cooling the scented particles in a fluid bath that prevents exposure of the scented particles to air; drying the cooled scented particles without applying heat to produce the scented material; and producing the scented article by molding the scented particles to a shape of the scented article.

Example D26 includes the scented attachment of any of examples D25 and D27-D43, wherein the fragrance material can include a carrier compound and the volatile chemical compound.

Example D27 includes the scented attachment of example D26, wherein the carrier compound includes medium chain triglyceride (MCT) and Triacetin (1,2,3-triacetoxypropane).

Example D28 includes the scented attachment of example D26, wherein the volatile chemical compound includes at least one of (i) caproates including a natural allyl caproate and/or ethyl caproate for a scent-flavor of pineapple; (ii) passionfruit sulfur including methyl 4-propyl 1,3-oxathiane for the scent-flavor of passionfruit; (iii) tangerine oil for the scent-flavor of tangerine; (iv) ocimenes and menthanethiol or mercaptan for the scent-flavor of mango; (v) lime oil for the scent-flavor of lime; or (vi) peppermint oil and menthol for the scent-flavor of mint.

Example D29 includes the scented attachment of any of examples D26-D28, wherein the fragrance oil includes a % wt of the MCT in a range of 50-80% wt, a % wt of the Triacetin in a range of 15-25% wt, and a % wt of the volatile chemical compound in a range of 1-30% wt.

Example D30 includes the scented attachment of example D29, wherein the fragrance oil includes MCT at substantially 60% wt, Triacetin at substantially 20% wt, and the volatile chemical compound at substantially 20% wt.

Example D31 includes the scented attachment of any of examples D25-D30 and D32-D43, wherein the bottle is structured to contain a fluid beverage, and the bottle includes a body region and a neck region, the bottle including a collar that extends outward and circumferentially around the neck region, and a ledge structure that extends outward and circumferentially around the neck region and is positioned above the collar, wherein the scented article is configured to fasten around the neck region of the bottle based on contact between the at least one interior protruding structure of the scented article and a ledge structure of the bottle, wherein the at least one interior protruding structure is positioned below the ledge structure.

Example D32 includes the scented attachment of any of examples D25-D31 and D33-D43, wherein the cap is reversibly attachable to the bottle, and the cap includes an interior rim structure that projects from and circumferentially around an interior cap wall of the cap, wherein the cap is structured to enclose the scented article in a compartment formed between the collar of the bottle and the interior rim structure of the cap when the cap is securely fastened to the bottle.

Example D33 includes the scented attachment of any of examples D25-D32 and D34-D43, wherein the scented article includes a scent ring.

Example D34 includes the scented attachment of example D33, wherein the scent ring further includes at least one exterior protruding structure that projects from an exterior wall of the body of the scent ring.

Example D35 includes the scented attachment of example D34, wherein the scent ring is configured to detachably couple to the cap prior to initial attachment of the cap and the scent ring to the bottle, wherein the scent ring initially couples to the cap based on contact between the at least one exterior protruding structure of the scent ring and the interior rim structure of the cap, and when the cap is initially fastened to the bottle the scent ring transfers from being coupled to the cap to being coupled to the bottle based on contact between the at least one interior protruding structure of the scent ring and the ledge structure of the bottle.

Example D36 includes the scented attachment of any of examples D25-D35 and D37-D43, wherein the scent ring includes a cut-away region across the body to allow the scent ring to be detachably coupled to the bottle, such that the scent ring is selectively detachable from the bottle.

Example D37 includes the scented attachment of any of examples D25-D38 and D36-D43, wherein the molding includes injection molding or compression molding using the scented material.

Example D38 includes the scented attachment of any of examples D25-D39 and D40-D43, wherein the molding includes producing one or more pores that recede inward with respect to an outer surface of the body of the scented article.

Example D39 includes the scented attachment of example D38, wherein the one or more pores include a plurality of pores arranged along the outer surface of the body of the scent ring in an array of periodic positions or aperiodic positions, or is randomly positioned.

Example D40 includes the scented attachment of any of examples D25-D39 and D41-D43, wherein the molding includes producing one or more protrusions that protrude outward with respect to an outer surface of the body of the scented article.

Example D41 includes the scented attachment of example D40, wherein the one or more protrusions include a plurality of protrusions arranged along the surface of the body of the scent ring in an array of periodic positions or aperiodic positions, or is randomly positioned.

Example D42 includes the scented attachment of any of examples D25-D41 and D43, wherein the process to produce the scented attachment further comprises: creating a packaging to surround the scented article or a plurality of the scented articles to restrict air and contaminants from contact with the scented article or articles.

Example D43 includes the scented attachment of the preceding examples, wherein the base material includes a plastic material including a polyolefin.

In some example embodiments, a scented attachment for a beverage container (example D44) includes a scented article having a body that comprises a scented material including a plastic material loaded with a volatile chemical compound to emanate from the body of the scented article to generate a scent, wherein the scented article includes at least one interior protruding structure that projects from an interior wall of the body of the scented article and is configured to attach to a bottle, wherein the scented article is produced by a process comprising: selecting a loading parameter of a fragrance oil with respect to a plastic base material to manufacture the scented material, wherein the loading parameter includes a % concentration of the scented material in a range of 1% to 30%; melting the plastic base material in a chamber including mechanically processing the base material to cause the plastic base material to change from a solid phase to a liquid phase or liquid-like phase at a particular viscosity; mixing an amount of the fragrance oil in accordance with the selected loading parameter with the melted base material at a predetermined temperature and pressure in the chamber to form an intermediary scented material; extruding the intermediary scented material through holes of an extrusion plate to form an extruded intermediary scented material; modifying the extruded intermediary scented material to form scented particles; cooling the scented particles in a fluid bath that prevents exposure of the scented particles to air; drying the cooled scented particles without applying heat to produce the scented material; and producing the scented article by molding the scented particles to a shape of the scented article.

Example D45 includes the scented attachment of any of examples D44 or D46-67, wherein the beverage container includes a cap, and the scented article is configured to be enclosed by a cap and the bottle when the cap is securely fastened to the bottle, such that the scent from the scented article is trapped when the cap is securely attached to the bottle and releases into an outer environment when the cap is detached from the bottle.

Example D46 includes the scented attachment of example D45, wherein the bottle is structured to contain a fluid beverage, and the bottle includes a body region and a neck region, the bottle including a collar that extends outward and circumferentially around the neck region, and a ledge structure that extends outward and circumferentially around the neck region and is positioned above the collar, wherein the scented article is configured to fasten around the neck region of the bottle based on contact between the at least one interior protruding structure of the scented article and a ledge structure of the bottle, wherein the at least one interior protruding structure is positioned below the ledge structure.

Example D47 includes the scented attachment of example D45, wherein the cap is reversibly attachable to the bottle, and the cap includes an interior rim structure that projects from and circumferentially around an interior cap wall of the cap, wherein the cap is structured to enclose the scented article in a compartment formed between the collar of the bottle and the interior rim structure of the cap when the cap is securely fastened to the bottle.

Example D48 includes the scented attachment of example D45, wherein the scented article includes a scent ring.

Example D49 includes the scented attachment of example D48, wherein the scent ring further includes at least one exterior protruding structure that projects from an exterior wall of the body of the scent ring.

Example D50 includes the scented attachment of example D49, wherein the scent ring is configured to detachably couple to the cap prior to initial attachment of the cap and the scent ring to the bottle, wherein the scent ring initially couples to the cap based on contact between the at least one exterior protruding structure of the scent ring and the interior rim structure of the cap, and when the cap is initially fastened to the bottle the scent ring transfers from being coupled to the cap to being coupled to the bottle based on contact between the at least one interior protruding structure of the scent ring and the ledge structure of the bottle.

Example D51 includes the scented attachment of example D48, wherein the scent ring includes a cut-away region across the body to allow the scent ring to be detachably coupled to the bottle, such that the scent ring is selectively detachable from the bottle.

Example D52 includes the scented attachment of any of examples D44-D51 and D53-D67, wherein the plastic material includes a low density polyethylene (LDPE), a linear low density polyethylene (LLDPE), or an ethylene vinyl acetate (EVA), or a combination of any thereof.

Example D53 includes the scented attachment of any of examples D44-D52 and D54-D67, wherein the volatile chemical compound is loaded in the plastic material at a % concentration of 10%-30%.

Example D54 includes the scented attachment of any of examples D44-D53 and D55-D67, wherein the fragrance oil includes a carrier compound and a scented chemical compound.

Example D55 includes the scented attachment of example D54, wherein the carrier compound includes medium chain triglyceride (MCT) and Triacetin (1,2,3-triacetoxypropane).

Example D56 includes the scented attachment of example D54, wherein the scented chemical compound includes at least one of (i) caproates including a natural allyl caproate and/or ethyl caproate for a scent-flavor of pineapple; (ii) passionfruit sulfur including methyl 4-propyl 1,3-oxathiane for the scent-flavor of passionfruit; (iii) tangerine oil for the scent-flavor of tangerine; (iv) ocimenes and menthanethiol or mercaptan for the scent-flavor of mango; (v) lime oil for the scent-flavor of lime; or (vi) peppermint oil and menthol for the scent-flavor of mint.

Example D57 includes the scented attachment of any of examples D54-D56, wherein the fragrance oil includes a % wt of MCT in a range of 50-80% wt, a % wt of Triacetin in a range of 15-25% wt, and a % wt of the scented chemical compound in a range of 1-30% wt.

Example D58 includes the scented attachment of any of examples D54-D56, wherein the fragrance oil includes MCT at substantially 60% wt, Triacetin at substantially 20% wt, and the volatile chemical compound at substantially 20% wt.

Example D59 includes the scented attachment of any of examples D44-D58 and D60-D67, wherein the molding includes injection molding or compression molding using the scented material.

Example D60 includes the scented attachment of any of examples D44-D59 and D61-D67, wherein the molding includes producing one or more pores that recede inward with respect to an outer surface of the body of the scented article.

Example D61 includes the scented attachment of example D60, wherein the one or more pores include a plurality of pores arranged along the outer surface of the body of the scent ring in an array of periodic positions or aperiodic positions, or is randomly positioned.

Example D62 includes the scented attachment of any of examples D44-D61 and D63-D67, wherein the molding includes producing one or more protrusions that protrude outward with respect to an outer surface of the body of the scented article.

Example D63 includes the scented attachment of example D62, wherein the one or more protrusions include a plurality of protrusions arranged along the surface of the body of the scent ring in an array of periodic positions or aperiodic positions, or is randomly positioned.

Example D64 includes the scented attachment of any of examples D44-D63 and D65-D67, wherein the process to produce the scented attachment further comprises: creating a packaging to surround the scented article or a plurality of the scented articles to restrict air and contaminants from contact with the scented article or articles.

Example D65 includes the scented attachment of example D64, wherein the packaging includes a sealed container that interfaces with an apparatus that dries the cooled scented particles without applying heat to produce the scented material.

Example D66 includes the scented attachment of any of examples D44-D65 and D67, wherein the plastic base material includes a polyolefin.

Example D67 includes the scented attachment of any of examples D44-D66, wherein the plastic base material includes a polymer blend with rubber.

It is intended that the specification, together with the drawings, be considered exemplary only, where exemplary means an example. As used herein, the singular forms "a", "an" and "the" are intended to include the plural forms as well, unless the context clearly indicates otherwise. Additionally, the use of "or" is intended to include "and/or", unless the context clearly indicates otherwise.

While various instances have been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the invention. All such modifications are intended to be within the scope of the claims appended hereto.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A scented attachment for a beverage container, comprising:
a scented article having a body that comprises a scented material including a plastic material loaded with a volatile chemical compound to emanate from the body of the scented article to generate a scent, wherein the scented article includes at least one interior protruding structure that projects from an interior wall of the body of the scented article and is configured to attach to a bottle,
wherein the scented material is formulated with a fragrance oil that includes a carrier compound and a scented chemical compound, wherein the carrier compound includes medium chain triglyceride (MCT) and Triacetin (1,2,3-triacetoxypropane), and wherein the fragrance oil includes a % wt of MCT in a range of 50-80% wt, a % wt of Triacetin in a range of 15-25% wt, and a % wt of the scented chemical compound in a range of 1-30% wt.

2. The scented attachment of claim 1, wherein the beverage container includes a cap, and the scented article is configured to be enclosed by a cap and the bottle when the cap is securely fastened to the bottle, such that the scent from the scented article is trapped when the cap is securely attached to the bottle and releases into an outer environment when the cap is detached from the bottle.

3. The scented attachment of claim 2, wherein the bottle is structured to contain a fluid beverage, and the bottle includes a body region and a neck region, the bottle including a collar that extends outward and circumferentially around the neck region, and a ledge structure that extends outward and circumferentially around the neck region and is positioned above the collar, wherein the scented article is configured to fasten around the neck region of the bottle based on contact between the at least one interior protruding structure of the scented article and a ledge structure of the bottle, wherein the at least one interior protruding structure is positioned below the ledge structure.

4. The scented attachment of claim 2, wherein the cap is reversibly attachable to the bottle, and the cap includes an interior rim structure that projects from and circumferentially around an interior cap wall of the cap, wherein the cap is structured to enclose the scented article in a compartment formed between the collar of the bottle and the interior rim structure of the cap when the cap is securely fastened to the bottle.

5. The scented attachment of claim 2, wherein the scented article is a scent ring.

6. The scented attachment of claim 5, wherein the scent ring further includes at least one exterior protruding structure that projects from an exterior wall of the body of the scent ring.

7. The scented attachment of claim 6, wherein the scent ring is configured to detachably couple to the cap prior to initial attachment of the cap and the scent ring to the bottle, wherein the scent ring initially couples to the cap based on contact between the at least one exterior protruding structure of the scent ring and the interior rim structure of the cap, and when the cap is initially fastened to the bottle the scent ring transfers from being coupled to the cap to being coupled to the bottle based on contact between the at least one interior protruding structure of the scent ring and the ledge structure of the bottle.

8. The scented attachment of claim 5, wherein the scent ring includes a cut-away region across the body to allow the scent ring to be detachably coupled to the bottle, such that the scent ring is selectively detachable from the bottle.

9. The scented attachment of claim 1, wherein the plastic material includes a low density polyethylene (LDPE), a linear low density polyethylene (LLDPE), or an ethylene vinyl acetate (EVA), or a combination of any thereof.

10. The scented attachment of claim 1, wherein the volatile chemical compound is loaded in the plastic material at a % concentration of 10%-30%.

11. The scented attachment of claim 1, wherein the scented chemical compound includes at least one of (i) caproates including a natural allyl caproate and/or ethyl caproate for a scent-flavor of pineapple; (ii) passionfruit sulfur including methyl 4-propyl 1,3-oxathiane for the scent-flavor of passionfruit; (iii) tangerine oil for the scent-flavor of tangerine; (iv) ocimenes and menthanethiol or mercaptan for the scent-flavor of mango; (v) lime oil for the scent-flavor of lime; or (vi) peppermint oil and menthol for the scent-flavor of mint.

12. The scented attachment of claim 1, wherein the fragrance oil includes MCT at substantially 60% wt, Triacetin at substantially 20% wt, and the volatile chemical compound at substantially 20% wt.

\* \* \* \* \*